United States Patent
Kawano et al.

(10) Patent No.: US 11,274,076 B2
(45) Date of Patent: Mar. 15, 2022

(54) PROCESS FOR PREPARING 1, 2-BENZENEDIMETHANOL COMPOUND

(71) Applicant: GOWAN COMPANY, L.L.C., Yuma, AZ (US)

(72) Inventors: Tsuyoshi Kawano, Ibaraki (JP); Makoto Bamba, Ibaraki (JP); Daisuke Horikoshi, Ibaraki (JP)

(73) Assignee: GOWAN COMPANY, L.L.C., Yuma, AZ (US)

( * ) Notice: Subject to any disclaimer, the term of this patent is extended or adjusted under 35 U.S.C. 154(b) by 776 days.

(21) Appl. No.: 16/076,153

(22) PCT Filed: Feb. 8, 2016

(86) PCT No.: PCT/JP2016/053650
§ 371 (c)(1),
(2) Date: Aug. 7, 2018

(87) PCT Pub. No.: WO2017/138068
PCT Pub. Date: Aug. 17, 2017

(65) Prior Publication Data
US 2020/0399263 A1   Dec. 24, 2020

(51) Int. Cl.
*C07C 309/66* (2006.01)
*C07C 303/24* (2006.01)

(52) U.S. Cl.
CPC .......... *C07C 309/66* (2013.01); *C07C 303/24* (2013.01)

(58) Field of Classification Search
CPC ..................... C07C 309/66; C07C 303/24
See application file for complete search history.

(56) References Cited

U.S. PATENT DOCUMENTS

| | | |
|---|---|---|
| 4,218,464 A | 8/1980 | Bondinell et al. |
| 9,980,487 B2 | 5/2018 | Wada et al. |
| 10,104,891 B2 | 10/2018 | Wada et al. |
| 2001/0051620 A1 | 12/2001 | Berger et al. |
| 2002/0019531 A1 | 2/2002 | Kitazawa et al. |
| 2003/0039838 A1 | 2/2003 | Chen et al. |
| 2009/0298894 A1 | 12/2009 | Ohmori et al. |
| 2010/0137245 A1 | 6/2010 | Cristau et al. |
| 2010/0190828 A1 | 7/2010 | Cristau et al. |
| 2011/0046178 A1 | 2/2011 | Cristau et al. |
| 2011/0105429 A1 | 5/2011 | Cristau et al. |
| 2011/0224257 A1 | 9/2011 | Cristau et al. |
| 2011/0301197 A1 | 12/2011 | Cristau et al. |
| 2011/0306620 A1 | 12/2011 | Cristau et al. |
| 2011/0312999 A1 | 12/2011 | Cristau et al. |
| 2012/0065197 A1 | 3/2012 | Cristau et al. |
| 2012/0122928 A1 | 5/2012 | Tsuchiya et al. |
| 2012/0245204 A1 | 9/2012 | Hoffmann et al. |
| 2014/0005224 A1 | 1/2014 | Hillebrand et al. |
| 2014/0228404 A1 | 8/2014 | Hillebrand et al. |
| 2015/0024935 A1 | 1/2015 | Tsuchiya et al. |
| 2016/0251344 A1 | 9/2016 | Olenik et al. |
| 2017/0231226 A1 | 8/2017 | Wada et al. |

FOREIGN PATENT DOCUMENTS

| | | |
|---|---|---|
| CN | 1704404 A | 12/2005 |
| EP | 0238753 A1 | 9/1987 |
| EP | 0313288 A1 | 4/1989 |
| EP | 2423210 A1 | 2/2012 |
| EP | 3181563 A1 | 6/2017 |
| JP | 2001-302658 A | 10/2001 |
| JP | 2004-137255 A | 5/2004 |
| JP | 2008-529982 A | 8/2008 |
| JP | 2009-502948 A | 1/2009 |
| JP | 2010-516765 A | 5/2010 |
| JP | 2010-533716 A | 10/2010 |
| JP | 2011-021013 A | 2/2011 |
| JP | 2011-510925 A | 4/2011 |
| JP | 2012-512248 A | 5/2012 |

(Continued)

OTHER PUBLICATIONS

Machine Translation of WO 2009/131090, obtained from <https://worldwide.espacenet.com/>, Accessed Apr. 10, 2021.*
Supplementary European Search Report for Application No. 16889770. 0, dated Jul. 9, 2019, 12 pages.
Ahad et al., The Chemistry of Fungi. Part 77. The Synthesis of Benzophenones from Phthalides: X-Ray Crystallographic Definition of a Novel Isobenzofuran System. Journal of the Chemical Society, Perkin Transactions 1. 1980;11:2445-2449.
Anthony et al., Synthesis, optical, thermal, and redox properties of 2,3,9,10-tetrasubstituted- 6,13-dialkynylpentacenes. Proc of SPIE. 2005;5940:594002-1-594002-12.
Bhattacharjee et al., The Oxidation of a Series of Phthalyl Alcohols. J Heterocyclic Chem. 1980;17(2):315-320.
Chaikin et al., Reduction of Aldehydes, Ketones and Acid Chlorides by Sodium Borohydride. J Am Chem Soc. 1949;71(1):122-125.

(Continued)

*Primary Examiner* — Alicia L Otton

(74) *Attorney, Agent, or Firm* — Arent Fox LLP

(57) ABSTRACT

A process for preparing a compound represented by Formula [1], the process comprising a step of hydrolyzing a compound represented by Formula [2] under an acidic or basic condition, and a step of reacting a compound represented by Formula [3] with a metal acetate salt, and a step of halogenating a compound represented by Formula [4]; a process for preparing a compound represented by Formula [1] comprising a step of reacting a compound represented by Formula [3] with a metal acetate salt, and then, adding alcohol, water, or base to the reaction solution to perform reaction; a process for preparing a compound represented by Formula [1] comprising a step of reacting a compound represented by Formula [3] under a presence or absence of a base, an ionic liquid and a metal sulfate salt, in water or a mixed solvent of water and an organic solvent; a compound represented by Formula [2] or a salt of the same; and a compound represented by Formula [3] or a salt of the same.

21 Claims, No Drawings

(56) References Cited

FOREIGN PATENT DOCUMENTS

| | | |
|---|---|---|
| JP | 2013-544761 A | 12/2013 |
| JP | 2014-501246 A | 1/2014 |
| WO | 1993/09113 A1 | 5/1993 |
| WO | 01/47892 A1 | 7/2001 |
| WO | 2006/082001 A1 | 8/2006 |
| WO | 2007/014290 A2 | 2/2007 |
| WO | 2008/013622 A2 | 1/2008 |
| WO | 2008/013925 A2 | 1/2008 |
| WO | 2009/014637 A2 | 1/2008 |
| WO | 2008/091580 A2 | 7/2008 |
| WO | 2008/091594 A2 | 7/2008 |
| WO | 2009/055514 A2 | 4/2009 |
| WO | 2009/094407 A2 | 7/2009 |
| WO | 2009/094445 A2 | 7/2009 |
| WO | 2009/131090 A1 | 10/2009 |
| WO | 2009/132785 A1 | 11/2009 |
| WO | 2010/037479 A1 | 4/2010 |
| WO | 2010/065579 A2 | 6/2010 |
| WO | 2010/066353 A1 | 6/2010 |
| WO | 2010/077752 A1 | 7/2010 |
| WO | 2010/149275 A1 | 12/2010 |
| WO | 2011/018401 A1 | 2/2011 |
| WO | 2011/018415 A2 | 2/2011 |
| WO | 2011/051243 A1 | 5/2011 |
| WO | 2011/051244 A1 | 5/2011 |
| WO | 2011/076510 A1 | 6/2011 |
| WO | 2011/076699 A1 | 6/2011 |
| WO | 2011/085170 A1 | 7/2011 |
| WO | 2011/134969 A1 | 11/2011 |
| WO | 2011/144586 A1 | 11/2011 |
| WO | 2011/146182 A1 | 11/2011 |
| WO | 2011/147765 A1 | 12/2011 |
| WO | 2012/020060 A1 | 2/2012 |
| WO | 2012/025557 A1 | 3/2012 |
| WO | 2012/037411 A2 | 3/2012 |
| WO | 2012/045798 A1 | 4/2012 |
| WO | 2012/055837 A1 | 5/2012 |
| WO | 2012/069633 A1 | 5/2012 |
| WO | 2012/082580 A2 | 6/2012 |
| WO | 2012/104273 A1 | 8/2012 |
| WO | 2012/107475 A1 | 8/2012 |
| WO | 2012/107477 A1 | 8/2012 |
| WO | 2012/168188 A1 | 12/2012 |
| WO | 2013/000941 A1 | 1/2013 |
| WO | 2013/000943 A1 | 1/2013 |
| WO | 2013/037768 A1 | 3/2013 |
| WO | 2013/056911 A1 | 4/2013 |
| WO | 2013/056915 A1 | 4/2013 |
| WO | 2013/098229 A2 | 7/2013 |
| WO | 2013/116251 A2 | 8/2013 |
| WO | 2013/127704 A1 | 9/2013 |
| WO | 2013/127784 A1 | 9/2013 |
| WO | 2013/127789 A1 | 9/2013 |
| WO | 2013/127808 A1 | 9/2013 |
| WO | 2013/191866 A1 | 12/2013 |
| WO | 2014/060176 A1 | 4/2014 |
| WO | 2014/075873 A1 | 5/2014 |
| WO | 2014/075874 A1 | 5/2014 |
| WO | 2014/118142 A1 | 8/2014 |
| WO | 2014/118143 A1 | 8/2014 |
| WO | 2014/154530 A1 | 10/2014 |
| WO | 2014/179144 A1 | 11/2014 |
| WO | 2014/206896 A1 | 12/2014 |
| WO | 2015/036379 A1 | 3/2015 |
| WO | 2015/055574 A1 | 4/2015 |
| WO | 2015/067802 A1 | 5/2015 |
| WO | 2016/024350 A1 | 2/2016 |
| WO | 2016/024434 A1 | 2/2016 |
| WO | 2017/138068 A1 | 8/2017 |
| WO | 2017/138069 A1 | 8/2017 |

OTHER PUBLICATIONS

Chen et al., Chemoselective reduction and self-immolation based FRET probes for detecting hydrogen sulfide in solution and in cells. Org Biomol Chem. 2014;12:5629-5633. Includes Supporting Information.

Greene et al., Protection for the Hydroxyl Group, Including 1,2- and 1,3-Diols. Protective Groups in Organic Synthesis, Third Edition. John Wiley & Sons, Inc., pp. 17-21, 198 (1999).

Jansen et al., Molecular clips based on propanediurea. Exceptionally high binding affinities for resorcinol guests. J Org Chem. Apr. 20, 2001;66(8):2643-2653.

Kirmse et al., Carbenes and the O—H Bond: Hydroxyalkyl-Substituted Arylcarbenes. J Org Chem. 1990;55:2325-2332.

Kisin-Finfer et al., New repertoire of 'donor-two-acceptor' NIR fluorogenic dyes. Bioorganic & Medicinal Chemistry. Bioorganic & Medicinal Chemistry. 2013;21:3605-3608. Includes Supporting Information.

Meisenheimer et al., Proluciferin acetals as bioluminogenic substrates for cytochrome P450 activity and probes for CYP3A inhibition. Drug Metab Dispos. Dec. 2011;39(12):2403-10.

Nystrom et al., Reduction of Organic Compounds by Lithium Aluminum Hydride. I. Aldehydes, Ketones, Esters, Acid Chlorides and Acid Anhydrides. J Am Chem Soc. 1947;69(5):1197-1199.

Santoso et al., Exploring O-stannyl ketyl and acyl radical cyclizations for the synthesis of gamma-lactone-fused benzopyrans and benzofurans. Org Biomol Chem. Jan. 7, 2014;12(1):171-6.

Singh et al., Oxidative dearomatization and unusual intramolecular Diels-Alder reaction of cyclohexa-2,4-dienone: synthesis and photoreaction of oxa-tricyclo[5.2.2.01,5]undec-10-ene-8-ones. Tetrahedron Letters. Apr. 2015;56(15):1982-1985.

Suzuki et al., Synthesis and Absolute Configuration kof Pyriculol. Agri Biol Chem. 1987;51(4):1121-1127.

Supplementary European Search Report for Application No. 15832228. 9, dated Jan. 8, 2018. 5 pages.

International Search Report for Application No. PCT/JP2015/066841, dated Sep. 15, 2015. 6 pages.

International Search Report for Application No. PCT/JP2016/053650, dated Mar. 15, 2016. 2 pages.

International Search Report for Application No. PCT/JP2016/053654, dated Apr. 19, 2016. 3 pages.

Supplementary European Search Report for Application No. 16889771. 8, dated Aug. 12, 2019, 7 pages.

Masanobu, Suzuki, et al., Synthesis and absolute configuration of pyriculol, Agricultural and Biological Chemistry, vol. 51, No. 4, Dec. 31, 1987, pp. 1121-1127.

* cited by examiner

PROCESS FOR PREPARING 1,2-BENZENEDIMETHANOL COMPOUND

CROSS-REFERENCE TO RELATED APPLICATIONS

This application is a U.S. national stage filing, under 35 U.S.C. § 371(c), of International Application No. PCT/JP2016/053650, filed on Feb. 8, 2016. The entire contents of the aforementioned application are incorporated herein by reference.

TECHNICAL FIELD

The present invention relates to a process for preparing 1,2-benzenedimethanol compound.

BACKGROUND ART

A process for preparing 1,2-benzenedimethanol compound that have been reported to date include: a method of reacting phthalic acid, phthalic anhydride or phthalide with strong reductants, such as lithium aluminum hydride, borane, or sodium borohydride; and a method of treating 1,2-bishalomethylbenzene in a basic aqueous solution (NPL1 to NPL3). However, an industrial production of the compound by the former method is disadvantageous in that it requires treatment of secondary aluminum compound products as well as performing production under a water-prohibiting condition, and an industrial production of the compound by the latter method is disadvantageous in that it frequently leads to undesired decomposition of functional groups and generation of an untargeted secondary product, phthalan. A more efficient improvement was thus awaited from the perspective of operability, economics, safety and acceptability of functional groups.

CITATION LIST

Non-Patent Literature

NPL1: *J. Am. Chem. Soc.* 1947, 69, 1197.
NPL2: *J. Am. Chem. Soc.* 1949, 71, 122.
NPL3: *J. Org. Chem.* 1990, 55, 2325.

SUMMARY OF INVENTION

Technical Problem

The object of the present invention is to provide a process for efficiently preparing a 1,2-benzenedimethanol compound constituting a synthetic intermediate of a piperidine derivative, which is effective as a fungicidal crop protectant.

Solution to Problem

The present inventors carried out extensive studies to solve the above problem and found a process for efficiently preparing a 1,2-benzenedimethanol compound represented by Formula [1], and completed the present invention based on the finding.

The present invention encompasses the following preparation processes of compounds.

(1) A process for preparing a compound represented by Formula [1]:

[Chemical Formula 1]

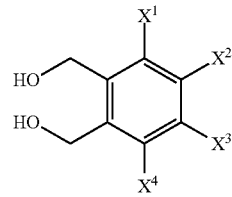

[1]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —$OS(O)_2R^1$;

at least one of $X^1$, $X^2$, $X^3$ and $X^4$ is —$OS(O)_2R^1$; and $R^1$ is $C_1$-$C_8$ alkyl, $C_1$-$C_8$ haloalkyl or $C_3$-$C_6$ cycloalkyl the process comprising:

a step of hydrolyzing a compound represented by Formula [2] under an acidic or basic condition:

[Chemical Formula 2]

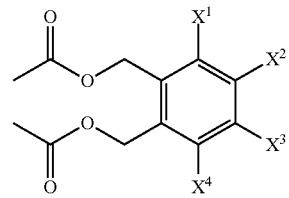

[2]

wherein, $X^1$, $X^2$, $X^3$ and $X^4$ are as defined for Formula [1].

(2) The process according to (1), wherein the basic condition is provided by a metal carbonate salt.

(3) The process according to either (1) or (2), further comprising a step of reacting a compound represented by Formula [3] with a metal acetate salt:

[Chemical Formula 3]

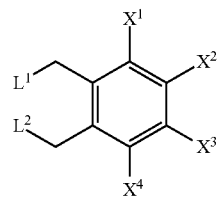

[3]

wherein, $X^1$, $X^2$, $X^3$ and $X^4$ are as defined in (1); and $L^1$ and $L^2$ are each independently a halogen atom to prepare the compound represented by Formula [2].

(4) The process for preparing a compound represented by Formula [2]:

[Chemical Formula 4]

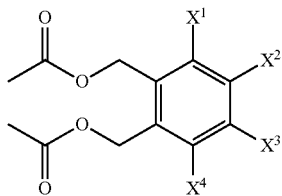

[2]

wherein, $X^1$, $X^2$, $X^3$ and $X^4$ are as defined in (1)
the process comprising:
a step of reacting a compound represented by Formula [3] with a metal acetate salt:

[Chemical Formula 5]

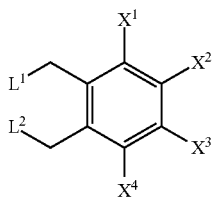

[3]

wherein, $X^1$, $X^2$, $X^3$ and $X^4$ are as defined in (1); and $L^1$ and $L^2$ are each independently a halogen atom.

(5) The process according to any one of (1) to (4), further comprising a step of halogenating a compound represented by Formula [4]:

[Chemical Formula 6]

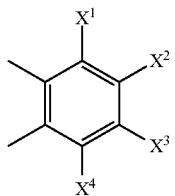

[4]

wherein, $X^1$, $X^2$, $X^3$ and $X^4$ are as defined in (1) to prepare the compound represented by Formula [3].

(6) A process for preparing a compound represented by Formula [3]:

[Chemical Formula 7]

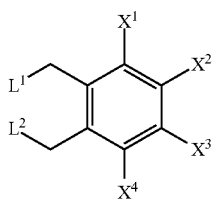

[3]

wherein, $X^1$, $X^2$, $X^3$ and $X^4$ are as defined in (1); and $L^1$ and $L^2$ are each independently a halogen atom
the process comprising:

a step of halogenating a compound represented by Formula [4]:

[Chemical Formula 8]

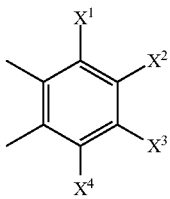

[4]

wherein, $X^1$, $X^2$, $X^3$ and $X^4$ are as defined in (1).

(7) The process according to (5) or (6), wherein a halogenation reagent for the halogenation reaction is a chlorination reagent such as chlorine, sulfuryl chloride, N-chlorosuccinimide, or a bromination reagent such as bromine, N-bromosuccinimide.

(8) The process according to any one of (1) to (3) comprising a step of reacting the compound represented by Formula [3] with a metal acetate salt to obtain the compound represented by Formula [2], and hydrolyzing the compound represented by Formula [2] without isolating the compound represented by Formula [2] under a basic condition to obtain the compound represented by Formula [1].

(9) A process for preparing a compound represented by Formula [1]:

[Chemical Formula 9]

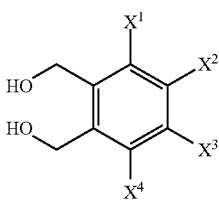

[1]

wherein, $X^1$, $X^2$, $X^3$ and $X^4$ are as defined in (1)
the process comprising:
a step of reacting a compound represented by Formula [3] under a presence or absence of a base, an ionic liquid and a metal sulfate salt, in water or a mixed solvent of water and an organic solvent:

[Chemical Formula 10]

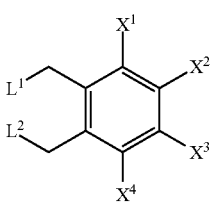

[3]

wherein $X^1$, $X^2$, $X^3$ and $X^4$ are as defined in (1); and $L^1$ and $L^2$ are as defined in (3).

(10) The process according to (9) wherein the reaction condition is provided by a step of performing a reaction in water or a mixed solvent of water and organic solvent under a presence of a base or a metal sulfate salt.

(11) The process according to (9) wherein the reaction condition is provided by a step of performing a reaction in water or a mixed solvent of water and organic solvent.

(12) The process according to any one of (1) to (11), wherein $X^1$ is $-OS(O)_2R^1$; and $X^2$, $X^3$ and $X^4$ are each independently a hydrogen atom, nitro, a halogen atom, difluoromethoxy or $-OS(O)_2Me$.

(13) The process according to (12),
wherein $X^1$ is $-OS(O)_2Me$, $-OS(O)_2Et$, $-OS(O)_2n$-Pr, $-OS(O)_2i$-Pr, $-OS(O)_2c$-Pr, $-OS(O)_2n$-Bu, $-OS(O)_2n$-$C_8H_{17}$, $-OS(O)_2CH_2CH_2CF_3$;

$X^2$ and $X^3$ are hydrogen atoms; and $X^4$ is a hydrogen atom, nitro, a halogen atom, difluoromethoxy or $-OS(O)_2Me$.

(14) The process according to (13),
wherein $X^1$ is $-OS(O)_2Me$; and
$X^4$ is a hydrogen atom or a fluorine atom.

(15) The process according to any one of (3) to (11), wherein $X^1$ is $-OS(O)_2R^1$;
$X^2$, $X^3$ and $X^4$ are each independently a hydrogen atom, nitro, a halogen atom, difluoromethoxy or $-OS(O)_2Me$; and
$L^1$ and $L^2$ are each independently a chlorine atom or a bromine atom.

(16) The process according to (15),
wherein $X^1$ is $-OS(O)_2Me$, $-OS(O)_2Et$, $-OS(O)_2n$-Pr, $-OS(O)_2i$-Pr, $-OS(O)_2c$-Pr, $-OS(O)_2n$-Bu, $-OS(O)_2n$-$C_8H_{17}$, $-OS(O)_2CH_2CH_2CF_3$;

$X^2$ and $X^3$ are hydrogen atoms;

$X^4$ is a hydrogen atom, nitro, a halogen atom, difluoromethoxy or $-OS(O)_2Me$; and $L^1$ and $L^2$ are bromine atoms.

(17) The process according to (16),
wherein $X^1$ is $-OS(O)_2Me$; and
$X^4$ is a hydrogen atom or a fluorine atom.

(18) The process according to any one of (1) to (11), wherein $X^1$, $X^3$ and $X^4$ are hydrogen atoms;
$X^2$ is $-OS(O)_2R^1$; and
$R^1$ is $C_1$-$C_4$ alkyl.

(19) The process according to (18),
wherein $X^2$ is $-OS(O)_2Me$.

(20) The process according to any one of (3) to (11), wherein $X^1$, $X^3$ and $X^4$ are hydrogen atoms;
$X^2$ is $-OS(O)_2R^1$;
$R^1$ is $C_1$-$C_4$ alkyl; and
$L^1$ and $L^2$ are each independently a chlorine atom or a bromine atom.

(21) The process according to (20),
wherein $X^2$ is $-OS(O)_2Me$; and
$L^1$ and $L^2$ are bromine atoms.

(22) A compound represented by Formula [2] or a salt thereof:

[Chemical Formula 11]

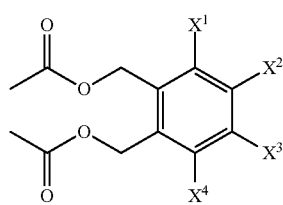

[2]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or $-OS(O)_2R^1$;
at least one of $X^1$, $X^2$, $X^3$ and $X^4$ is $-OS(O)_2R^1$; and
$R^1$ is $C_1$-$C_8$ alkyl, $C_1$-$C_8$ haloalkyl or $C_3$-$C_6$ cycloalkyl.

(23) The compound or a salt thereof according to (22),
wherein $X^1$ is $-OS(O)_2Me$, $-OS(O)_2Et$, $-OS(O)_2n$-Pr, $-OS(O)_2i$-Pr, $-OS(O)_2c$-Pr, $-OS(O)_2n$-Bu, $-OS(O)_2n$-$C_8H_{17}$, $-OS(O)_2CH_2CH_2CF_3$;

$X^2$ and $X^3$ are hydrogen atoms;

$X^4$ is a hydrogen atom, nitro, a halogen atom, a difluoromethoxy or $-OS(O)_2Me$.

(24) A compound represented by Formula [3] or a salt thereof:

[Chemical Formula 12]

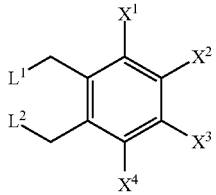

[3]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or $-OS(O)_2R^1$;
at least one of $X^1$, $X^2$, $X^3$ and $X^4$ is $-OS(O)_2R^1$;
$R^1$ is $C_1$-$C_8$ alkyl, $C_1$-$C_8$ haloalkyl or $C_3$-$C_6$ cycloalkyl; and
$L^1$ and $L^2$ are each independently a halogen atom.

(25) The compound or a salt thereof according to (24),
wherein $X^1$ is $-OS(O)_2Me$, $-OS(O)_2Et$, $-OS(O)_2n$-Pr, $-OS(O)_2i$-Pr, $-OS(O)_2c$-Pr, $-OS(O)_2n$-Bu, $-OS(O)_2n$-$C_8H_{17}$, $-OS(O)_2CH_2CH_2CF_3$;

$X^2$ and $X^3$ are hydrogen atoms;

$X^4$ is a hydrogen atom, nitro, a halogen atom, difluoromethoxy or $-OS(O)_2Me$; and $L^1$ and $L^2$ are bromine atoms.

(26) A process for preparing a compound represented by Formula [5]

[Chemical Formula 13]

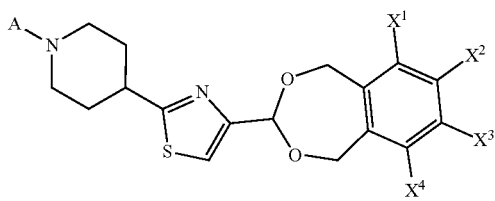

[5]

wherein, A is a group selected from:

[Chemical Formula 14]

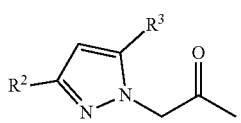

A-1

-continued

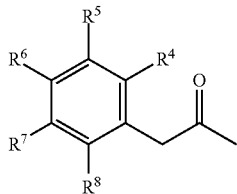
A-2 wherein, $R^2$ and $R^3$ are each independently $C_1$-$C_4$ alkyl, $C_1$-$C_4$ haloalkyl or a halogen atom;

$R^4$, $R^5$, $R^6$, $R^7$ and $R^8$ are each independently a hydrogen atom, a halogen atom, cyano, hydroxy, amino, nitro, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_1$-$C_6$ alkoxy, $C_1$-$C_6$ haloalkoxy, $C_3$-$C_6$ cycloalkyl, $C_3$-$C_6$ halocycloalkyl, $C_4$-$C_{10}$ cycloalkylalkyl, $C_4$-$C_{10}$ alkylcycloalkyl, $C_5$-$C_{10}$ alkylcycloalkylalkyl, $C_2$-$C_6$ alkoxyalkyl, $C_1$-$C_6$ hydroxyalkyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_8$ dialkylamino, $C_3$-$C_6$ cycloalkylamino, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl, $C_2$-$C_6$ alkylcarbonyloxy, $C_2$-$C_6$ alkylcarbonylthio, $C_2$-$C_6$ alkylaminocarbonyl, $C_2$-$C_8$(dialkylamino)carbonyl, or $C_3$-$C_6$ trialkylsilyl;

$X^1$, $X^2$, $X^3$ and $X^4$ are as defined in (1), the process comprising:

a step of reacting a compound represented by Formula [6]:

[Chemical Formula 15]

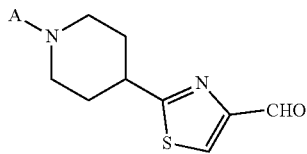
[6]

wherein, A is as defined by Formula [5], with a compound represented by Formula [1]:

[Chemical Formula 16]

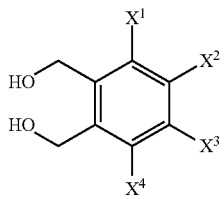
[1]

wherein, $X^1$, $X^2$, $X^3$ and $X^4$ are as defined in (1), and the compound of Formula [1] is prepared by a step according to any one of (1), (3), (5), (8) and (9).

(27) The process according to (26), wherein $R^4$, $R^6$ and $R^7$ are hydrogen atoms; and $R^5$ and $R^8$ are each independently a hydrogen atom, a halogen atom, $C_1$-$C_6$ alkyl or $C_1$-$C_6$ haloalkyl.

(28) The process according to (26) or (27), wherein $R^2$ is trifluoromethyl, difluoromethyl or a chlorine atom;

$R^3$ is methyl, trifluoromethyl, difluoromethyl or a chlorine atom;

$R^5$ and $R^8$ are each independently a hydrogen atom, a chlorine atom, trifluoromethyl or methyl.

(29) The process according to any one of (26) to (28), wherein A is A-1.

(30) The process according to any one of (26) to (29), wherein A is [5-methyl-3-(trifluoromethyl)-1H-pyrazol-1-yl]acetyl or [3,5-bis(difluoromethyl)-1H-pyrazol-1-yl]acetyl.

(31) The process according to (26), wherein $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —OS(O)$_2$R$^1$;

at least one of $X^1$, $X^2$, $X^3$ and $X^4$ is —OS(O)$_2$R$^1$;

$R^1$ is $C_1$-$C_8$ alkyl, $C_1$-$C_8$ haloalkyl or $C_3$-$C_6$ cycloalkyl.

(32) The process according to (26) or (31), wherein $X^1$ is —OS(O)$_2$R$^1$; and $X^2$, $X^3$ and $X^4$ are each independently a hydrogen atom, nitro, a halogen atom, difluoromethoxy or —OS(O)$_2$Me.

(33) The process according to any one of (26), (31) and (32), wherein $X^1$ is —OS(O)$_2$Me, —OS(O)$_2$Et, —OS(O)$_2$n-Pr, —OS(O)$_2$i-Pr, —OS(O)$_2$c-Pr, —OS(O)$_2$n-Bu, —OS(O)$_2$n-C$_8$H$_{17}$, —OS(O)$_2$CH$_2$CH$_2$CF$_3$;

$X^2$ and $X^3$ are hydrogen atoms; and $X^4$ is a hydrogen atom, nitro, a halogen atom, difluoromethoxy or —OS(O)$_2$Me.

(34) The process according to any one of (26), and (31) to (33), wherein $X^1$ is —OS(O)$_2$Me; and $X^4$ is a hydrogen atom or a fluorine atom.

(35) The process according to (26), wherein $X^1$, $X^3$ and $X^4$ are hydrogen atoms;

$X^2$ is —OS(O)$_2$R$^1$; and $R^1$ is $C_1$-$C_4$ alkyl.

(36) The process according to (26) or (35), wherein $X^2$ is —OS(O)$_2$Me.

(37) The process according to any one of (31) to (36), wherein A is A-1.

(38) The process according to any one of (26) to (36), wherein the compound represented by Formula [5] is selected from:

4-[4-(6-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-ethylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(7-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-cyclopropylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-methyl-9-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-butylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-propylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-octylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-methoxy-9-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-iospropylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(7-ethylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-[6-(1,1,1-trifluoropropan-3-yl)sulfonyloxy-1,5-dihydro-3H-2,4-benzodioxepin-3-yl]-2-thiazolyl]-1-[2-[5-methyl-3-(trifluoromethyl)-1H-pyrazol-1-yl]acetyl]piperidine, 4-[4-(6-methylsulfonyloxy-9-nitro-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-methyl-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(7-fluoro-6-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-isopropylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-butylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-octylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6,7-dimethyl-9-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-chloro-9-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-bromo-9-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-(6-isopropylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-butylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-iodo-9-methylsulfonyloxy-1,5-dihydro-3H-2,4-benzodioxepin-3-yl)-2-thiazolyl]-1-[2-[5-methyl-3-(trifluoromethyl)-1H-pyrazol-1-yl]acetyl]piperidine, 4-[4-[6,9-bis(methylsulfonyloxy)-1,5-dihydro-3H-2,4-benzodioxepin-3-yl]-2-thiazolyl]-1-[2-[5-methyl-3-(trifluoromethyl)-1H-pyrazol-1-yl]acetyl]piperidine, 4-[4-(6-methylsulfonyloxy-1,5-dihydro-3H-2,4-benzodioxepin-3-yl)-2-thiazolyl]-1-[2-(3,5-dimethyl-1H-pyrazol-1-yl)acetyl]piperidine, 4-[4-(6-methoxy-9-methylsulfonyloxy-1,5-dihydro-3H-2,4-benzodioxepin-3-yl)-2-thiazolyl]-1-[2-[5-chloro-3-(trifluoromethyl)-1H-pyrazol-1-yl]acetyl]piperidine, 4-[4-(6-methoxy-9-methylsulfonyloxy-1,5-dihydro-3H-2,4-benzodioxepin-3-yl)-2-thiazolyl]-1-[2-(3,5-dichloro-1H-pyrazol-1-yl)acetyl]piperidine, 4-[4-(6-methoxy-9-methylsulfonyloxy-1,5-dihydro-3H-2,4-benzodioxepin-3-yl)-2-thiazolyl]-1-[2-(3,5-dimethyl-1H-pyrazol-1-yl)acetyl]piperidine, 4-[4-(6-chloro-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-methoxy-9-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-chloro-9-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-methylsulfonyloxy-1,5-dihydro-3H-2,4-benzodioxepin-3-yl)-2-thiazolyl]-1-[2-[3,5-bis(dichloromethyl)-1H-pyrazol-1-yl]acetyl]piperidine, 4-[4-(6-fluoro-9-methylsulfonyloxy-1,5-dihydro-3H-2,4-benzodioxepin-3-yl)-2-thiazolyl]-1-[2-(3,5-dimethyl-1H-pyrazol-1-yl)acetyl]piperidine, 4-[4-(6,7-dimethyl-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6,7-dimethyl-9-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-bromo-9-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-methylsulfonyloxy-9-nitro-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-bromo-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(6-methylsulfonyloxy-9-nitro-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-iodo-9-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(6-iodo-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(7-fluoro-6-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-(7-fluoro-6-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(7-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine, 4-[4-(7-methylsulfonyloxy-1,5-dihydro-3H-2,4-benzodioxepin-3-yl)-2-thiazolyl]-1-[2-[3,5-bis(trifluoromethyl)-1H-pyrazol-1-yl]acetyl]piperidine, 4-[4-[6-(difluoromethoxy)-9-methylsulfonyloxy-1,5-dihydro-3H-2,4-benzodioxepin-3-yl]-2-thiazolyl]-1-[2-[5-methyl-3-(trifluoromethyl)-1H-pyrazol-1-yl]acetyl]piperidine, 4-[4-[6,9-bis(methylsulfonyloxy)-1,5-dihydro-3H-2,4-benzodioxepin-3-yl]-2-thiazolyl]-1-[2-[3,5-bis(difluoromethyl)-1H-pyrazol-1-yl]acetyl]piperidine, 4-[4-[6,9-bis(methylsulfonyloxy)-1,5-dihydro-3H-2,4-benzodioxepin-3-yl]-2-thiazolyl]-1-[2-[3,5-bis(trifluoromethyl)-1H-pyrazol-1-yl]acetyl]piperidine, 4-[4-(6-fluoro-9-methylsulfonyloxy-1,5-dihydro-3H-2,4-benzodioxepin-3-yl)-2-thiazolyl]-1-[2-[5-methyl-3-(difluoromethyl)-1H-pyrazol-1-yl]acetyl]piperidine, 4-[4-(6-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-fluoro-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-butylsulfonyloxy-1,5-dihydro-3H-2,4-benzodioxepin-3-yl)-2-thiazolyl]-1-[2-(2,5-dimethylphenyl)acetyl]piperidine, 4-[4-(6-fluoro-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-methoxy-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-methoxy-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-methylsulfonyloxy-1,5-dihydro-3H-2,4-benzodioxepin-3-yl)-2-thiazolyl]-1-[2-[2,5-bis(trifluoromethyl)phenyl]acetyl]piperidine, 4-[4-(6,7-dimethyl-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6,7-dimethyl-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-bromo-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-methylsulfonyloxy-9-nitro-1,5-dihydro-3H-2,4-benzodioxepin-3-yl)-2-thiazolyl]-1-[2-(2,5-dichlorophenyl)acetyl]piperidine, 4-[4-(6-bromo-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-methylsulfonyloxy-9-nitro-1,5-dihydro-3H-2,4-benzodioxepin-3-yl)-2-thiazolyl]-1-[2-(2,5-dimethylphenyl)acetyl]piperidine, 4-[4-(6-chloro-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-iodo-9-methylsulfonyloxy-1,5-dihydro-3H-2,4-benzodioxepin-3-yl)-2-thiazolyl]-1-[2-(2,5-dimethylphenyl)acetyl]piperidine, 4-[4-(6-chloro-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(7-fluoro-6-methylsulfonyloxy-1,5-dihydro-3H-2,4-benzodioxepin-3-yl)-2-thiazolyl]-1-[2-(2,5-dimethylphenyl)acetyl]piperidine, 4-[4-(7-fluoro-6-methylsulfonyloxy-1,5-dihydro-3H-2,4-benzodioxepin-3-yl)-2-thiazolyl]-1-[2-(2,5-dichlorophenyl)acetyl]piperidine, 4-[4-(6-iodo-9-methylsulfonyloxy-1,5-dihydro-3H-2,4-benzodioxepin-3-yl)-2-thiazolyl]-1-[2-(2,5-dichlorophenyl)acetyl]piperidine, 4-[4-(7-methylsulfonyloxy-1,5-dihydro-3H-2,4-benzodioxepin-3-yl)-2-thiazolyl]-1-[2-(2,5-dichlorophenyl)acetyl]piperidine, and 4-[4-[6,9-bis(methylsulfonyloxy)-1,5-dihydro-3H-2,4-benzodioxepin-3-yl]-2-thiazolyl]-1-[2-(2,5-dimethylphenyl)acetyl]piperidine.

DESCRIPTION OF EMBODIMENTS

The present invention is described in detail below.

Formula [1] provides a general definition of a 1,2-benzenedimethanol compound that may be prepared by the present invention. A preferable definition of the groups associated with the formulae shown above and below are provided hereafter. The definition is applied to the final product represented by Formula [1], and also to all intermediates.

Preferably, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —OS(O)$_2$R$^1$; preferably, at least one of $X^1$, $X^2$, $X^3$ and $X^4$ is —OS(O)$_2$R$^1$, more preferably, $X^1$ is —OS(O)$_2$R$^1$, and more preferably, $X^2$, $X^3$ and $X^4$ are each independently a hydrogen atom, nitro, a halogen atom, difluoromethoxy or —OS(O)$_2$Me; $X^1$ is particularly preferably —OS(O)$_2$Me, —OS(O)$_2$Et, —OS(O)$_2$n-Pr, —OS(O)$_2$i-Pr, —OS(O)$_2$c-Pr, —OS(O)$_2$n-Bu, —OS(O)$_2$n-C$_8$H$_{17}$, —OS(O)$_2$CH$_2$CH$_2$CF$_3$, $X^2$ and $X^3$ are particularly preferably hydrogen atoms, in particular, $X^4$ is preferably a hydrogen atom, nitro, a halogen atom, difluoromethoxy or —OS(O)$_2$Me, most preferably, $X^1$ is —OS(O)$_2$Me, and most preferably, $X^4$ is a hydrogen atom, or a fluorine atom.

$R^1$ is preferably $C_1$-$C_8$ alkyl, $C_1$-$C_8$ haloalkyl or $C_3$-$C_6$ cycloalkyl, and more preferably methyl.

$L^1$ and $L^2$ are each independently, preferably, a halogen atom, more preferably, a chlorine atom or a bromine atom, and in particular, preferably a bromine atom.

A is preferably A-1.

$R^2$ and $R^3$ are each independently, preferably, $C_1$-$C_6$ alkyl, $C_1$-$C_6$ haloalkyl or a halogen atom, more preferably, methyl, trifluoromethyl, difluoromethyl or a chlorine atom.

$R^4$, $R^6$ and $R^7$ are preferably hydrogen atoms.

$R^5$ and $R^8$ are each independently, preferably, a hydrogen atom, a halogen atom, $C_1$-$C_6$ alkyl or $C_1$-$C_6$ haloalkyl, more preferably, a hydrogen atom, a chlorine atom, trifluoromethyl or methyl.

The aforementioned definition and explanation concerning the groups may be combined with each other in the general range or the preferable range as necessary. That is, each range may be combined with the preferable range. This rule is applied to both the final product and the corresponding precursor and intermediate.

One preferable aspect is a compound represented by Formula [1] (wherein, at least one of $X^1$, $X^2$, $X^3$ and $X^4$ is —OS(O)$_2$Me).

Another preferable aspect is a compound represented by Formula [1] (wherein, $X^1$ is —OS(O)$_2$Me, and $X^2$, $X^3$ and $X^4$ are hydrogen atoms).

Another preferable aspect is a compound represented by Formula [1] (wherein, $X^1$ is —OS(O)$_2$Et, and $X^2$, $X^3$ and $X^4$ are hydrogen atoms).

Another preferable aspect is a compound represented by Formula [1] (wherein, $X^1$ is —OS(O)$_2$n-Pr, and $X^2$, $X^3$ and $X^4$ are hydrogen atoms).

Another preferable aspect is a compound represented by Formula [1] (wherein, $X^1$ is —OS(O)$_2$i-Pr, and $X^2$, $X^3$ and $X^4$ are hydrogen atoms).

Another preferable aspect is a compound represented by Formula [1] (wherein, $X^1$ is —OS(O)$_2$c-Pr, and $X^2$, $X^3$ and $X^4$ are hydrogen atoms).

Another preferable aspect is a compound represented by Formula [1] (wherein, $X^1$ is —OS(O)$_2$n-Bu, and $X^2$, $X^3$ and $X^4$ are hydrogen atoms).

Another preferable aspect is a compound represented by Formula [1] (wherein, $X^1$ is —OS(O)$_2$n-C$_8$H$_{17}$, and $X^2$, $X^3$ and $X^4$ are hydrogen atoms).

Another preferable aspect is a compound represented by Formula [1] (wherein, $X^1$ is —OS(O)$_2$CH$_2$CH$_2$CF$_3$, and $X^2$, $X^3$ and $X^4$ are hydrogen atoms).

Another preferable aspect is a compound represented by Formula [1] (wherein, $X^1$ is —OS(O)$_2$Me, $X^2$ and $X^3$ are hydrogen atoms, and $X^4$ is nitro).

Another preferable aspect is a compound represented by Formula [1] (wherein, $X^1$ is —OS(O)$_2$Me, $X^2$ and $X^3$ are hydrogen atoms, and $X^4$ is a fluorine atom).

Another preferable aspect is a compound represented by Formula [1] (wherein, $X^1$ is —OS(O)$_2$Me, $X^2$ and $X^3$ are hydrogen atoms, and $X^4$ is a chlorine atom).

Another preferable aspect is a compound represented by Formula [1] (wherein, $X^1$ is —OS(O)$_2$Me, $X^2$ and $X^3$ are hydrogen atoms, and $X^4$ is a bromine atom).

Another preferable aspect is a compound represented by Formula [1] (wherein, $X^1$ is —OS(O)$_2$Me, $X^2$ and $X^3$ are hydrogen atoms, and $X^4$ is an iodine atom).

Another preferable aspect is a compound represented by Formula [1] (wherein, $X^1$ is —OS(O)$_2$Me, $X^2$ and $X^3$ are hydrogen atoms, and $X^4$ is difluoromethoxy).

Another preferable aspect is a compound represented by Formula [1] (wherein, $X^1$ and $X^4$ are —OS(O)$_2$Me, and $X^2$ and $X^3$ are hydrogen atoms).

Another preferable aspect is a compound represented by Formula [1] (wherein, $X^1$, $X^3$ and $X^4$ are hydrogen atoms, and $X^2$ is —OS(O)$_2$Me).

One preferable aspect is a compound represented by Formula [5] (wherein, A is 2-[5-methyl-3-(trifluoromethyl)-1H-pyrazol-1-yl]acetyl).

Another preferable aspect is a compound represented by Formula [5] (wherein, A is 2-[3,5-bis(trifluoromethyl)-1H-pyrazol-1-yl]acetyl).

Another preferable aspect is a compound represented by Formula [5] (wherein, A is 2-[3,5-bis(difluoromethyl)-1H-pyrazol-1-yl]acetyl).

Another preferable aspect is a compound represented by Formula [5] (wherein, A is 2-(3,5-dimethyl-1H-pyrazol-1-yl)acetyl).

Another preferable aspect is a compound represented by Formula [5] (wherein, A is 2-(2,5-dimethylphenyl)acetyl).

Another preferable aspect is a compound represented by Formula [5] (wherein, A is 2-(2,5-difluorophenyl)acetyl).

Another preferable aspect is a compound represented by Formula [5] (wherein, A is 2-(2,5-dichlorophenyl)acetyl).

Another preferable aspect is a compound represented by Formula [5] (wherein, A is 2-(2,5-dibromophenyl)acetyl).

Another preferable aspect is a compound represented by Formula [5] (wherein, A is 2-[2,5-bis(trifluoromethyl)phenyl]acetyl).

Another preferable aspect is a compound represented by Formula [5] (wherein, A is 2-(5-bromo-2-methylphenyl)acetyl).

Another preferable aspect is a compound represented by Formula [5] (wherein, A is 2-[2-methyl-5-(trifluoromethyl)phenyl]acetyl).

Another preferable aspect is a compound represented by Formula [5] (wherein, A is 2-[2-fluoro-5-(trifluoromethyl)phenyl]acetyl).

Another preferable aspect is a compound represented by Formula [5] (wherein, A is 2-[2-chloro-5-(trifluoromethyl)phenyl]acetyl).

Another preferable aspect is a compound represented by Formula [5] (wherein, A is 2-[2-bromo-5-(trifluoromethyl)phenyl]acetyl).

Another preferable aspect is a compound represented by Formula [5] (wherein, at least one of $X^1$, $X^2$, $X^3$ and $X^4$ is —OS(O)$_2$Me).

Another preferable aspect is a compound represented by Formula [5] (wherein, $X^1$ is —OS(O)$_2$Me, and $X^2$, $X^3$ and $X^4$ are hydrogen atoms).

Another preferable aspect is a compound represented by Formula [5] (wherein, $X^1$ is —OS(O)$_2$Et, and $X^2$, $X^3$ and $X^4$ are hydrogen atoms).

Another preferable aspect is a compound represented by Formula [5] (wherein, $X^1$ is —OS(O)$_2$n-Pr, and $X^2$, $X^3$ and $X^4$ are hydrogen atoms).

Another preferable aspect is a compound represented by Formula [5] (wherein, $X^1$ is —OS(O)$_2$i-Pr, and $X^2$, $X^3$ and $X^4$ are hydrogen atoms).

Another preferable aspect is a compound represented by Formula [5] (wherein, $X^1$ is —OS(O)$_2$c-Pr, and $X^2$, $X^3$ and $X^4$ are hydrogen atoms).

Another preferable aspect is a compound represented by Formula [5] (wherein, $X^1$ is —OS(O)$_2$n-Bu, and $X^2$, $X^3$ and $X^4$ are hydrogen atoms).

Another preferable aspect is a compound represented by Formula [5] (wherein, $X^1$ is —OS(O)$_2$n-C$_8$H$_{17}$, and $X^2$, $X^3$ and $X^4$ are hydrogen atoms).

Another preferable aspect is a compound represented by Formula [5] (wherein, $X^1$ is —OS(O)$_2$CH$_2$CH$_2$CF$_3$, and $X^2$, $X^3$ and $X^4$ are hydrogen atoms).

Another preferable aspect is a compound represented by Formula [5] (wherein, $X^1$ is —OS(O)$_2$Me, $X^2$ and $X^3$ are hydrogen atoms, and $X^4$ is nitro).

Another preferable aspect is a compound represented by Formula [5] (wherein, $X^1$ is —OS(O)$_2$Me, $X^2$ and $X^3$ are hydrogen atoms, and $X^4$ is a fluorine atom).

Another preferable aspect is a compound represented by Formula [5] (wherein, $X^1$ is —OS(O)$_2$Me, $X^2$ and $X^3$ are hydrogen atoms, and $X^4$ is a chlorine atom).

Another preferable aspect is a compound represented by Formula [5] (wherein, $X^1$ is —OS(O)$_2$Me, $X^2$ and $X^3$ are hydrogen atoms, and $X^4$ is a bromine atom).

Another preferable aspect is a compound represented by Formula [5] (wherein, $X^1$ is —OS(O)$_2$Me, $X^2$ and $X^3$ are hydrogen atoms, and $X^4$ is an iodine atom).

Another preferable aspect is a compound represented by Formula [5] (wherein, $X^1$ is —OS(O)$_2$Me, $X^2$ and $X^3$ are hydrogen atoms, and $X^4$ is difluoromethoxy).

Another preferable aspect is a compound represented by Formula [5] (wherein, $X^1$ and $X^4$ are —OS(O)$_2$Me, and $X^2$ and $X^3$ are hydrogen atoms).

Another preferable aspect is a compound represented by Formula [5] (wherein, $X^1$, $X^3$ and $X^4$ are hydrogen atoms, and $X^2$ is —OS(O)$_2$Me).

The terms used in the present specification is explained below.

"Halogen atom" encompasses a fluorine atom, a chlorine atom, a bromine atom or an iodine atom.

The notation consisting of a chemical symbol and a subscript figure as exemplified by $C_1$-$C_6$ indicates that the number of the subject element in the group following said notation is in the range shown by the subscript figure. For example, the number of carbons in the given case is 1 to 6, and the number of carbons in $C_2$-$C_6$ is 2 to 6.

If a name of a composite substituent follows the notation consisting of a chemical symbol and a subscript figure, such as $C_1$-$C_6$, the notation shows that the number of the subject element in the entire composite substituent is in the range shown by the subscript figure. For example, in $C_2$-$C_6$ alkylcarbonyl, the number of carbons in the entire alkylcarbonyl is 2 to 6, including a propyl carbonyl group.

"Alkyl" means a straight chain or a branched chain alkyl with a number of carbons of 1 to 8, preferably 1 to 6, unless otherwise specified. Examples include groups such as methyl, ethyl, n-propyl, isobutyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, 1-ethyl-2-methylpropyl. This definition is applied to alkyl that constitutes a part of a composite substituent, such as haloalkyl, alkylthio, alkylcarbonyl. For example, in a composite substituent such as alkylcycloalkyl, which includes alkyl at the end, such specific section of the cycloalkyl may be independently mono-substituted or poly-substituted with the same or different alkyl. The same applies to a composite substituent with other groups at the end, examples of other groups including alkenyl, alkoxy, hydroxy, halogen.

"Cycloalkyl" means a cycloalkyl having a branched chain with a number of carbons of 3 to 8, preferably 3 to 6, unless otherwise specified. Examples include groups such as cyclopropyl, 1-methylcyclopropyl, 2-methylcyclopropyl, cyclobutyl, cyclopentyl, cyclohexyl, 4,4-dimethylcyclohexyl. This definition is applied to cycloalkyl that constitutes a part of a composite substituent, such as halocycloalkyl.

The term "halo" in "halo . . . " (e.g. "haloalkyl") encompasses fluorine, chlorine, bromine and iodine. The halo substitution indicated by the prefix "halo" encompasses a mono-substitution or a poly-substitution, preferably a mono-substitution, a di-substitution and a tri-substitution.

"Haloalkyl" is a straight chain or branched chain alkyl with a carbon number of 1 to 6, having a part or all of hydrogen atoms on the group substituted by a halogen atom, unless otherwise specified. Examples include groups such as fluoromethyl, chloromethyl, bromomethyl, iodomethyl, difluoromethyl, dichloromethyl, dibromomethyl, diiodomethyl, trifluoromethyl, trichloromethyl, tribromomethyl, triiodomethyl, 1-chloroethyl, 1-bromoethyl, 2-trifluoroethyl, 3-chloropropyl, 3-bromopropyl, 4-chlorobutyl, 4-bromobutyl, 4-trifluorobutyl, 5-chloropentyl, 6-chlorohexyl. This definition is applied to haloalkyl that constitutes a part of a composite substituent, such as haloalkylcarbonyl, unless defined otherwise.

"Akenyl" means a straight chain or a branched chain alkenyl with a carbon number of 2 to 6, unless otherwise specified. Examples include groups such as vinyl, 1-propenyl, 2-propenyl, isopropenyl, 3-butenyl, 1,3-butadienyl, 4-pentenyl, 5-hexenyl. This definition is applied to alkenyl that constitutes a part of a composite substituent, such as haloalkenyl, unless defined otherwise.

"Alkynyl" means a straight chain or a branched chain alkynyl with a carbon number of 2 to 6, unless otherwise specified. Examples include groups such as ethynyl, 1-propynyl, 2-propynyl, 3-butynyl, 1-methyl-3-propynyl, 4-pentynyl, 5-hexynyl. This definition is applied to alkynyl that constitutes a part of a composite substituent, such as haloalkynyl, unless defined otherwise.

"Alkoxy" means a straight chain or a branched chain alkoxy with a carbon number of 1 to 6, unless otherwise specified. Examples include groups such as methoxy, ethoxy, propoxy, isopropoxy, butoxy, isobutoxy, sec-butoxy, tert-butoxy, pentyloxy, hexyloxy. This definition is applied to alkoxy that constitutes a part of a composite substituent, such as haloalkoxy, alkoxycarbonyl, unless defined otherwise.

"Haloalkoxy" means a straight chain or a branched chain alkoxy with a carbon number of 1 to 6, substituted by one or more, preferably one to ten halogen atoms, unless otherwise specified. Examples include groups such as fluoromethoxy, chloromethoxy, bromomethoxy, iodomethoxy, difluoromethoxy, dichloromethoxy, dibromomethoxy, diiodomethoxy, trifluoromethoxy, trichloromethoxy, tribromomethoxy, triiodomethoxy, 1-chloroethoxy, 1-bromoethoxy, 2-trifluoroethoxy, 3-chloropropoxy, 3-bromopropoxy, 4-chlorobutoxy, 4-bromobutoxy, 4-trifluorobutoxy, 5-chloropentoxy, 6-chlorohexyloxy. This definition is applied to haloalkoxy that constitutes a part of a composite substituent, such as haloalkoxycarbonyl, unless defined otherwise.

"Alkylthio" means an (alkyl)-S-group with a carbon number of 1 to 6, in which the alkyl section is as indicated above, unless otherwise specified. Examples include groups such as methylthio, ethylthio, n-propylthio, isopropylthio. This definition is applied to alkylthio that constitutes a part of a composite substituent, such as haloalkylthio, unless defined otherwise.

"Alkylsulfinyl" means an (alkyl)-SO-group with a carbon number of 1 to 6, in which the alkyl section is as indicated above, unless otherwise specified. Examples include groups such as methylsulfinyl, ethylsulfinyl, n-propylsulfinyl, isopropylsulfinyl. This definition is applied to alkylsulfinyl that constitutes a part of a composite substituent, such as haloalkylsulfinyl, unless defined otherwise.

"Alkylsulfonyl" means an (alkyl)-$SO_2$-group with a carbon number of 1 to 6, in which the alkyl section is as indicated above, unless otherwise specified. Examples include groups such as methylsulfonyl, ethylsulfonyl, n-propylsulfonyl, isopropylsulfonyl. This definition is applied to alkylsulfonyl that constitutes a part of a composite substituent, such as haloalkylsulfonyl, unless defined otherwise.

"Hydroxyalkyl" means a straight chain or a branched chain alkyl group with a carbon number of 1 to 6, substituted by 1 to 5 hydroxy groups, unless otherwise specified. Examples include groups such hydroxymethyl, hydroxyethyl, hydroxypropyl or hydroxyisopropyl.

"Alkylcarbonyl" means an (alkyl) —C(=O)-group, in which the alkyl section is as indicated above, unless otherwise specified. Examples include groups such as formyl, acetyl, propionyl, butyryl, and pivaloyl. This definition is applied to alkylcarbonyl that constitutes a part of a composite substituent, such as haloalkylcarbonyl, unless defined otherwise.

"Alkylcarbonyloxy" means an (alkyl)-C(=O)O-group, in which the alkyl section is as indicated above, unless otherwise specified. Examples include groups such as methylcarbonyloxy, ethylcarbonyloxy, propylcarbonyloxy. This definition is applied to alkylcarbonyloxy that constitutes a part of a composite substituent, such as haloalkylcarbonyloxy, unless defined otherwise.

The acid used in the reaction associated with the present invention is a Bronsted acid, which releases proton in the reaction system, unless otherwise specified. Examples include inorganic acids such as hydrochloric acid, hydrobromic acid, sulfuric acid; and organic acids such as acetic acid, trifluoroacetic acid, p-toluenesulfonic acid, trifluoromethanesulfonic acid. "Lewis acid" used in a reaction of the present invention means a compound, other than the hydrogen ion, that acts as an electron pair receptor in a reaction system. Examples include zinc chloride, aluminum chloride, tin chloride, boron trichloride, boron trifluoride, trimethylsilyl trifluoromethanesulfonate.

The base used in the present invention is a compound which receives proton in the reaction system, or a compound which acts as an electron pair donor in the reaction system, unless otherwise specified. Examples include organic amines such as triethylamine, pyridine, 4-dimethylaminopyridine, N,N-dimethylaniline, 1,8-diazabicyclo [5,4,0]-7-undecen; metal carbonate salts such as sodium carbonate, potassium carbonate, magnesium carbonate, calcium carbonate; metal hydrogen carbonate salts such as sodium hydrogen carbonate, potassium hydrogen carbonate; and metal carboxylic acid salts represented by metal acetic acid salt such as sodium acetate, potassium acetate, calcium acetate, and magnesium acetate; metal alkoxides such as sodium methoxide, sodium ethoxide, sodium tert-butoxide, potassium methoxide, potassium tert-butoxide; metal hydroxides such as sodium hydroxide, potassium hydroxide, calcium hydroxide, magnesium hydroxide; and metal hydrides such as lithium hydride, sodium hydride, and calcium hydride.

Ionic liquids used in the reaction of the present invention include imidazolium salts such as 1-butyl-3-methylimidazolium tetrafluoroborate, 1-butyl-2,3-dimethylimidazolium tetrafluoroborate, 1-ethyl-3-methylimidazolium tetrafluoroborate, 1-hexyl-3-methylimidazolium tetrafluoroborate, 1-ethyl-3-methylimidazolium methanesulfonate, 1-butyl-3-methylimidazolium trifluoromethanesulfonate, 1-butyl-2,3-dimethylimidazolium trifluoromethanesulfonate, 1-ethyl-3-methylimidazolium trifluoromethanesulfonate, 1-hexyl-3-methylimidazolium trifluoromethanesulfonate; ammonium salts such as tetrabutylammonium fluoride, tetrabutylammonium chloride, tetrabutylammonium bromide, tetrabutylammonium iodide.

The following notations in the table in this specification shows corresponding groups shown below.

For example,
Me indicates a methyl group,
Et indicates an ethyl group,
n-Pr indicates a n-propyl group,
i-Pr indicates an isopropyl group,
c-Pr indicates acyclopropyl group,
n-Bu indicates a n-butyl group.

Typical preparation processes of the compound represented by Formula [1] is shown below, without being limited thereby.

<Preparation Process 1>

The compound represented by Formula [1] may be prepared by a process consisting of a reaction formula exemplified below.

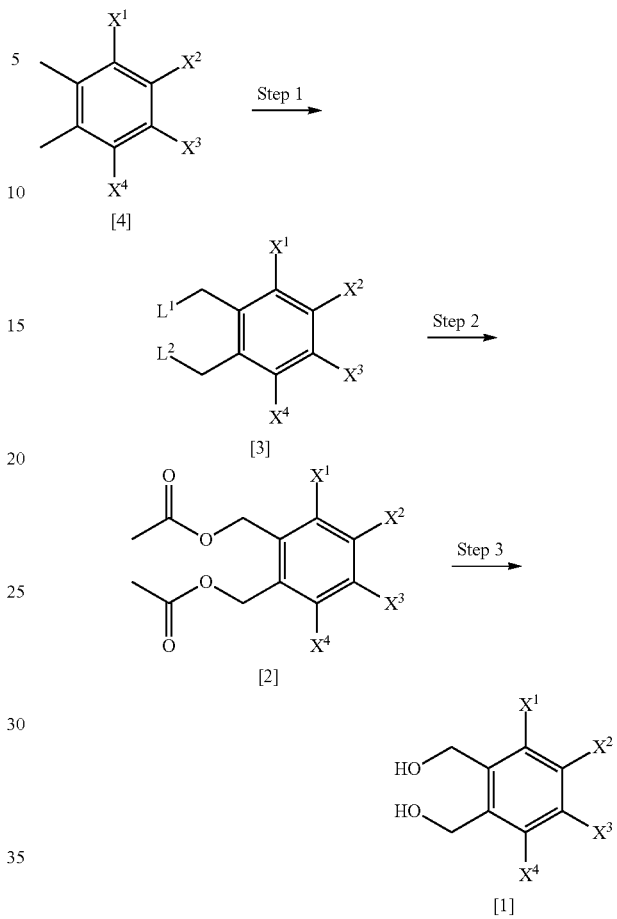

(wherein, $X^1$, $X^2$, $X^3$, $X^4$, $L^1$ and $L^2$ are each as defined in (1) and (3).)

(Step 1)

The compound of Formula [3] may be prepared by reacting the compound of Formula [4] in a solvent under the presence of a halogenating reagent.

The halogenating reagent that is applicable in this step includes chlorinating reagents such as chlorine, sulfuryl chloride, N-chlorosuccinimide; brominating reagents such as bromine and N-bromosuccinimide.

It is possible to irradiate light, or add a radical initiator such as azoisobutyronitrile, and benzoyl peroxide to initiate a radical reaction.

The amount of halogenating reagent used in this step may be selected appropriately from a range of from 2.0 to 10 mol, preferably from 2.0 to 3.0 mol, against 1 mol of the compound of Formula [4].

The solvent to be used in this step may be any solvent that does not inhibit the progress of the reaction. Examples include nitriles such as acetonitrile; ethers such as diethyl ether, diisopropyl ether, tetrahydrofuran, dioxane, Monoglyme, Diglyme; halogenated hydrocarbons such as dichloromethane, dichloroethane, chloroform, carbon tetrachloride, tetrachloroethane; aromatic hydrocarbons such as benzene, chlorobenzene, nitrobenzene, toluene; amides such as N,N-dimethylformamide, N,N-dimethylacetoamide; imidazolidinones such as 1,3-dimethyl-2-imidazolinone; sulfur compounds such as dimethylsulfoxide. A mixture of these solvents may also be used.

The amount of the solvent to be used may be selected appropriately from a range of from 0.01 to 100 L, preferably from 0.1 to 10 L, against 1 mol of the compound of Formula [4].

The reaction temperature may be selected from a range of from −20° C. to the boiling point range of the applied inert solvent, preferably from 0° C. to 100° C.

The reaction time is normally 10 min. to 48 h. although it differs by the reaction temperature, the reaction substrate, the reaction amount, etc.

The compound of Formula [3], which is the reaction target, may be collected from the reaction system by a common method after the reaction completes, and purified by operations such as the column chromatography or recrystallization, etc. as necessary.

Further, after the reaction completes, the compound of Formula [3] obtained by this step may be used in the reaction of Step 2 without being isolated or purified.

(Step 2)

The compound of Formula [2] may be prepared by reacting the compound represented by Formula [3] in a solvent under the presence of a metal acetate salt.

Examples of metal acetate salts used in this step include lithium acetate, sodium acetate and potassium acetate.

The amount of metal acetate salts to be used in this step may be selected from a range of from 2.0 to 10 mol, preferably from 2.0 to 3.0 mol against 1 mol of the compound of Formula [3].

The solvent to be used in this step includes a solvent as described in Step 1 of Preparation Process 1.

The amount of solvent to be used may be selected from a range of from 0.01 to 100 L, preferably 0.1 to 10 L against 1 mol of the compound of Formula [3].

The reaction temperature may be selected from a range of from −20° C. to the boiling point range of the applied inert solvent, preferably 0° C. to 100° C.

The reaction time is normally 10 min. to 48 h. although it differs by the reaction temperature, the reaction substrate, the reaction amount, etc.

The compound of Formula [2] obtained by this step may be collected from the reaction system by a common method, and purified by operations such as the column chromatography or recrystallization, etc. as necessary.

Further, after the reaction completes, the compound of Formula [2] obtained by this step may be used in the reaction of Step 3 without being isolated or purified.

(Step 3)

The compound of Formula [1] may be prepared by reacting the compound represented by Formula [2] in water and a solvent under the presence of acid, acid chloride or base.

The acid that may be used in this step includes inorganic acids such as hydrochloric acid, hydrobromic acid, sulfuric acid; and organic acids such as acetic acid, trifluoroacetic acid, p-toluenesulfonic acid, trifluoromethanesulfonic acid.

The amount of acid used may be selected appropriately from a range of from 0.1 to 10 mol, preferably from 0.1 to 5.0 mol, against 1 mol of the compound of Formula [2].

The acid chloride used in this step includes acetyl chloride, and benzoyl chloride.

The amount of acid chloride used may be selected appropriately from a range of from 0.1 to 10 mol, preferably from 0.1 to 5.0 mol, against 1 mol of the compound of Formula [2].

The base that may be used in this step includes organic amines such as triethylamine, pyridine, 4-dimethylaminopyridine, N,N-dimethylaniline, 1,8-diazabicyclo [5,4,0]-7-undecen; metal carbonate salts such as sodium carbonate, potassium carbonate, magnesium carbonate, calcium carbonate; metal hydrogen carbonate salts such as sodium hydrogen carbonate, potassium hydrogen carbonate; and metal carboxylic acid salts represented by metal acetic acid salt such as sodium acetate, potassium acetate, calcium acetate, and magnesium acetate; metal alkoxides such as sodium methoxide, sodium ethoxide, sodium tert-butoxide, potassium methoxide, potassium tert-butoxide; metal hydroxides such as sodium hydroxide, potassium hydroxide, calcium hydroxide, magnesium hydroxide; and metal hydrides such as lithium hydride, sodium hydride, and calcium hydride. Preferable among those are metal carbonate salts such as sodium carbonate, potassium carbonate, magnesium carbonate and calcium carbonate.

The amount of base used may be selected appropriately from a range of from 0.2 to 10 mol, preferably 0.2 to 5.0 mol against 1 mol of the compound of Formula [2].

The solvent to be used in this step includes water and a solvent as described in Step 1 of Preparation Process 1.

The amount of solvent used may be selected appropriately from a range of from 0.01 to 100 L, preferably 0.1 to 10 L against 1 mol of the compound of Formula [2].

The amount of water used may be selected appropriately from a range of from 0.01 to 100 L, preferably 0.1 to 10 L against 1 mol of the compound of Formula [2].

The reaction temperature may be selected from a range of from −20° C. to the boiling point range of the applied inert solvent, preferably 0° C. to 100° C.

The reaction time is normally 10 min. to 48 h. although it differs by the reaction temperature, the reaction substrate, the reaction amount, etc.

The compound of Formula [1], which is the reaction target, may be collected from the reaction system by a common method after the reaction completes, and purified by operations such as the column chromatography or recrystallization, etc. as necessary.

<Preparation Process 2>

The compound represented by Formula [1] may also be prepared by a process consisting of a reaction formula exemplified below.

[Chemical Formula 18]

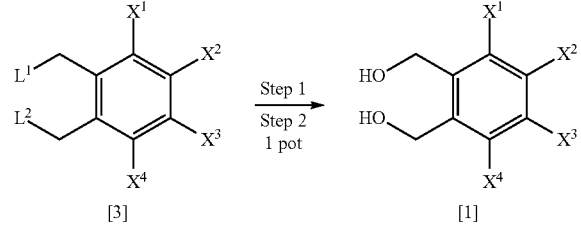

(wherein, $X^1$, $X^2$, $X^3$, $X^4$, $L^1$ and $L^2$ are each as defined in (1) and (3).)

The compound of Formula [1] may be prepared by reacting the compound represented by Formula [3] in a solvent under the presence of a metal acetate salt (Step 1), and then adding alcohol, water and base to the reaction solution of Step 1 to react them (Step 2).

(Step 1)

The metal acetate salts that may be used in this step includes those as described in Step 2 of Preparation Process 1.

The amount of metal acetate salt used in this step may be appropriately selected from a range of 2.0 to 10 mol, preferably 2.0 to 3.0 mol, against 1 mol of the compound of Formula [3].

The solvent to be used in this step includes a solvent as described in Step 1 of Preparation Process 1.

The amount of solvent to be used may be appropriately selected from a range of from 0.01 to 100 L, preferably 0.1 to 10 L against 1 mol of the compound of Formula [3].

The reaction temperature may be selected from a range of from −20° C. to the boiling point range of the applied inert solvent, preferably 0° C. to 100° C.

The reaction time is normally 10 min. to 48 h. although it differs by the reaction temperature, the reaction substrate, the reaction amount, etc.

(Step 2)

The compound of Formula [1] may be prepared by adding alcohol, water and base to the reaction solution of Step 1 of Preparation Process 2 to react them.

The alcohol to be used in this step includes, for example, methanol or ethanol.

The amount of alcohol to be used may be appropriately selected from a range of 0.01 to 100 L, preferably 0.1 to 10 L against 1 mol of the compound of Formula [3].

The amount of water to be used may be appropriately selected from a range of 0.01 to 100 L, preferably 0.1 to 10 L against 1 mol of the compound of Formula [3].

The base to be used in this step includes a base as described in Step 3 of Preparation Process 1.

The amount of base to be used may be appropriately selected from a range of 0.2 to 10 mol, preferably 0.2 to 5.0 mol against 1 mol of the compound of Formula [3].

The reaction temperature may be selected from a range of from −20° C. to the boiling point range of the applied inert solvent, preferably 0° C. to 100° C.

The reaction time is normally 10 min. to 48 h. although it differs by the reaction temperature, the reaction substrate, the reaction amount, etc.

The compound of Formula [1], which is the reaction target, may be collected from the reaction system by a common method after the reaction completes, and purified by operations such as the column chromatography or recrystallization, etc. as necessary.

<Preparation Process 3>

The compound represented by Formula [1] may also be prepared by a process consisting of a reaction formula exemplified below.

[Chemical Formula 19]

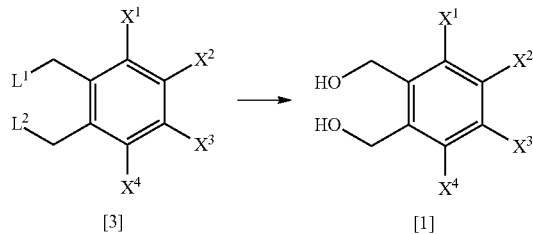

(wherein, $X^1$, $X^2$, $X^3$, $X^4$, $L^1$ and $L^2$ are each as defined in (1) and (3).)

The compound of Formula [1] may be prepared by reacting the compound of Formula [3] in water or a mixed solvent of water and an organic solvent under the presence or absence of base, ionic liquid and metal sulfate salt, preferably reacting the compound of Formula [3] in water or a mixed solvent of water and an organic solvent under the presence of base or metal sulfate salt, and more preferably reacting the compound of Formula [3] in water or a mixed solvent of water and an organic solvent.

The base that may be used in this step includes organic amines such as triethylamine, pyridine, 4-dimethylaminopyridine, N,N-dimethylaniline, 1,8-diazabicyclo [5,4,0]-7-undecen; metal carbonate salts such as sodium carbonate, potassium carbonate, magnesium carbonate, calcium carbonate; metal hydrogen carbonate salts such as sodium hydrogen carbonate, potassium hydrogen carbonate; and metal carboxylic acid salts represented by metal acetic acid salt such as sodium acetate, potassium acetate, calcium acetate, and magnesium acetate; metal alkoxides such as sodium methoxide, sodium ethoxide, sodium tert-butoxide, potassium methoxide, potassium tert-butoxide; metal hydroxides such as sodium hydroxide, potassium hydroxide, calcium hydroxide, magnesium hydroxide; and metal hydrides such as lithium hydride, sodium hydride, and calcium hydride. Preferable among those are metal carbonate salts such as sodium carbonate, potassium carbonate, magnesium carbonate and calcium carbonate; metal hydrogen carbonate salts such as sodium hydrogen carbonate, potassium hydrogen carbonate.

The amount of base to be used in this reaction may be appropriately selected from a range of 0 to 100 mol, preferably 0 to 10 mol against 1 mol of the compound of Formula [3].

The ionic liquid to be used in this step includes imidazolium salts such as 1-butyl-3-methylimidazoliumtetrafluoroborate, 1-butyl-2,3-dimethylimidazoliumtetrafluoroborate, 1-ethyl-3-methylimidazoliumtetrafluoroborate, 1-hexyl-3-methylimidazoliumtetrafluoroborate, 1-ethyl-3-methylimidazoliummethane sulfonate, 1-butyl-3-methylimidazoliumtrifluoromethanesulfonate, 1-butyl-2,3-dimethylimidazoliumtrifluoromethanesulfonate, 1-ethyl-3-methylimidazoliumtrifluoromethanesulfonate, 1-hexyl-3-methylimidazoliumtrifluoromethanesulfonate; ammonium salts such as tetrabutylammonium fluoride, tetrabutylammonium chloride, tetrabutylammonium bromide, tetrabutylammonium iodide.

The amount of ionic liquid to be used in this reaction may be appropriately selected from a range of 0 to 100 mol, preferably 0 to 10 mol against 1 mol of the compound of Formula [3].

The metal sulfate salts to be used in this step includes copper (II) sulfate or iron (III) sulfate.

The amount of metal sulfate salts to be used in this reaction may be appropriately selected from a range of 0 to 100 mol, preferably 0 to 1.0 mol against 1 mol of the compound of Formula [3].

The solvent to be used in this step includes water and a solvent as described in Step 1 of Preparation Process 1.

The amount of solvent to be used may be appropriately selected from a range of 0.01 to 100 L, preferably 0.1 to 10 L against 1 mol of the compound of Formula [3].

The reaction temperature may be selected from a range of from −20° C. to the boiling point range of the applied inert solvent, preferably 0° C. to 100° C.

The reaction time is normally 10 min. to 48 h. although it differs by the reaction temperature, the reaction substrate, the reaction amount, etc.

The compound of Formula [1], which is the reaction target, may be collected from the reaction system by a common method after the reaction completes, and purified by operations such as the column chromatography or recrystallization, etc. as necessary.

<Preparation Process 4>

The compound of the present invention represented by Formula [5] may be prepared by a process consisting of a reaction formula exemplified below.

[Chemical Formula 20]

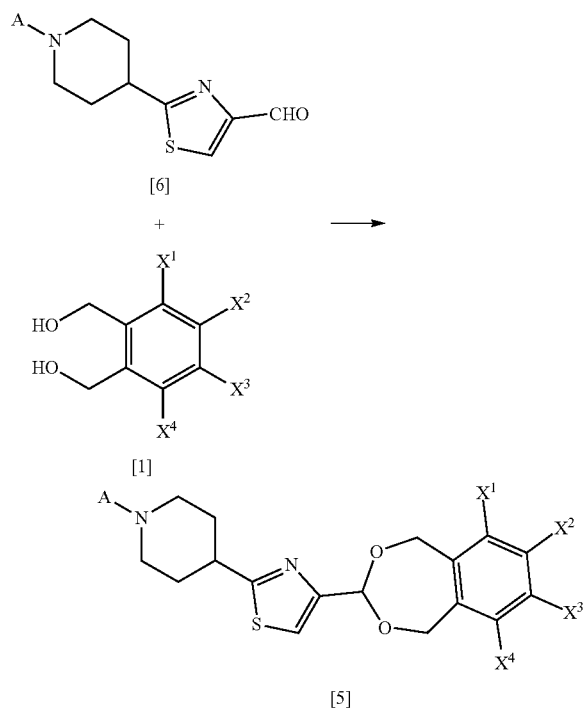

(wherein, A is as defined in (26), and $X^1$, $X^2$, $X^3$, and $X^4$ are as defined in (1).)

The compound represented by Formula [1] and the compound represented by Formula [6] are reacted in the solvent under the presence of acid or Lewis acid, preferably acid, to prepare the compound of the present invention represented by Formula [5].

The amount of the compound of Formula [1] to be used in this step may be appropriately selected from a range of 1.0 to 10 mol, preferably 1.0 to 3.0 mol against 1 mol of the compound of Formula [6].

The acid that may be used in this step includes inorganic acids such as hydrochloric acid, hydrobromic acid, sulfuric acid; and organic acids such as acetic acid, trifluoroacetic acid, p-toluenesulfonic acid, trifluoromethanesulfonic acid.

The Lewis acid that may be used in this step includes include zinc chloride, aluminum chloride, tin chloride, boron trichloride, boron trifluoride, trimethylsilyl trifluoromethanesulfonate.

The amount of acid or Lewis acid used may be selected appropriately from a range of from 0.01 to 5 mol, preferably from 0.1 to 1.0 mol, against 1 mol of the compound of Formula [6].

The solvent used in this step includes a solvent as described in Step 1 of Preparation Process 1.

The amount of solvent to be used may be appropriately selected from a range of 0.01 to 100 L, preferably 0.1 to 10 L against 1 mol of the compound of Formula [6].

The reaction temperature may be selected from a range of from −20° C. to the boiling point range of the applied inert solvent, preferably 0° C. to 150° C.

The reaction time is normally 10 min. to 48 h. although it differs by the reaction temperature, the reaction substrate, the reaction amount, etc.

The compound of Formula [5], which is the reaction target, may be collected from the reaction system by a common method after the reaction completes, and purified by operations such as the column chromatography or recrystallization, etc. as necessary.

<Intermediate Preparation Process 1>

[Chemical Formula 21]

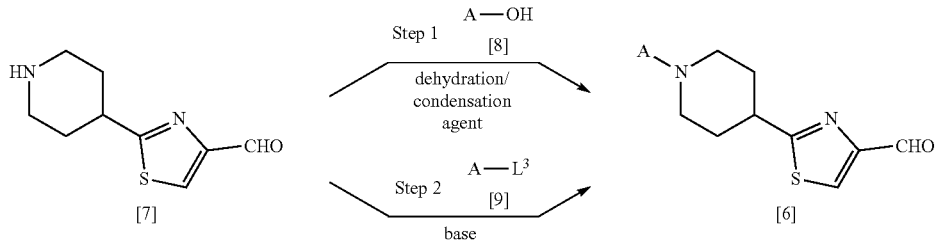

(wherein, A is as defined in (26), and $L^3$ is a halogen atom such as a chlorine atom, or bromine atom.)

(Step 1)

The compound of Formula [6] is prepared by reacting the compound of Formula [7] with the compound of Formula [8] in a solvent under the presence or absence of base, and under the presence of dehydration/condensation agent.

The amount of the compound of Formula [8] used in this step may be appropriately selected from a range of 0.5 to 10 mol, preferably 1.0 to 1.2 mol against 1 mol of the compound of Formula [7].

The dehydration/condensation agent used in this step includes dicyclohexylcarbodiimide (DCC), N-(3-dimethylaminopropyl)-N'-ethyl carbodiimide (EDC or WSC), N,N- carbonyl diimidazole, 2-chloro-1,3-dimethylimidazolium chloride, 2-chloro-1-pyridinium iodide.

The amount of the dehydration/condensation agent used in this reaction may be appropriately selected from a range of 1.0 to 10 mol, preferably 1.0 to 3.0 mol against 1 mol of the compound of Formula [7].

The base that may be used in this step includes organic amines such as triethylamine, pyridine, 4-dimethylaminopyridine, N,N-dimethylaniline, 1,8-diazabicyclo [5,4,0]-7-undecen, etc.; metal carbonate salts such as sodium carbonate, potassium carbonate, magnesium carbonate, calcium carbonate, etc.; metal hydrogen carbonate salts such as sodium hydrogen carbonate, potassium hydrogen carbonate, etc.; and metal carboxylic acid salts represented by metal acetic acid salt such as sodium acetate, potassium acetate, calcium acetate, and magnesium acetate, etc.; metal alkoxides such as sodium methoxide, sodium ethoxide, sodium tert-butoxide, potassium methoxide, potassium tert-butoxide, etc.; metal hydroxides such as sodium hydroxide, potassium hydroxide, calcium hydroxide, magnesium hydroxide, etc.; and metal hydrides such as lithium hydride, sodium hydride, and calcium hydride, etc.

The amount of base used in this reaction may be appropriately selected from a range of 0 to 100 mol, preferably 0 to 10 mol against 1 mol of the compound of Formula [7].

The solvent used in this step includes a solvent as described in Step 1 of Preparation Process 1.

The amount of solvent to be used in this reaction may be appropriately selected from a range of 0.01 to 100 L, preferably 0.1 to 10 L against 1 mol of the compound of Formula [7].

The reaction temperature may be selected from a range of from −20° C. to the boiling point range of the applied inert solvent, preferably 0° C. to 100° C.

The reaction time is normally 10 min. to 48 h. although it differs by the reaction temperature, the reaction substrate, the reaction amount, etc.

The compound of Formula [6], which is the reaction target, may be collected from the reaction system by a common method after the reaction completes, and purified by operations such as the column chromatography or recrystallization, etc. as necessary.

(Step 2)

The compound of Formula [6] may also be prepared by reacting the compound of Formula [7] with the compound of Formula [9] in a solvent under the presence of base.

The amount of the compound of Formula [9] used in this step may be appropriately selected from a range of 0.5 to 10 mol, preferably 1.0 to 1.2 mol against 1 mol of the compound of Formula [7].

The base to be used in this step includes a base as described in Step 1 of Intermediate Preparation Process 1.

The amount of base used in this reaction may be appropriately selected from a range of 0 to 100 mol, preferably 0 to 10 mol against 1 mol of the compound of Formula [7].

The solvent to be used in this step includes a solvent as described in Step 1 of Preparation Process 1.

The amount of solvent used in this step may be appropriately selected from a range of 0.01 to 100 L, preferably 0.1 to 10 L against 1 mol of the compound of Formula [7].

The reaction temperature may be selected from a range of from −20° C. to the boiling point range of the applied inert solvent, preferably 0° C. to 100° C.

The reaction time is normally 10 min. to 48 h. although it differs by the reaction temperature, the reaction substrate, the reaction amount, etc.

The compound of Formula [6], which is the reaction target, may be collected from the reaction system by a common method after the reaction completes, and purified by operations such as the column chromatography or recrystallization, etc. as necessary.

Cases in which the reagent and the reaction condition of the compounds of Formula [1], Formula [2], Formula [3], Formula [4] or Formula [5] do not match the specific functional groups existing in the intermediate are anticipated. In these examples, it is possible to obtain the desired product by adopting in the synthesis, the means of protection/deprotection or the mutual conversion of functional groups. A use of and options of the protection groups should be obvious to a person skilled in the art of chemical synthesis (e.g. T. W. Greene and P. G. Wuts, Protective Groups in Organic Synthesis, 4th ed.; Wiley: New York, 2007). A person skilled in the art would recognize that additional synthesis steps from a common method, not explained herein, may need to be conducted to complete the synthesis of the compound of Formula [1], Formula [2], Formula [3], Formula [4] or Formula [5] after a specific reagent is introduced, in certain cases, as explained regarding the individual schemes. A person skilled in the art would also recognize that the combination of steps exemplified in the aforementioned schemes may need to be conducted in an order other than the specific order proposed for preparing the compound of Formula [1], Formula [2], Formula [3], Formula [4] or Formula [5].

EXAMPLES

The present invention is described in detail below by providing Examples, but it is assumed that a person skilled in the art is capable of making full use of the present invention without more detailed explanation. Hence, the following Examples are understood merely as exemplary cases that do not limit the present disclosure in any way. The steps in the following examples explain the procedure of each step in the entirety of the synthesis process, and the starting material of each step does not necessarily have to be prepared by performing the procedures of the specific formulation described in other examples or steps.

Note that the symbol "%" shows weight percentage and "part" shows weight parts in the following explanation.

[Example 1] Preparation of 3-methylsulfonyloxy-1,2-benzenedimethanol (Compound 1-1)

Step 1: Preparation of 1-methylsulfonyloxy-2,3-dimethylbenzene 2,3-Dimethyl phenol (10 g) was dissolved in tetrahydrofuran (125 mL), and triethyl amine (9.1 g) was added to that solution. Then, methanesulfonyl chloride (10.26 g) was added under ice-cold condition, and the mixture was stirred overnight at room temperature. Water was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure to obtain the subject compound (16.39 g, yield 100%).

$^1$H-NMR (CDCl$_3$/TMS δ (ppm) value): 2.26 (s, 3H), 2.31 (s, 3H), 3.17 (s, 3H), 7.11-7.15 (m, 3H).

Step 2: Preparation of 1-methylsulfonyloxy-2,3-bis(bromomethyl)benzene

The product obtained in Step 1 of Example 1 above (16.39 g) was dissolved in carbon tetrachloride (300 mL), to which N-bromosuccinimide (32.05 g) and 2,2'-azobisisobutyronitrile (671 mg) were added, and the mixture was subjected to 4 h. of reflux under heating. The reaction solution was cooled to room temperature, run through a filter using Celite, and subjected to distillation under reduced pressure to remove the solvent and obtain the subject compound (29.3 g, yield 100%).

$^1$H-NMR (CDCl$_3$/TMS δ (ppm) value): 3.20 (s, 3H), 4.87 (s, 2H), 5.00 (s, 2H), 7.04 (d, 1H), 7.16-7.23 (m, 2H).

Step 3: Preparation of 1-methylsulfonyloxy-2,3-bis(acetyloxymethyl)benzene

The product obtained in Step 2 of Example 1 above (506 mg) was dissolved in N,N-dimethylformamide (2.8 mL), to which sodium acetate (241 mg) was added, and the mixture was stirred at room temperature overnight. Water was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure to obtain the subject compound (380 mg, yield 85%).

$^1$H-NMR (CDCl$_3$/TMS δ (ppm) value): 2.07 (s, 3H), 2.11 (s, 3H), 3.28 (s, 3H), 5.25 (s, 2H), 5.30 (s, 2H), 7.40-7.43 (m, 3H).

Also, the subject compound may be prepared by Step 3A and Step 3B shown below.

Step 3A: Preparation of 1-methylsulfonyloxy-2,3-bis(chloromethyl)benzene

The product obtained in Step 1 of Example 1 above (1 g) was dissolved in chlorobenzene (25 mL), to which 2,2'-azobisisobutyronitrile (0.05 g) was added. The reaction solution was heated to 90° C., and bubbled with chlorine gas (3.15 equivalent against the starting material). The reaction solution was cooled to room temperature, and subsequently subjected to distillation under reduced pressure to remove the solvent and to obtain a crude product including the subject compound. The crude product was used in the next step without being purified.

$^1$H-NMR (CDCl$_3$/TMS δ (ppm) value): 3.29 (s, 3H), 4.75 (s, 2H), 4.84 (s, 2H), 7.38-7.51 (m, 3H).

Step 3B: Alternative Preparation of 1-methylsulfonyloxy-2,3-bis(acetyloxymethyl)benzene The crude product obtained in Step 3A of Example 1 above (630 mg) was dissolved in toluene (23 mL), to which sodium acetate (480 mg) and tetrabutylammonium bromide (75 mg) were added, and the mixture was stirred at 80° C. for 7 h. After the reaction solution was cooled to room temperature, water was added, and extraction was performed using ethyl acetate. The organic layer was washed with a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 40%) using flash automatic purification device (Biotage AB/Isolera™) to obtain the subject compound (310 mg).

Step 4: Preparation of 3-methylsulfonyloxy-1,2-benzenedimethanol

The product obtained in Step 3 of Example 1 above (17 g) was dissolved in methanol (160 mL) and tetrahydrofuran (160 mL), to which water (40 mL) and potassium carbonate (15.23 g) were added under ice-cold condition, and the mixture was stirred for 3 h. Distillation was performed under reduced pressure to remove the solvent, and water was added, and extraction was performed using ethyl acetate. The organic layer was dried with anhydrous sodium sulfate, and the inorganic matter was filtered out, and then the solvent was removed by distillation under reduced pressure to obtain the subject compound (12.18 g, yield 98%).

$^1$H-NMR (DMSO-d6/TMS δ (ppm) value): 3.42 (s, 3H), 4.57 (d, 2H), 4.70 (d, 2H), 4.98 (t, 1H), 5.27 (t, 1H), 7.25 (d, 1H), 7.36 (t, 1H), 7.46 (d, 1H).

Additionally, the subject compound may be prepared by Step 4A shown below.

Step 4A: Alternative Preparation of 3-methylsulfonyloxy-1,2-benzenedimethanol To the product obtained in Step 2 of Example 1 above (502 mg) was added water (5.6 mL), and the mixture was subjected to 6 h. of reflux under heating. The reaction solution was cooled to room temperature, then, extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (325 mg, yield 100%).

[Example 2] Preparation of 3-methylsulfonyloxy-6-nitro-1,2-benzenedimethanol (Compound 1-14)

Step 1: Preparation of 1-methylsulfonyloxy-2,3-dimethyl-4-nitrobenzene 2,3-Dimethyl-4-nitrophenol (25 g) was dissolved in tetrahydrofuran (500 mL), to which triethylamine (16.7 g) was added. Then, methanesulfonyl chloride (18.93 g) was added under ice-cold condition, and the mixture was reacted in the same manner as the preparation process of Step 1 of Example 1, and aftertreatment was performed to obtain the subject compound (34.98 g, yield 95%).

$^1$H-NMR (CDCl$_3$/TMS δ (ppm) value): 2.36 (s, 3H), 2.44 (s, 3H), 3.26 (s, 3H), 7.30 (d, 1H), 7.67 (d, 1H).

Step 2: Preparation of 1-methylsulfonyloxy-2,3-bis(bromomethyl)-4-nitrobenzene The product obtained in Step 1 of Example 2 above (2.92 g) was dissolved in 1,2-dichloroethane (140 mL), to which N-bromosuccinimide (8.43 g) and 2,2'-azobisisobutyronitrile (195 mg) were added, and the mixture was subjected to 8 h. of reflux under heating. The reaction solution was cooled to room temperature and kept stationary overnight. After the precipitated solid was filtered out, the solvent was removed by distillation under reduced pressure to obtain the subject compound (4.8 g, yield 100%).

$^1$H-NMR (CDCl$_3$/TMS δ (ppm) value): 3.42 (s, 3H), 4.73 (s, 2H), 4.84 (s, 2H), 7.62 (d, 1H), 7.98 (d, 1H).

Step 3: Preparation of 1-methylsulfonyloxy-2,3-bis(acetyloxymethyl)-4-nitrobenzene The product obtained in Step 2 of Example 2 above (4.8 g) was dissolved in N,N-dimethylformamide (50 mL), to which sodium acetate (1.75 g) was added, and the mixture was stirred at room temperature overnight. Water was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 40%) using flash automatic purification device (Biotage AB/Isolera™) to obtain the subject compound (2.8 g, yield 65%).
$^1$H-NMR (CDCl$_3$/TMS δ (ppm) value): 2.04 (s, 3H), 2.08 (s, 3H), 3.36 (s, 3H), 5.37 (s, 2H), 5.47 (s, 2H), 7.60 (d, 1H), 7.89 (d, 1H).

Step 4: Preparation of 3-methylsulfonyloxy-6-nitro-1,2-benzenedimethanol

The product obtained in Step 3 of Example 2 above (2.8 g) was dissolved in methanol (80 mL) and tetrahydrofuran (80 mL), to which water (20 mL) and potassium carbonate (1.9 g) were added under ice-cold condition, and the mixture was stirred for 2 h. 1 Normal hydrochloric acid was added to the reaction solution and distillation was performed under reduced pressure to remove the solvent, then, water was added and extraction was performed using ethyl acetate. After the organic layer was dried with anhydrous sodium sulfate and the inorganic matter was filtered out, the solvent was removed by distillation under reduced pressure. The residue was subjected to purification by silica gel flash chromatography (elution by ethyl acetate-hexane: 50%) using flash automatic purification device (Biotage AB/Isolera™) to obtain the subject compound (1.59 g, yield 74%).
$^1$H-NMR (CDCl$_3$/TMS δ (ppm) value): 3.05-3.12 (m, 2H), 3.36 (s, 3H), 4.91 (dd, 4H), 7.48 (d, 1H), 7.89 (d, 1H).

[Example 3] Preparation of 3-fluoro-6-methylsulfonyloxy-1,2-benzenedimethanol (Compound 1-3)

Step 1: Preparation of 1-amino-2,3-dimethyl-4-methylsulfonyloxybenzene

The product obtained in Step 1 of Example 2 above (10 g) was dissolved in methanol (200 mL), to which palladium/carbon (2 g, palladium content 10%, about 55% water wet product) were added, and the mixture was stirred at room temperature for 24 h. under a hydrogen atmosphere. The reaction solution was run through a filter using Celite, and subjected to distillation under reduced pressure to remove the solvent and obtain the subject compound (8.43 g, yield 96%).
$^1$H-NMR (CDCl$_3$/TMS δ (ppm) value): 2.09 (s, 3H), 2.26 (s, 3H), 3.12 (s, 3H), 3.64 (brs, 2H), 6.54 (d, 1H), 6.98 (d, 1H).
The subject compound may be prepared by Step 1A shown below as well.

Step 1A: Alternative Preparation of 1-amino-2,3-dimethyl-4-methylsulfonyloxybenzene 2,3-Dimethyl-4-nitrophenol (25.3 g) was dissolved in ethyl acetate (300 mL), to which triethylamine (16.8 g) was added. Then, methanesulfonyl chloride (18.2 g) was added under ice-cold condition, and the mixture was stirred at room temperature for 30 min. Palladium/carbon (8 g, palladium content 10%, about 55% water wet product) were added to the reaction solution, and the mixture was stirred at room temperature for 24 h. under a hydrogen atmosphere. The reaction solution was run through a filter using Celite, and subjected to distillation under reduced pressure to remove the solvent and obtain the subject compound (33 g, yield 100%).

Step 2: Preparation of 2,3-dimethyl-4-methylsulfonyloxybenzenediazonium tetrafluoroborate The product obtained in Step 1 of Example 3 above (15.6 g) was dissolved in 48% tetrafluoroboric acid aqueous solution (84 mL) and water (120 mL), to which an aqueous solution consisting of sodium nitrite (5.1 g) dissolved in water (12 mL) was added over 10 min. under ice-cold condition, and the mixture was stirred for 1.5 h under ice-cold condition. The reaction solution was run through a filter, and the obtained solid was washed with diethyl ether and subsequently dried to obtain the subject compound (19.5 g, yield 86%).

Step 3: Preparation of 1-fluoro-2,3-dimethyl-4-methylsulfonyloxybenzene

To a product obtained in Step 2 of Example 3 above (0.5 g) was added 1-butyl-3-methylimidazolium tetrafluoroborate (1.8 g), and the mixture was stirred at 80° C. for 2 h. The reaction solution was cooled to room temperature and subjected to extraction using toluene. The organic layer was washed with water and a saturated saline solution, and dried with anhydrous sodium sulfate. After the inorganic matter was filtered out, the solvent was removed by distillation under reduced pressure to obtain the subject compound (0.29 g, yield 83%).
$^1$H-NMR (CDCl$_3$/TMS δ (ppm) value): 2.21 (d, 3H), 2.28 (s, 3H), 3.18 (s, 3H), 6.90 (t, 1H), 7.11 (dd, 1H).
The subject compound may also be prepared by Step 3A or Step 3B as shown below.

Step 3A: Alternative Preparation of 1-fluoro-2,3-dimethyl-4-methylsulfonyloxybenzene To a product obtained in Step 1 of Example 3 above (1 g) was added hydrogen fluoride pyridine (8 mL) under ice-cold condition, then sodium nitrite (355 mg) was added little by little and the mixture was stirred for 30 min. The mixture was subsequently stirred at 55° C. for 1.5 h. The reaction solution was cooled to room temperature and subjected to extraction using diethyl ether. The organic layer was washed with a saturated sodium hydrogencarbonate solution and a saturated saline solution, and dried with anhydrous sodium sulfate. After the inorganic matter was filtered out, the solvent was removed by distillation under reduced pressure to obtain the subject compound (0.75 g, yield 74%).

Step 3B: Alternative Preparation of 1-fluoro-2,3-dimethyl-4-methylsulfonyloxybenzene 2,3-Dimethyl-4-fluorophenol (200 mg) was dissolved in ethyl acetate (5 mL), to which triethylamine (174 mg) was added. Then, methanesulfonyl chloride (180 mg) was added at room temperature, and the mixture was stirred for 30 min. Water was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure to obtain the subject compound (290 mg, yield 93%).

Step 4: Preparation of 1-fluoro-2,3-bis(bromomethyl)-4-methylsulfonyloxybenzene

The product obtained in Step 3 of Example 3 above (1.48 g) was dissolved in chlorobenzene (15 mL), to which water (8 mL), and 2,2'-azobisisobutyronitrile (0.11 g) were added, and the reaction solution was heated to 80° C., to which a solution consisting of bromine (1 mL) dissolved in chlorobenzene (15 mL) was added over 30 min, and the mixture was stirred at 80° C. for 1.5 h. The reaction solution was cooled to room temperature and subjected to extraction using ethyl acetate. The organic layer was washed with water, sodium thiosulfate aqueous solution, and a saturated saline solution, and dried with anhydrous sodium sulfate. After the inorganic matter was filtered out, the solvent was removed by distillation under reduced pressure to obtain the subject compound (2.45 g, yield 96%).
$^1$H-NMR (CDCl$_3$/TMS δ (ppm) value): 3.33 (s, 3H), 4.65 (d, 2H), 4.68 (s, 2H), 7.12 (t, 1H), 7.42 (dd, 1H).

Step 5: Preparation of 1-fluoro-2,3-bis(acetyloxymethyl)-4-methylsulfonyloxybenzene The product obtained in Step 4 of Example 3 above (16.71 g) was dissolved in N,N-dimethylformamide (50 mL), to which sodium acetate (7.65 g) was added, and the mixture was reacted in the same manner as the preparation process in Step 3 of Example 2 and then purified to obtain the subject compound (11.81 g, yield 80%).
$^1$H-NMR (CDCl$_3$/TMS δ (ppm) value): 2.06 (s, 3H), 2.07 (s, 3H), 3.29 (s, 3H), 5.29 (d, 2H), 5.31 (s, 2H), 7.17 (t, 1H), 7.44 (dd, 1H).

The subject compound may also be prepared by Step 5A and Step 5B shown below.

Step 5A: Preparation of 1-fluoro-2,3-bis(chloromethyl)-4-methylsulfonyloxybenzene The product obtained in Step 3 of Example 3 above (1 g) was dissolved in chlorobenzene (25 mL), to which 2,2'-azobisisobutylonitrile (0.08 g) was added. The reaction solution was heated to 88° C., and bubbled with chlorine gas (4.1 equivalent against the starting material). The reaction solution was cooled to room temperature, and subsequently subjected to distillation under reduced pressure to remove the solvent and to obtain a crude product including the subject compound. The crude product was used in the next step without being purified.
$^1$H-NMR (CDCl$_3$/TMS δ (ppm) value): 3.33 (s, 3H), 4.79 (s, 2H), 4.82 (s, 2H), 7.14-7.19 (m, 1H), 7.44-7.47 (m, 1H).

Step 5B: Alternative Preparation of 1-fluoro-2,3-bis(acetyloxymethyl)-4-methylsulfonyloxy benzene The crude product obtained in Step 5A of Example 3 above (2 g) was dissolved in toluene (20 mL), to which sodium acetate (1.32 g) and tetrabutyl ammonium bromide (225 mg) were added, and the mixture was stirred at 80° C. for 5 h. The reaction solution was cooled to room temperature, and a saturated saline solution was added and extraction was performed using toluene. The organic layer was dried with anhydrous sodium sulfate, the inorganic matter was filtered out, and then the solvent was removed by distillation under reduced pressure. The residue was subjected to purification by silica gel flash chromatography (elution by ethyl acetate-hexane: 35%) using flash automatic purification device (Biotage AB/Isolera™) to obtain the subject compound (1.47 g).

Step 6: Preparation of 3-fluoro-6-methylsulfonyloxy-1,2-benzenedimethanol

The product obtained in Step 5 of Example 3 above (7.19 g) was dissolved in methanol (20 mL), to which water (4 mL) and potassium carbonate (6.53 g) were added under ice-cold condition, and the mixture was stirred for 15 min. The solvent was removed by distillation under reduced pressure, and extraction was performed using ethyl acetate. The organic layer was washed with a saturated saline solution and dried with anhydrous sodium sulfate. After the inorganic matter was filtered out, the solvent was removed by distillation under reduced pressure to obtain the subject compound (5.38 g, yield 100%).
$^1$H-NMR (CDCl$_3$/TMS δ (ppm) value): 3.27 (s, 3H), 3.53 (brs, 1H), 3.65 (brs, 1H), 4.80 (s, 2H), 4.84 (s, 2H), 7.11 (dd, 1H), 7.26-7.29 (m, 1H).

The subject compound may also be prepared by Step 6A, 6B, 6C, 6D or 6E shown below.

Step 6A: Alternative Preparation of 3-fluoro-6-methylsulfonyloxy-1,2-benzenedimethanol The product obtained in Step 4 of Example 3 above (10 g) was dissolved in N,N-dimethylformamide (27 mL), to which sodium acetate (4.58 g) was added, and the mixture was stirred at 50° C. for 4 h. After the reaction solution was cooled to room temperature, methanol (20 mL), water (5 mL), potassium carbonate (7.73 g) were added, and the mixture was stirred for 2 h. After water was added to the reaction solution, extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (6.43 g, yield 97%).

Step 6B: Alternative Preparation of 3-fluoro-6-methylsulfonyloxy-1,2-benzenedimethanol To the product obtained in Step 4 of Example 3 above (0.38 g) was added water (10 mL), and the mixture was subjected to 6 h. of reflux under heating. After the reaction solution was cooled to room temperature, extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (0.23 g, yield 92%).

Step 6C: Alternative Preparation of 3-fluoro-6-methylsulfonyloxy-1,2-benzenedimethanol The product obtained in Step 4 of Example 3 above (10 g) was dissolved in N,N-dimethylformamide (27 mL), to which water (240 mL) was added, and the mixture was stirred at 100° C. for 3 h. After the reaction solution was cooled to room temperature, extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (6.66 g, yield 100%).

Step 6D: Alternative Preparation of 3-fluoro-6-methylsulfonyloxy-1,2-benzenedimethanol The product obtained in Step 4 of Example 3 above (5 g) was dissolved in N,N-dimethylformamide (11 mL), to which copper (II) sulfate pentahydrate (234 mg) and water (30 mL) were added, and the mixture was subjected to 7 h. of reflux under heating at 110° C. After the reaction solution was cooled to room temperature, water was added and extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (3.1 g, yield 93%).

Step 6E: Alternative Preparation of 3-fluoro-6-methylsulfonyloxy-1,2-benzenedimethanol The product obtained in Step 5 of Example 3 above (4.46 g) was dissolved in methanol (20 mL), to which acetyl chloride (208 mg) was added, and the mixture was stirred at room temperature overnight. Water was added to the reaction solution, and extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (2.8 g, yield 84%).

[Example 4] Preparation of 3-chloro-6-methylsulfonyloxy-1,2-benzenedimethanol (Compound 1-17)

Step 1: Preparation of 1-chloro-2,3-dimethyl-4-methylsulfonyloxybenzene 2,3-Dimethyl-4-chlorophenol (1.81 g) was dissolved in tetrahydrofuran (20 mL), to which triethylamine (1.41 g) was added. Then, methanesulfonyl chloride (1.45 g) was added under ice-cold condition, and the mixture was reacted in the same manner as the preparation process of Step 1 of Example 1, and aftertreatment was performed to obtain the subject compound (1.86 g, yield 68%).
$^1$H-NMR (CDCl$_3$/TMS δ (ppm) value): 2.31 (s, 3H), 2.37 (s, 3H), 3.19 (s, 3H), 7.10 (dd, 1H), 7.25 (dd, 1H).

Step 2: Preparation of 1-chloro-2,3-bis(bromomethyl)-4-methylsulfonyloxybenzene

The product obtained in Step 1 of Example 4 above (1.86 g) was dissolved in 1,2-dichloroethane (50 mL), to which N-bromosuccinimide (4.23 g) and 2,2'-azobisisobutyronitrile (130 mg) were added, and the mixture was subjected to 3 h. of reflux under heating. After the reaction solution was cooled to room temperature, water was added, and extraction was performed using chloroform. The organic layer was washed with a saturated saline solution, and dried with anhydrous sodium sulfate. After the inorganic matter was filtered out, the solvent was removed by distillation under reduced pressure to obtain the subject compound (3.11 g, yield 100%).
$^1$H-NMR (CDCl$_3$/TMS δ (ppm) value): 3.34 (s, 3H), 4.69 (s, 2H), 4.76 (s, 2H), 7.39-7.45 (m, 2H).

Step 3: Preparation of 1-chloro-2,3-bis(acetyloxymethyl)-4-methylsulfonyloxy benzene The product obtained in Step 2 of Example 4 above (3.11 g) was dissolved in N,N-dimethylformamide (40 mL), to which sodium acetate (1.56 g) was added, and the mixture was stirred at room temperature overnight. Water was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure to obtain a crude product including the subject compound. The crude product was used in the next step without being purified.
$^1$H-NMR (CDCl$_3$/TMS δ (ppm) value): 2.06 (s, 3H), 2.09 (s, 3H), 3.30 (s, 3H), 5.31 (s, 2H), 5.36 (s, 2H), 7.42 (d, 1H), 7.49 (d, 1H).

Step 4: Preparation of 3-chloro-6-methylsulfonyloxy-1,2-benzenedimethanol

The crude product obtained in Step 3 of Example 4 above was dissolved in methanol (20 mL), and tetrahydrofuran (20 mL), to which water (5 mL) and potassium carbonate (2.2 g) were added under ice-cold condition, and the mixture was stirred for 3 h. Water was added to the reaction solution, and extraction was performed using ethyl acetate. The organic layer was washed with a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 80%) using flash automatic purification device (Biotage AB/Isolera™) to obtain the subject compound (1.41 g).
$^1$H-NMR (CDCl$_3$/TMS δ (ppm) value): 2.57 (brs, 2H), 2.85 (s, 3H), 4.88 (s, 2H), 4.94 (s, 2H), 6.84 (d, 1H), 7.35 (d, 1H).

The subject compound may also be prepared by Step 4A shown below.

Step 4A: Alternative Preparation of 3-chloro-6-methylsulfonyloxy-1,2-benzenedimethanol To the product obtained in Step 2 of Example 4 above (1.64 g) was added water (42 mL), and the mixture was subjected to 7 h. of reflux under heating. After the reaction solution was cooled to room temperature, extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (1.11 g, yield 100%).

[Example 5] Preparation of 3-bromo-6-methylsulfonyloxy-1,2-benzenedimethanol (Compound 1-18)

Step 1: Preparation of 1-bromo-2,3-dimethyl-4-methylsulfonyloxybenzene 2,3-Dimethyl-4-bromophenol (6.57 g) was dissolved in tetrahydrofuran (100 mL), to which triethylamine (3.64 g)

was added. Then, methanesulfonyl chloride (4.12 g) was added under ice-cold condition, and the mixture was reacted in the same manner as the preparation process of Step 1 of Example 1, and aftertreatment was performed to obtain a crude product including the subject compound. The crude product was used in the next step without being purified.

$^1$H-NMR (CDCl$_3$/TMS δ (ppm) value): 2.33 (s, 3H), 2.41 (s, 3H), 3.19 (s, 3H), 7.04 (d, 1H), 7.44 (d, 1H).

Step 2: Preparation of 1-bromo-2,3-bis(bromomethyl)-4-methylsulfonyloxybenzene

The crude product obtained in Step 1 of Example 5 above (1.87 g) was dissolved in 1,2-dichloroethane (13 mL), to which N-bromosuccinimide (2.5 g) and 2,2'-azobisisobutyronitrile (110 mg) were added, and the mixture was subjected to reflux for 3 h. under heating. After the reaction solution was cooled to room temperature, it was washed with water and a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 30%) using flash automatic purification device (Biotage AB/Isolera™) to obtain the subject compound (2.66 g).

$^1$H-NMR (CDCl$_3$/TMS δ (ppm) value): 3.34 (s, 3H), 4.71 (s, 2H), 4.79 (s, 2H), 7.33 (d, 1H), 7.62 (d, 1H).

Step 3: Preparation of 1-bromo-2,3-bis(acetyloxymethyl)-4-methylsulfonyloxybenzene The product obtained in Step 2 of Example 5 above (15.28 g) was dissolved in N,N-dimethylformamide (100 mL), to which sodium acetate (6.31 g) was added, and the mixture was stirred at 90° C. for 3 h. After cooling the reaction solution to room temperature, water was added and extraction was performed using ethyl acetate. The organic layer was washed with water and a saturated saline solution, and dried with anhydrous sodium sulfate. After the inorganic matter was filtered out, the solvent was removed by distillation under reduced pressure to obtain a crude product including the subject compound. This crude product was used in the next step without being purified.

$^1$H-NMR (CDCl$_3$/TMS δ (ppm) value): 2.06 (s, 3H), 2.09 (s, 3H), 3.30 (s, 3H), 5.32 (s, 2H), 5.37 (s, 2H), 7.35 (d, 1H), 7.68 (d, 1H).

Step 4: Preparation of 3-bromo-6-methylsulfonyloxy-1,2-benzenedimethanol

The crude product obtained in Step 3 of Example 5 above (75 mL) was dissolved in methanol (75 mL) and tetrahydrofuran (25 mL), to which water (25 mL) and potassium carbonate (9.04 g) were added under ice-cold condition, and the mixture was stirred for 3 h. Water was added to the reaction solution, and extraction was performed using ethyl acetate. The organic layer was washed with a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 50%) using flash automatic purification device (Biotage AB/Isolera™) to obtain the subject compound (7.53 g).

$^1$H-NMR (CDCl$_3$/TMS δ (ppm) value): 2.10 (s, 2H), 3.29 (s, 3H), 4.86 (s, 2H), 5.01 (s, 2H), 7.17 (d, 1H), 7.64 (d, 1H).

The subject compound may also be prepared by Step 4A shown below.

Step 4A: Alternative Preparation of 3-bromo-6-methylsulfonyloxy-1,2-benzenedimethanol To the product obtained in Step 2 of Example 5 above (1.95 g) was added water (45 mL), and the mixture was subjected to 8 h. of reflux under heating. After the reaction solution was cooled to room temperature, extraction was performed using ethyl acetate. The organic layer was washed with a saturated saline solution, and dried with anhydrous sodium sulfate. After the inorganic matter was filtered out, the solvent was removed by distillation under reduced pressure to obtain the subject compound (1.35 g, yield 97%).

[Example 6] Preparation of 3-iodo-6-methylsulfonyloxy-1,2-benzenedimethanol (Compound 1-19)

Step 1: Preparation of 1-iodo-2,3-dimethyl-4-methylsulfonyloxy benzene

The product obtained in Step 1 of Example 3 above (3.44 g) was dissolved in dimethylsulfoxide (100 mL), to which potassium iodide (13.3 g), and sodium nitrite (4.41 g) were added, and 48% hydrobromic acid (20 mL) was added little by little under ice-cold condition, and the mixture was stirred for 3 h. A sodium thiosulfate aqueous solution was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 50%) using flash automatic purification device (Biotage AB/Isolera™) to obtain the subject compound (2.97 g, yield 57%).

$^1$H-NMR (CDCl$_3$/TMS δ (ppm) value): 2.35 (s, 3H), 2.47 (s, 3H), 3.18 (s, 3H), 6.89 (d, 1H), 7.72 (d, 1H).

Step 2: Preparation of 1-iodo-2,3-bis(bromomethyl)-4-methylsulfonyloxybenzene

The product obtained in Step 1 of Example 6 above (2.97 g) was dissolved in 1,2-dichloroethane (50 mL), to which N-bromosuccinimide (3.89 g) and 2,2'-azobisisobutylonitrile (150 mg) were added, and the mixture was subjected to 3 h. of reflux under heating. After the reaction solution was cooled to room temperature, water was added, and extraction was performed using chloroform. The organic layer was washed with water, and a saturated saline solution, and dried with anhydrous sodium sulfate. After the inorganic matter was filtered out, the solvent was removed by distillation under reduced pressure to obtain a crude product including the subject compound. This crude product was used in the next step without being purified.

$^1$H-NMR (CDCl$_3$/TMS δ (ppm) value): 3.34 (s, 3H), 4.74 (s, 2H), 4.80 (s, 2H), 7.18 (d, 1H), 7.89 (d, 1H).

Step 3: Preparation of 1-iodo-2,3-bis(acetyloxymethyl)-4-methylsulfonyloxybenzene The crude product obtained in Step 2 of Example 6 above was dissolved in N,N-dimethylformamide (50 mL), to which sodium acetate (1.79 g) was added, and the mixture was stirred at room temperature overnight. Water was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure to obtain a crude product including the subject compound. This crude product was used in the next step without being purified.

$^1$H-NMR (CDCl$_3$/TMS δ (ppm) value): 2.06 (s, 3H), 2.09 (s, 3H), 3.30 (s, 3H), 5.31 (s, 2H), 5.37 (s, 2H), 7.42 (d, 1H), 7.49 (d, 1H).

Step 4: Preparation of 3-iodo-6-methylsulfonyloxy-1,2-benzenedimethanol

The crude product obtained in Step 3 of Example 6 above was dissolved in methanol (20 mL), tetrahydrofuran (20 mL), to which water (5 mL), and potassium carbonate (2.52 g) were added, and the mixture was reacted in the same manner as the preparation process in Step 4 of Example 5 and then purified to obtain the subject compound (652 mg).

$^1$H-NMR (CDCl$_3$/TMS δ (ppm) value): 3.11-3.16 (m, 2H), 3.29 (s, 3H), 4.86 (d, 2H), 5.00 (d, 2H), 7.01 (d, 1H), 7.92 (d, 1H).

[Example 7] Preparation of 3-difluoromethoxy-6-methylsulfonyloxy-1,2-benzenedimethanol (Compound 1-21)

Step 1: Preparation of 2,3-dimethyl-4-difluoromethoxy-phenol 2,3-Dimethyl-4-[[(1,1-dimethylethyl)dimethylsilyl]oxy]phenol (820 mg)(compound described in European Journal of Organic Chemistry, (11), 2218-2225; 2010) was dissolved in acetonitrile (13 mL), to which water (13 mL), and potassium hydroxide (3.65 g) were added. After the reaction solution was cooled to −20° C., (bromodifluoromethyl) phosphonic acid diethyl ester (1.74 g) was added, and the mixture was further stirred at −20° C. for 1 h. Then, after the mixture was stirred at room temperature for 2.5 h, water was added to the reaction solution, and extraction was performed using ethyl acetate. The organic layer was washed with a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 50%) using flash automatic purification device (Biotage AB/Isolera™) to obtain the subject compound (200 mg, yield 33%).

$^1$H-NMR (CDCl$_3$/TMS δ (ppm) value): 2.18 (s, 3H), 2.21 (s, 3H), 5.01 (s, 1H), 6.37 (t, 1H), 6.60 (d, 1H), 6.84 (d, 1H).

Step 2: Preparation of 1-difluoromethoxy-2,3-dimethyl-4-methylsulfonyloxybenzene The product obtained in Step 1 of Example 7 above (200 mg) was dissolved in tetrahydrofuran (20 mL), to which triethylamine (178 mg) was added. Then, methanesulfonyl chloride (134 mg) was added under ice-cold condition, and the mixture was stirred at room temperature for 3 h. The reaction solution was run through a filter and subjected to distillation under reduced pressure to remove the solvent. The residue was subjected to purification by silica gel flash chromatography (elution by ethyl acetate-hexane: 50%) using flash automatic purification device (Biotage AB/Isolera™) to obtain the subject compound (220 mg, yield 78%).

$^1$H-NMR (CDCl$_3$/TMS δ (ppm) value): 2.24 (s, 3H), 2.29 (s, 3H), 3.19 (s, 3H), 6.47 (t, 1H), 6.99 (d, 1H), 7.15 (d, 1H).

Step 3: Preparation of 1-difluoromethoxy-2,3-bis(bromomethyl)-4-methylsulfonyloxybenzene The product obtained in Step 2 of Example 7 above (220 mg) was dissolved in carbon tetrachloride (10 mL), to which N-bromosuccinimide (353 mg) and 2,2'-azobisisobutyronitrile (13.6 mg) were added, and the mixture was subjected to 4 h. of reflux under heating. The reaction solution was cooled to room temperature, and then the solvent was removed by distillation under reduced pressure. The residue was subjected to purification by silica gel flash chromatography (elution by ethyl acetate-hexane: 50%) using flash automatic purification device (Biotage AB/Isolera™) to obtain the subject compound (340 mg, yield 97%).

$^1$H-NMR (CDCl$_3$/TMS δ (ppm) value): 3.34 (s, 3H), 4.68 (s, 2H), 4.69 (s, 2H), 6.58 (t, 1H), 7.20 (d, 1H), 7.45 (d, 1H).

Step 4: Preparation of 1-difluoromethoxy-2,3-bis(acetyloxymethyl)-4-methylsulfonyloxybenzene The product obtained in Step 3 of Example 7 above (340 mg) was dissolved in N,N-dimethylformamide (10 mL), to which sodium acetate (158 mg) was added, and the mixture was stirred at room temperature overnight. Water was added to the reaction solution, and extraction was performed using ethyl acetate. The organic layer was washed with water and a saturated saline solution, and dried with anhydrous sodium sulfate. After the inorganic matter was filtered out, the solvent was removed by distillation under reduced pressure to obtain the subject compound (306 mg, yield 100%).

$^1$H-NMR (CDCl$_3$/TMS δ (ppm) value): 2.06 (s, 6H), 3.30 (s, 3H), 5.30 (s, 2H), 5.31 (s, 2H), 6.53 (t, 1H), 7.27 (d, 1H), 7.48 (d, 1H).

Step 5: Preparation of 3-difluoromethoxy-6-methylsulfonyloxy-1,2-benzenedimethanol The product obtained in Step 4 of Example 7 above (306 mg) was dissolved in methanol (8 mL), and tetrahydrofuran (8 mL), to which water (2 mL), and potassium carbonate (222 mg) were added under ice-cold condition, and the mixture was stirred for 1 h. Water was added to the reaction solution, and extraction was performed using ethyl acetate. The organic layer was washed with a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-methanol: 15% of methanol) using flash automatic purification device (Biotage AB/Isolera™) to obtain the subject compound (130 mg, yield 55%)

$^1$H-NMR (CDCl$_3$/TMS δ (ppm) value): 3.27-3.30 (m, 5H), 4.82 (s, 2H), 4.86 (s, 2H), 6.57 (t, 1H), 7.22 (d, 1H), 7.31 (d, 1H).

[Example 8] Preparation of 3,6-bis(methylsulfonyloxy)-1,2-benzenedimethanol (Compound 1-20)

Step 1: Preparation of 1,4-bis(methylsulfonyloxy)-2,3-dimethylbenzene 2,3-Dimethylhydroquinone (1 g) was dissolved in tetrahydrofuran (12 mL), to which triethylamine (1.75 g) is added. Then, methanesulfonyl chloride (1.83 g) was added under ice-cold condition, the mixture was reacted in the same manner as the preparation process of Step 1 of Example 1, and aftertreatment was performed to obtain the subject compound (2.13 g, yield 100%).

$^1$H-NMR (CDCl$_3$/TMS δ (ppm) value): 2.30 (s, 6H), 3.21 (s, 6H), 7.20 (s, 2H).

Step 2: Preparation of 1,4-bis(methylsulfonyloxy)-2,3-bis(bromomethyl)benzene

The product obtained in Step 1 of Example 8 above (2 g) was dissolved in 1,2-dichloroethane (13 mL), to which N-bromosuccinimide (2.53 g) and 2,2'-azobisisobutyloni- trile (112 mg) were added, and the mixture was subjected to 3 h. of reflux under heating. The reaction solution was cooled to room temperature, and then washed with water and a saturated saline solution, and dried with anhydrous sodium sulfate. After the inorganic matter was filtered out, the solvent was removed by distillation under reduced pressure to obtain the subject compound (2.81 g, yield 92%).

$^1$H-NMR (CDCl$_3$/TMS δ (ppm) value): 3.36 (s, 6H), 4.69 (s, 4H), 7.50 (s, 2H).

Step 3: Preparation of 1,4-bis(methylsulfonyloxy)-2,3-bis(acetyloxymethyl)benzene The product obtained in Step 2 of Example 8 above (2.68 g) was dissolved in N,N-dimethylformamide (40 mL), to which sodium acetate (1.07 g) was added, and the mixture was reacted in the same manner as the preparation process in Step 3 of Example 2 and then purified to obtain the subject compound (1.78 g, yield 60%).

$^1$H-NMR (CDCl$_3$/TMS δ (ppm) value): 2.07 (s, 6H), 3.31 (s, 6H), 5.34 (s, 4H), 7.51 (s, 2H).

Step 4: Preparation of 3,6-bis(methylsulfonyloxy)-1,2-benzenedimethanol

The product obtained in Step 3 of Example 8 above (1.78 g) was dissolved in methanol (40 mL), and tetrahydrofuran (40 mL), to which water (10 mL), and potassium carbonate (1.1 g) were added under ice-cold condition, and the mixture was reacted in the same manner as the preparation process in Step 4 of Example 2, and then purified to obtain the subject compound (916 mg, yield 64%).

$^1$H-NMR (CDCl$_3$/TMS δ (ppm) value): 3.30-3.38 (m, 8H), 4.86 (d, 4H), 7.39 (s, 2H).

The subject compound may also be prepared by Step 4A shown below.

Step 4A: Alternative Preparation of 3,6-bis(methylsulfonyloxy)-1,2-benzenedimethanol To the product obtained in Step 2 of Example 8 above (1 g) was added water (22 mL), and the mixture was subjected to 7 h. of reflux under heating. The reaction solution was cooled to room temperature, and then extraction was per- formed using ethyl acetate. The organic layer was washed with a saturated saline solution, and dried with anhydrous sodium sulfate. After the inorganic matter was filtered out, the solvent was removed by distillation under reduced pressure to obtain the subject compound (790 mg, yield 100%).

[Example 9] Preparation of 4-methylsulfonyloxy-1,2-benzenedimethanol (Compound 1-4)

Step 1: Preparation of 1-methylsulfonyloxy-3,4-dimethylbenzene 3,4-Dimethylphenol (2 g) was dissolved in tetrahydro- furan (25 mL), to which triethylamine (1.99 g) was added. Then, methanesulfonyl chloride (2.06 g) was added and the mixture was reacted in the same manner as the preparation process of Step 1 of Example 1, and aftertreatment was performed to obtain a crude product containing the subject compound. This crude product was used in the next step without being purified.

$^1$H-NMR (CDCl$_3$/TMS δ (ppm) value): 2.26 (s, 3H), 2.28 (s, 3H), 3.11 (s, 3H), 7.01 (dd, 1H), 7.06 (d, 1H), 7.15 (d, 1H).

Step 2: Preparation of 1-methylsulfonyloxy-3,4-bis(bromomethyl)benzene

The crude product obtained in Step 1 of Example 9 above was dissolved in carbon tetrachloride (60 mL), to which N-bromosuccinimide (6.4 g) and 2,2'-azobisisobutylonitrile (134 mg) were added and the mixture was reacted in the same manner as the preparation process of Step 2 of Example 1, and aftertreatment was performed to obtain a crude product containing the subject compound. This crude product was used in the next step without being purified.

$^1$H-NMR (CDCl$_3$/TMS δ (ppm) value): 3.18 (s, 3H), 4.61 (s, 2H), 4.63 (s, 2H), 7.22-7.25 (m, 1H), 7.32 (d, 1H), 7.42 (d, 1H).

Step 3: Preparation of 1-methylsulfonyloxy-3,4-bis (acetyloxymethyl)benzene

The crude product obtained in Step 2 of Example 9 above was dissolved in N,N-dimethylformamide (50 mL), to which sodium acetate (3.36 g) was added, and the mixture was reacted in the same manner as the preparation process in Step 3 of Example 2 and then purified to obtain the subject compound (3.26 g).

$^1$H-NMR (CDCl$_3$/TMS δ (ppm) value): 2.10 (s, 3H), 2.12 (s, 3H), 3.17 (s, 3H), 5.18 (s, 2H), 5.19 (s, 2H), 7.28 (d, 1H), 7.35 (d, 1H), 7.46 (d, 1H).

Step 4: Preparation of 4-methylsulfonyloxy-1,2-benzenedimethanol

The product obtained in Step 3 of Example 9 above (3.26 g) was dissolved in methanol (40 mL) and tetrahydrofuran (40 mL), to which water (20 mL) and potassium carbonate (2.6 g) were added under ice-cold condition, and the mixture was reacted in the same manner as the preparation process in Step 4 of Example 2 and then purified to obtain the subject compound (1.64 g, yield 69%).

$^1$H-NMR (CDCl$_3$/TMS δ (ppm) value): 2.63 (brs, 2H), 3.16 (s, 3H), 4.76 (s, 4H), 7.21-7.53 (m, 2H), 7.32 (s, 1H), 7.42 (d, 1H).

[Example 10] Preparation of 4-[4-(6-methylsulfony- loxy-1,5-dihydro-3H-2,4-benzodioxepin-3-yl)-2- thiazolyl]-1-[[5-methyl-3-(trifluoromethyl)-1H-pyra- zol-1-yl]acetyl]piperidine (Compound 2-1)

4-(4-Folmyl-2-thiazolyl)-1-[2-[5-methyl-3-(trifluorom- ethyl)-1H-pyrazol-1-yl]acetyl]piperidine (200 mg) (compound described in WO2008/013622), the product obtained in Example 1 (121 mg), and p-toluenesulfonic acid monohydrate (20 mg) were dissolved in toluene (20 mL), and subjected to reflux under heating for 1 h. using a Dean-Stark device. After the reaction solution was cooled to room temperature, it was diluted with ethyl acetate, and washed with water and saturated saline solution. After the organic layer was dried with anhydrous sodium sulfate and the inorganic matter was filtered out, the solvent was removed by distillation under reduced pressure. The residue was subjected to purification by silica gel flash chromatography (elution by ethyl acetate-hexane: 40%-100%) using flash automatic purification device (Biotage AB/Isolera™) to obtain the subject compound (298 mg, yield 96%).

[Example 11] Preparation of 4-[4-(6-fluoro-9-methylsulfonyloxy-1,5-dihydro-3H-2,4-benzodioxepin-3-yl)-2-thiazolyl]-1-[[5-methyl-3-(trifluoromethyl)-1H-pyrazol-1-yl]acetyl]piperidine (Compound 2-3)

4-(4-Formyl-2-thiazolyl)-1-[2-[5-methyl-3-(trifluoromethyl)-1H-pyrazol-1-yl]acetyl]piperidine (220 mg) (compound described in WO2008/013622), the product obtained in Example 3 (150 mg), and p-toluenesulfonic acid monohydrate (20 mg) were dissolved in toluene (15 mL), and the mixture was reacted in the same manner as the reaction in the preparation of Compound 2-1, and then purified to obtain the subject compound (297 mg, yield 84%).

[Example 12] Preparation of 4-[4-(6-methylsulfonyloxy-1,5-dihydro-3H-2,4-benzodioxepin-3-yl)-2-thiazolyl]-1-[[3,5-bis(difluoromethyl)-1H-pyrazol-1-yl]acetyl]piperidine (Compound 2-15)

4-(4-Formyl-2-thiazolyl)-1-[2-[3,5-bis(difluoromethyl)-1H-pyrazol-1-yl]acetyl]piperidine (202 mg) (compound described in WO2010/066353), the product obtained in Example 1 (232 mg), and p-toluenesulfonic acid monohydrate (5 mg) were dissolved in toluene (15 mL), and the mixture was reacted in the same manner as the reaction in the preparation of Compound 2-1 and then purified to obtain the subject compound (164 mg, yield 53%).

[Example 13] Preparation of 4-[4-(6-fluoro-9-methylsulfonyloxy-1,5-dihydro-3H-2,4-benzodioxepin-3-yl)-2-thiazolyl]-1-[2-[3,5-bis(difluoromethyl)-1H-pyrazol-1-yl]acetyl]piperidine (Compound 2-23)

4-(4-Formyl-2-thiazolyl)-1-[2-[3,5-bis(difluoromethyl)-1H-pyrazol-1-yl]acetyl]piperidine (202 mg) (compound described in WO2010/066353), the product obtained in Example 3 (250 mg), and p-toluenesulfonic acid monohydrate (5 mg) were dissolved in toluene (15 mL), and the mixture was reacted in the same manner as the reaction in the preparation of Compound 2-1, and then purified to obtain the subject compound (105 mg, yield 33%).

[Example 14] Preparation of 4-[4-(6-methylsulfonyloxy-1,5-dihydro-3H-2,4-benzodioxepin-3-yl)-2-thiazolyl]-1-[2-(2,5-dimethylphenyl)acetyl]piperidine (Compound 3-1)

4-(4-Formyl-2-thiazolyl)-1-[2-(2,5-dimethylphenyl)acetyl]piperidine (200 mg), the product obtained in Example 1 (142 mg), and p-toluenesulfonic acid monohydrate (20 mg) were dissolved in toluene (15 mL), and the mixture was reacted in the same manner as the reaction in the preparation of Compound 2-1, and then purified to obtain the subject compound (206 mg, yield 64%).

[Example 15] Preparation of 4-[4-(6-methylsulfonyloxy-1,5-dihydro-3H-2,4-benzodioxepin-3-yl)-2-thiazolyl]-1-[2-(2,5-dichlorophenyl)acetyl]piperidine (Compound 3-2)

4-(4-Formyl-2-thiazolyl)-1-[2-(2,5-dichlorophenyl)acetyl]piperidine (191 mg), the product obtained in Example 1 (232 mg), and p-toluenesulfonic acid monohydrate (5 mg) were dissolved in toluene (15 mL), and the mixture was reacted in the same manner as the reaction in the preparation of Compound 2-1, and then purified to obtain the subject compound (267 mg, yield 72%).

Shown in Examples 16 to 18 are Production Examples of the production starting materials used in Examples 1 to 15.

[Example 16] Preparation of 2,3-dimethyl-4-nitrophenol 2,3-Dimethyl-4-nitrosophenol (500 mg) was suspended in methanol (10 mL), to which sodium tungstate dehydrate (54 mg) was added, and the reaction solution was heated to 60° C. To this solution was gradually added 30% hydrogen peroxide aqueous solution (563 mg), and the mixture was stirred at 60° C. for 8 h. The reaction solution was cooled to room temperature, to which sodium sulfite and water were added, and the mixture was subjected to extraction using ethyl acetate. After the organic layer was dried with anhydrous sodium sulfate and the inorganic matter was filtered out, the solvent was removed by distillation under reduced pressure to obtain the subject compound (500 mg, yield 90%).

[Example 17] Preparation of 4-(4-formyl-2-thiazolyl)-1-[2-(2,5-dimethylphenyl)acetyl]piperidine Step 1: Preparation of 4-(4-formyl-2-thiazolyl)piperidinetrifluoroacetate Salt 4-(4-Formyl-2-thiazolyl)piperidine carboxylic acid 1,1-dimethylethyl ester (3.9 g) (compound described in WO 2008/013622) was dissolved in dichloromethane (65 mL), to which trifluoroacetic acid (15.2 mL) was added, and the mixture was stirred at room temperature overnight. Dichloromethane and trifluoroacetic acid were removed by distillation under reduced pressure to obtain the subject compound.

Step 2: Preparation of 4-(4-formyl-2-thiazolyl)-1-[2-(2,5-dimethylphenyl)acetyl]piperidine The product obtained in Step 1 of Example 17 above (1 g) was dissolved in dichloromethane (50 mL), to which 2,5-dimethylphenyl acetic acid (919 mg) and 1-(3-dimethylaminopropyl)-3-ethylcarbodiimide hydrochloric acid salt (1.07 g) were added, and the mixture was stirred at room temperature overnight. Water was added to the reaction solution, and extraction was performed using chloroform. The organic layer was washed with water and a saturated saline solution, and dried with anhydrous sodium sulfate. After the inorganic matter was filtered out, the solvent was removed by distillation under reduced pressure. The residue was subjected to purification by silica gel flash chromatography (elution by ethyl acetate-hexane: 0%-100%) using flash automatic purification device (Biotage AB/Isolera™) to obtain the subject compound (1.45 g, yield 83%).

$^1$H-NMR (CDCl$_3$/TMS δ (ppm) value): 1.61-1.84 (m, 2H), 2.08-2.22 (m, 2H), 2.24 (s, 3H), 2.29 (s, 3H), 2.82-2.89 (m, 1H), 3.13-3.33 (m, 2H), 3.68 (s, 2H), 3.87-3.90 (m, 1H), 4.74-4.78 (m, 1H), 6.96-6.98 (m, 2H), 7.07 (d, 1H), 8.09 (s, 1H), 9.99 (s, 1H).

[Example 18] Preparation of 4-(4-formyl-2-thiazolyl)-1-[2-(2,5-dichlorophenyl)acetyl]piperidine The product obtained in Step 1 of Example 17 above (1.1 g) was dissolved in dichloromethane (30 mL), to which 2,5-dichlorophenyl acetic acid (1.7 g) and 1-(3-dimethylaminopropyl)-3-ethyl carbodiimide hydrochloric acid salt (1.18 g) were added, and the mixture was reacted in the same manner as the preparation in Step 2 of Example 17, and then purified to obtain the subject compound (1.7 g, yield 79%).

$^1$H-NMR (CDCl$_3$/TMS δ (ppm) value): 1.74-1.85 (m, 2H), 2.20-2.23 (m, 2H), 2.85-2.92 (m, 1H), 3.22-3.37 (m, 2H), 3.81 (s, 2H), 3.94-4.02 (m, 1H), 4.69-4.73 (m, 1H), 7.20 (dd, 1H), 7.31-7.33 (m, 2H), 8.10 (s, 1H), 10.00 (s, 1H).

Same production methods were used to synthesize Compounds 1-2, 1-5 to 1-13, 1-15, 1-16, 2-2, 2-4 to 2-14, 2-16 to 2-22, 2-24 to 2-55, and 3-3 to 3-22 shown in [Table 1] to [Table 4].

TABLE 1

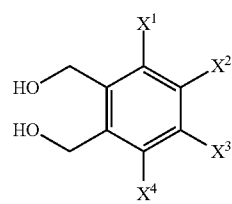

[1]

| No. | X$^1$ | X$^2$ | X$^3$ | X$^4$ |
|---|---|---|---|---|
| 1-1 | OSO$_2$Me | H | H | H |
| 1-2 | OSO$_2$Et | H | H | H |
| 1-3 | OSO$_2$Me | H | H | F |
| 1-4 | H | OSO$_2$Me | H | H |
| 1-5 | OSO$_2$c-Pr | H | H | H |
| 1-6 | OSO$_2$Me | H | H | Me |
| 1-7 | OSO$_2$n-Bu | H | H | H |
| 1-8 | OSO$_2$n-Pr | H | H | H |
| 1-9 | OSO$_2$n-C$_8$H$_{17}$ | H | H | H |
| 1-10 | OSO$_2$Me | H | H | OMe |
| 1-11 | OSO$_2$i-Pr | H | H | H |
| 1-12 | H | OSO$_2$Et | H | H |
| 1-13 | OSO$_2$CH$_2$CH$_2$CF$_3$ | H | H | H |
| 1-14 | OSO$_2$Me | H | H | NO$_2$ |
| 1-15 | OSO$_2$Me | F | H | H |
| 1-16 | OSO$_2$Me | H | Me | Me |
| 1-17 | OSO$_2$Me | H | H | Cl |
| 1-18 | OSO$_2$Me | H | H | Br |
| 1-19 | OSO$_2$Me | H | H | I |
| 1-20 | OSO$_2$Me | H | H | OSO$_2$Me |
| 1-21 | OSO$_2$Me | H | H | OCHF$_2$ |

TABLE 2

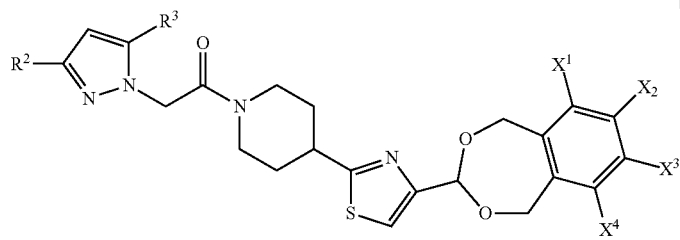

[5a]

| No. | R$^2$ | R$^3$ | X$^1$ | X$^2$ | X$^3$ | X$^4$ |
|---|---|---|---|---|---|---|
| 2-1 | CF$_3$ | Me | OSO$_2$Me | H | H | H |
| 2-2 | CF$_3$ | Me | OSO$_2$Et | H | H | H |
| 2-3 | CF$_3$ | Me | OSO$_2$Me | H | H | F |
| 2-4 | CF$_3$ | Me | H | OSO$_2$Me | H | H |
| 2-5 | CF$_3$ | Me | OSO$_2$c-Pr | H | H | H |
| 2-6 | CF$_3$ | Me | OSO$_2$Me | H | H | Me |
| 2-7 | CF$_3$ | Me | OSO$_2$n-Bu | H | H | H |
| 2-8 | CF$_3$ | Me | OSO$_2$n-Pr | H | H | H |
| 2-9 | CF$_3$ | Me | OSO$_2$n-C$_8$H$_{17}$ | H | H | H |
| 2-10 | CF$_3$ | Me | OSO$_2$Me | H | H | OMe |
| 2-11 | CF$_3$ | Me | OSO$_2$i-Pr | H | H | H |
| 2-12 | CF$_3$ | Me | H | OSO$_2$Et | H | H |
| 2-13 | CF$_3$ | Me | OSO$_2$CH$_2$CH$_2$CF$_3$ | H | H | H |

TABLE 2-continued

[5a]

| No. | R² | R³ | X¹ | X² | X³ | X⁴ |
|---|---|---|---|---|---|---|
| 2-14 | CF₃ | Me | OSO₂Me | H | H | NO₂ |
| 2-15 | CHF₂ | CHF₂ | OSO₂Me | H | H | H |
| 2-16 | CHF₂ | CHF₂ | OSO₂Me | H | H | OMe |
| 2-17 | CF₃ | CF₃ | OSO₂Me | H | H | H |
| 2-18 | CHF₂ | CHF₂ | OSO₂Me | H | H | Me |
| 2-19 | CF₃ | Me | OSO₂Me | F | H | H |
| 2-20 | CHF₂ | CHF₂ | OSO₂i-Pr | H | H | H |
| 2-21 | CHF₂ | CHF₂ | OSO₂n-Bu | H | H | H |
| 2-22 | CHF₂ | CHF₂ | OSO₂n-C₈H₁₇ | H | H | H |
| 2-23 | CHF₂ | CHF₂ | OSO₂Me | H | H | F |
| 2-24 | CF₃ | Me | OSO₂Me | H | Me | Me |
| 2-25 | CF₃ | Me | OSO₂Me | H | H | Cl |
| 2-26 | CF₃ | Me | OSO₂Me | H | H | Br |
| 2-27 | CF₃ | CF₃ | OSO₂i-Pr | H | H | H |
| 2-28 | CF₃ | CF₃ | OSO₂n-Bu | H | H | H |
| 2-29 | CF₃ | Me | OSO₂Me | H | H | I |
| 2-30 | CF₃ | Me | OSO₂Me | H | H | OSO₂Me |
| 2-31 | Me | Me | OSO₂Me | H | H | H |
| 2-32 | CF₃ | Cl | OSO₂Me | H | H | OMe |
| 2-33 | Cl | Cl | OSO₂Me | H | H | OMe |
| 2-34 | Me | Me | OSO₂Me | H | H | OMe |
| 2-35 | CHF₂ | CHF₂ | OSO₂Me | H | H | Cl |
| 2-36 | CF₃ | CF₃ | OSO₂Me | H | H | OMe |
| 2-37 | CF₃ | CF₃ | OSO₂Me | H | H | Cl |
| 2-38 | CHCl₂ | CHCl₂ | OSO₂Me | H | H | H |

TABLE 3

| No. | R² | R³ | X¹ | X² | X³ | X⁴ |
|---|---|---|---|---|---|---|
| 2-39 | Me | Me | OSO₂Me | H | H | F |
| 2-40 | CHF₂ | CHF₂ | OSO₂Me | H | Me | Me |
| 2-41 | CF₃ | CF₃ | OSO₂Me | H | Me | Me |
| 2-42 | CF₃ | CF₃ | OSO₂Me | H | H | Br |
| 2-43 | CHF₂ | CHF₂ | OSO₂Me | H | H | NO₂ |
| 2-44 | CHF₂ | CHF₂ | OSO₂Me | H | H | Br |
| 2-45 | CF₃ | CF₃ | OSO₂Me | H | H | NO₂ |
| 2-46 | CF₃ | CF₃ | OSO₂Me | H | H | I |
| 2-47 | CHF₂ | CHF₂ | OSO₂Me | H | H | I |
| 2-48 | CF₃ | CF₃ | OSO₂Me | F | H | H |
| 2-49 | CHF₂ | CHF₂ | OSO₂Me | F | H | H |
| 2-50 | CHF₂ | CHF₂ | H | OSO₂Me | H | H |
| 2-51 | CF₃ | CF₃ | H | OSO₂Me | H | H |
| 2-52 | CF₃ | Me | OSO₂Me | H | H | OCHF₂ |
| 2-53 | CHF₂ | CHF₂ | OSO₂Me | H | H | OSO₂Me |
| 2-54 | CF₃ | CF₃ | OSO₂Me | H | H | OSO₂Me |
| 2-55 | CHF₂ | Me | OSO₂Me | H | H | F |

TABLE 4

[5b]

| No. | R⁵ | R⁸ | X¹ | X² | X³ | X⁴ |
|---|---|---|---|---|---|---|
| 3-1 | Me | Me | OSO₂Me | H | H | H |
| 3-2 | Cl | Cl | OSO₂Me | H | H | H |

TABLE 4-continued

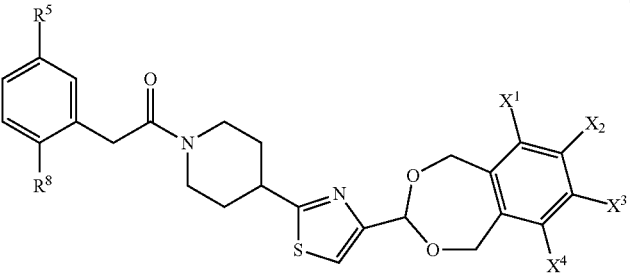

| No. | R⁵ | R⁸ | X¹ | X² | X³ | X⁴ |
|---|---|---|---|---|---|---|
| 3-3 | Me | Me | OSO₂Me | H | H | F |
| 3-4 | Me | Me | OSO₂n-Bu | H | H | H |
| 3-5 | Cl | Cl | OSO₂Me | H | H | F |
| 3-6 | Cl | Cl | OSO₂Me | H | H | OMe |
| 3-7 | Me | Me | OSO₂Me | H | H | OMe |
| 3-8 | CF₃ | CF₃ | OSO₂Me | H | H | H |
| 3-9 | Me | Me | OSO₂Me | H | Me | Me |
| 3-10 | Cl | Cl | OSO₂Me | H | Me | Me |
| 3-11 | Me | Me | OSO₂Me | H | H | Br |
| 3-12 | Cl | Cl | OSO₂Me | H | H | NO₂ |
| 3-13 | Cl | Cl | OSO₂Me | H | H | Br |
| 3-14 | Me | Me | OSO₂Me | H | H | NO₂ |
| 3-15 | Me | Me | OSO₂Me | H | H | Cl |
| 3-16 | Me | Me | OSO₂Me | H | H | I |
| 3-17 | Cl | Cl | OSO₂Me | H | H | Cl |
| 3-18 | Me | Me | OSO₂Me | F | H | H |
| 3-19 | Cl | Cl | OSO₂Me | F | H | H |
| 3-20 | Cl | Cl | OSO₂Me | H | H | I |
| 3-21 | Cl | Cl | H | OSO₂Me | H | H |
| 3-22 | Me | Me | OSO₂Me | H | H | OSO₂Me |

The $^1$H-NMR data (CDCl$_3$/TMS δ(ppm) value) of the compounds obtained by the aforementioned examples and the compounds produced by same processes shown in [Table 1] to [Table 4] is shown in [Table 5] to [Table 11].

TABLE 5

| No. | CDCl₃/TMS δ (ppm) |
|---|---|
| 1-1 | 3.11-3.33 (m, 5H), 4.81 (s, 4H), 7.25-7.28 (m, 1H), 7.37-7.40 (m, 2H) |
| 1-2 | 1.40 (s, 3H), 3.59 (q, 2H), 4.56 (d, 2H), 4.69 (d, 2H), 4.96 (t, 1H), 5.26 (t, 1H), 7.22 (d, 1H), 7.37 (t, 1H), 7.45 (d, 1H) |
| 1-3 | 3.27 (s, 3H), 3.53 (brs, 1H), 3.65 (brs, 1H), 4.80 (s, 2H), 4.84 (s, 2H), 7.11 (dd, 1H), 7.26-7.29 (m, 1H) |
| 1-4 | 2.63 (brs, 2H), 3.16 (s, 3H), 4.76 (s, 4H), 7.21-7.53 (m, 2H), 7.32 (s, 1H), 7.42 (d, 1H) |
| 1-5 | 1.21-1.26 (m, 2H), 1.34-1.37 (m, 2H), 2.72-2.77 (m, 1H), 3.27 (brs, 1H), 3.51 (brs, 1H), 4.78 (s, 2H), 4.95 (s, 2H), 7.29 (d, 1H), 7.35-7.40 (m, 2H) |
| 1-6 | 2.46 (s, 3H), 3.40 (s, 3H), 4.62 (dd, 4H), 4.92 (t, 1H), 5.00 (t, 1H), 7.20-7.23 (m, 2H) |
| 1-7 | 1.00 (t, 3H), 1.03-1.61 (m, 2H), 1.98-2.06 (m, 2H), 3.12 (t, 1H), 3.37-3.41 (m, 3H), 4.79 (dd, 4H), 7.22 (d, 1H), 7.35-7.40 (m, 2H) |
| 1-8 | 1.17 (t, 3H), 2.04-2.11 (m, 2H), 3.22 (t, 1H), 3.35-3.40 (m, 4H), 4.79 (d, 4H), 7.24 (d, 1H), 7.37-7.45 (m, 2H) |
| 1-9 | 0.89 (t, 3H), 1.25-1.40 (m, 6H), 1.48-1.56 (m, 2H), 1.59-1.63 (m, 2H), 2.00-2.07 (m, 2H), 3.19 (brs, 1H), 3.31-3.40 (m, 3H), 4.80 (s, 4H), 7.24 (d, 1H), 7.34-7.39 (m, 2H) |
| 1-10 | 3.39 (s, 3H), 3.81 (s, 3H), 4.63 (dd, 4H), 4.84 (t, 1H), 5.05 (t, 1H), 7.03 (d, 1H), 7.28 (d, 1H) |
| 1-11 | 1.62 (s, 3H), 1.64 (s, 3H), 3.18 (t, 1H), 3.34 (t, 1H), 3.59-3.66 (m, 1H), 4.79 (d, 4H), 7.23 (d, 1H), 7.35-7.40 (m, 2H) |
| 1-12 | 1.53 (t, 3H), 3.28 (q, 2H), 3.39 (brs, 1H), 3.52 (brs, 1H), 4.65 (s, 4H), 7.18 (d, 1H), 7.27 (s, 1H), 7.36 (d, 1H) |
| 1-13 | 2.53 (brs, 2H), 2.83-2.89 (m, 2H), 3.16-3.66 (m, 2H), 4.79 (d, 4H), 7.24-7.27 (m, 1H), 7.39-7.41 (m, 2H) |
| 1-14 | 3.05-3.12 (m, 2H), 3.36 (s, 3H), 4.91 (dd, 4H), 7.48 (d, 1H), 7.89 (d, 1H) |
| 1-15 | 3.14 (brs, 1H), 3.33 (m, 4H), 4.75 (s, 2H), 4.83 (s, 2H), 7.18 (dd, 1H), 7.35-7.39 (m, 1H) |
| 1-16 | 2.33 (s, 3H), 2.36 (s, 3H), 3.06 (brs, 1H), 3.17 (brs, 1H), 3.30 (s, 3H), 4.80-4.83 (m, 4H), 7.05 (d, 1H) |
| 1-17 | 2.57 (brs, 2H), 2.85 (s, 3H), 4.88 (s, 2H), 4.94 (s, 2H), 6.84 (d, 1H), 7.35 (d, 1H) |
| 1-18 | 2.10 (s, 2H), 3.29 (s, 3H), 4.86 (s, 2H), 5.01 (s, 2H), 7.17 (d, 1H), 7.64 (d, 1H) |
| 1-19 | 3.11-3.16 (m, 2H), 3.29 (s, 3H), 4.86 (d, 2H), 5.00 (d, 2H), 7.01 (d, 1H), 7.92 (d, 1H) |

TABLE 5-continued

| No. | CDCl$_3$/TMS δ (ppm) |
| --- | --- |
| 1-20 | 3.30-3.38 (m, 8H), 4.86 (d, 4H), 7.39 (s, 2H) |
| 1-21 | 3.27-3.30 (m, 5H), 4.82 (s, 2H), 4.86 (s, 2H), 6.57 (t, 1H), 7.22 (d, 1H), 7.31 (d, 1H) |

TABLE 6

| No. | CDCl$_3$/TMS δ (ppm) |
| --- | --- |
| 2-1 | 1.75 (m, 2H), 2.20 (m, 2H), 2.31 (s, 3H), 2.85 (t, 1H), 3.20 (s, 3H), 3.25-3.46 (m, 2H), 4.03 (d, 1H), 4.59 (d, 1H), 4.92-5.08 (m, 5H), 5.26 (d, 1H), 6.03 (s, 1H), 6.33 (s, 1H), 7.12 (m,1H), 7.21 (m, 2H) 7.39 (s, 1H) |
| 2-2 | 1.56 (t, 2H), 1.75 (m, 2H), 2.26 (m, 2H), 2.31 (s, 3H), 2.84 (t, 1H), 3.24-3.38 (m, 4H), 4.02 (d, 1H), 4.59 (d, 1H), 4.94-5.08 (m, 5H), 5.27 (d, 1H), 6.02 (s, 1H), 6.33 (s, 1H), 7.11 (d, 1H), 7.21 (m, 2H), 7.39 (s, 1H) |
| 2-3 | 1.75 (m, 2H), 2.21 (m, 2H), 2.31 (s, 3H), 2.85 (t, 1H), 3.20 (s, 3H), 3.23-3.48 (m, 2H), 4.03 (d, 1H), 4.59 (d, 1H), 4.96 (m, 4H), 5.20 (d, 2H), 6.03 (s, 1H), 6.33 (s, 1H), 6.99 (dd, 1H), 7.18 (dd, 1H), 7.40 (s, 1H) |
| 2-4 | 1.74 (m, 2H), 2.21 (m, 2H), 2.34 (s, 3H), 2.85 (t, 1H), 3.20 (s, 3H), 3.23-3.47 (m, 2H), 4.01 (d, 1H), 4.59 (d, 1H), 5.00 (m, 6H), 6.03 (s, 1H), 6.33 (s, 1H), 7.12 (m, 2H), 7.22 (m, 1H), 7.39 (s, 1H) |
| 2-5 | 1.16 (dd, 1H), 1.32 (dd, 1H), 1.78 (m, 2H), 2.21 (m, 2H), 2.32 (s, 3H), 2.65 (m, 1H), 2.85 (t, 1H), 3.27-3.37 (m, 2H), 4.03 (d, 1H), 4.60 (d, 1H), 5.06 (m, 5H), 5.31 (d, 1H), 6.33 (s, 1H), 6.33 (s, 1H), 7.11 (m, 1H), 7.25 (m, 2H), 7.38 (s, 1H) |
| 2-6 | 1.75 (m, 2H), 2.21 (m, 2H), 2.26 (s, 3H), 2.31 (s, 3H), 2.85 (t, 1H), 3.18 (s, 3H), 3.22-3.36 (m, 2H), 4.02 (d, 1H), 4.59 (d, 1H), 4.87-5.12 (m, 4H), 5.11 (d, 1H), 6.03 (s, 1H), 6.33 (s, 1H), 7.09 (s, 2H), 7.39 (s, 1H) |
| 2-7 | 0.99 (t, 3H), 1.54 (m, 2H), 1.77 (m, 2H), 1.99 (m, 2H), 2.21 (m, 2H), 2.32 (s, 3H), 2.85 (t, 1H), 3.24-3.37 (m, 4H), 4.03 (d, 1H), 4.60 (d, 1H), 4.94-5.08 (m, 5H), 5.26 (d, 1H), 6.03 (s, 1H), 6.33 (s, 1H), 7.11 (d, 1H), 7.20 (d, 1H), 7.24 (m, 1H), 7.39 (s, 1H) |
| 2-8 | 1.14 (t, 3H), 1.70 (m, 2H), 2.04 (m, 2H), 2.22 (m, 2H), 2.31 (s, 3H), 2.84 (t, 1H), 3.24-3.37 (m, 4H), 4.02 (d, 1H), 4.60 (d, 1H), 4.99-5.08 (m, 5H), 5.29 (d, 1H), 6.02 (s, 1H), 6.32 (s, 1H), 7.11 (d, 1H), 7.22 (m, 2H), 7.39 (s, 1H) |
| 2-9 | 0.89 (t, 3H), 1.31 (m, 8H), 1.51 (m, 2H), 1.77 (m, 2H), 2.00 (m, 2H), 2.22 (m, 2H), 2.32 (s, 3H), 2.85 (t, 1H), 3.25-3.39 (m, 4H), 4.04 (d, 1H), 4.60 (d, 1H), 4.94-5.08 (m, 5H), 5.27 (d, 2H), 6.03 (s, 1H), 6.34 (s, 1H), 7.11 (d, 1H), 7.21 (m, 2H), 7.39 (s, 1H) |
| 2-10 | 1.75 (m, 2H), 2.20 (m, 2H), 2.31 (s, 3H), 2.86 (t, 1H), 3.16 (s, 3H), 3.25-3.35 (m, 2H), 3.82 (s, 3H), 4.03 (d, 1H), 4.59 (d, 1H), 4.89-5.03 (m, 4H), 5.18 (m, 2H), 6.02 (s, 1H), 6.33 (s, 1H), 6.78 (d, 1H), 7.16 (d, 1H), 7.39 (m, 2H) |
| 2-11 | 1.56 (m, 6H), 1.77 (m, 2H), 2.26 (m, 2H), 2.31 (s, 3H), 2.85 (t, 1H), 3.27-3.38 (m, 2H), 3.54 (m, 1H), 4.02 (d, 1H), 4.60 (d, 1H), 4.93-5.08 (m, 5H), 5.28 (d, 1H), 6.02 (s, 1H), 6.33 (s, 1H) 7.09 (d, 1H), 7.21 (m, 2H), 7.39 (s, 1H) |
| 2-12 | 1.53 (t, 3H), 1.76 (m, 2H), 2.21 (m, 2H), 2.31 (s, 3H), 2.81 (t, 1H), 3.24-3.35 (m, 4H), 4.02 (d, 1H), 4.60 (d, 1H), 4.99 (m, 6H), 6.03 (s, 1H), 6.33 (s, 1H), 7.10 (m, 2H), 7.20 (d, 1H), 7.38 (s, 1H) |
| 2-13 | 1.76 (m, 2H), 2.26 (m, 2H), 2.32 (s, 3H), 2.85 (m, 3H), 3.24-3.36 (m, 2H), 3.55 (m, 1H), 4.04 (d, 1H), 4.60 (d, 1H), 4.93-5.05 (m, 5H), 5.23 (d, 1H), 6.03 (s, 1H), 6.33 (s, 1H), 7.16 (m, 2H), 7.29 (m, 1H), 7.39 (s, 1H) |
| 2-14 | 1.77 (m, 2H), 2.28 (m, 2H), 2.33 (s, 3H), 2.87 (t, 1H), 3.31 (s, 3H), 3.32 (m, 2H), 4.06 (d, 1H), 4.60 (d, 1H), 4.98-5.33 (m, 6H), 6.05 (s, 1H), 6.34 (s, 1H), 7.40 (m, 2H), 7.94 (d, 1H) |
| 2-15 | 1.78 (m, 2H), 2.25 (dd, 2H), 2.92 (t, 1H), 3.21 (s, 3H), 3.35 (m, 2H), 3.91 (d, 1H), 4.61 (d, 1H), 4.83 (d, 1H), 4.96-5.15 (m, 3H), 5.15 (d, 1H), 5.26 (d, 1H), 6.03 (s, 1H), 6.53-7.02 (m, 3H), 7.13 (d, 1H), 7.21 (m, 2H), 7.40 (s, 1H) |

TABLE 7

| No. | CDCl$_3$/TMS δ (ppm) |
| --- | --- |
| 2-16 | 1.83 (m, 2H), 2.24 (dd, 2H), 2.90 (t, 1H), 3.23 (s, 3H), 3.35 (m, 2H), 3.82 (s, 3H), 3.91 (d, 1H), 4.60 (d, 1H), 4.93 (t, 2H), 5.14-5.23 (m, 4H), 5.26 (d, 1H), 6.02 (s, 1H), 6.53-7.02 (m, 4H), 7.16 (d, 1H), 7.40 (s, 1H) |
| 2-17 | 1.79-1.88 (m, 2H), 2.21 (d, 2H), 2.30 (d, 2H), 2.90 (t, 1H), 3.21 (s, 3H), 3.29-3.38 (m, 2H), 3.85 (d, 1H), 4.59 (d, 1H), 4.99-5.09 (m, 3H), 5.19 (s, 2H), 5.26 (d, 1H), 6.03 (s, 1H), 6.95 (s, 1H), 7.13 (d, 1H), 7.20-7.27 (m, 1H), 7.40 (s, 1H) |
| 2-18 | 1.76-1.88 (m, 2H), 2.20-2.31 (m, 5H), 2.90 (t, 1H), 3.18 (s, 3H), 3.29-3.39 (m, 2H), 3.92 (d, 1H), 4.60 (d, 1H), 4.90 (d, 1H), 4.98 (d, 1H), 5.09-5.23 (m, 4H), 6.04 (s, 1H), 6.53-7.00 (m, 3H), 7.11 (s, 2H), 7.40 (s, 1H) |
| 2-19 | 1.74-1.80 (m, 2H), 2.17-2.27 (m, 2H), 2.32 (s, 3H), 2.86 (t, 1H), 3.24-3.36 (m, 5H), 4.03 (d, 1H), 4.59 (d, 1H), 4.90-5.04 (m, 5H), 5.28 (d, 1H), 6.02 (s, 1H), 6.33 (s, 1H), 7.07 (s, 2H), 7.39 (s, 1H) |
| 2-20 | 1.58 (d, 6H), 1.74-1.90 (m, 2H), 2.24 (dd, 2H), 2.88 (t, 1H), 3.21-3.29 (m, 2H), 3.49-3.60 (m, 1H), 3.90 (d, 1H), 4.57 (d, 1H), 4.93-5.08 (m, 3H), 5.14 (s, 2H), 5.28 (d, 1H), 6.03 (s, 1H), 6.53-7.11 (m, 3H), 7.19-7.25 (m, 2H), 7.40 (s, 1H) |

TABLE 7-continued

| No. | CDCl₃/TMS δ (ppm) |
|---|---|
| 2-21 | 0.99 (t, 3H), 1.48-1.56 (m, 2H), 1.82-1.90 (m, 2H), 1.92-2.04 (m, 2H), 2.22 (dd, 2H), 2.88 (t, 1H), 3.24-3.39 (m, 4H), 3.90 (d, 1H), 4.58 (d, 1H), 4.94-5.17 (m, 5H), 5.27 (d, 2H), 6.03 (s, 1H), 6.53-7.10 (m, 3H), 7.11 (d, 1H), 7.19-7.28 (m, 2H), 7.40 (s, 1H) |
| 2-22 | 0.89 (t, 3H), 1.22-1.39 (m, 8H), 1.43-1.52 (m, 2H), 1.74-1.90 (m, 2H), 1.95-2.04 (m, 2H), 2.24 (dd, 2H), 2.88 (t, 1H), 3.34-3.40 (m, 4H), 3.91 (d, 1H), 4.59 (d, 1H), 4.94-5.18 (m, 5H), 5.27 (d, 1H), 6.03 (s, 1H), 6.53-7.02 (m, 3H), 7.11 (d, 1H), 7.19-7.27 (m, 2H), 7.40 (s, 1H) |
| 2-23 | 1.78-1.88 (m, 2H), 2.25 (dd, 2H), 2.89 (t, 1H), 3.21 (s, 3H), 3.29-3.38 (m, 2H), 3.92 (d, 1H), 4.60 (d, 1H), 4.96 (dd, 2H), 5.14-5.22 (m, 4H), 6.03 (s, 1H), 6.53-6.98 (m, 3H), 7.01 (d, 1H), 7.18-7.21 (m, 1H), 7.41 (s, 1H) |
| 2-24 | 1.73-1.85 (m, 2H), 2.14 (s, 3H), 2.17-2.30 (m, 5H), 2.32 (s, 3H), 2.87 (t, 1H), 3.18 (s, 3H), 3.23-3.39 (m, 2H), 4.04 (d, 1H), 4.60 (d, 1H), 4.91-5.05 (m, 4H), 5.17 (dd, 2H), 6.02 (s, 1H), 6.34 (s, 1H), 7.02 (s, 1H), 7.38 (s, 1H) |
| 2-25 | 1.72-1.84 (m, 2H), 2.17-2.28 (m, 2H), 2.32 (s, 3H), 2.85 (t, 1H), 3.24-3.37 (m, 2H), 3.79 (s, 3H), 4.03 (d, 1H), 4.60 (d, 1H), 4.89-5.04 (m, 4H), 5.14 (dd, 2H), 6.03 (s, 1H), 6.33 (s, 1H), 6.71 (d, 1H), 7.19 (d, 1H), 7.39 (s, 1H) |
| 2-26 | 1.72-1.86 (m, 2H), 2.17-2.29 (m, 2H), 2.36 (s, 3H), 2.86 (t, 1H), 3.24 (s, 3H), 3.25-3.39 (m, 2H), 4.03 (d, 1H), 4.60 (d, 1H), 4.94-5.05 (m, 4H), 5.20 (dd, 2H), 6.03 (s, 1H), 6.33 (s, 1H), 7.09 (d, 1H), 7.40 (s, 1H), 7.48 (d, 1H) |
| 2-27 | 1.52-1.69 (m, 6H), 1.72-1.90 (m, 2H), 2.24 (dd, 2H), 2.89 (t, 1H), 3.24-3.40 (m, 2H), 3.53 (m, 1H), 3.84 (d, 1H), 4.59 (d, 1H), 4.93-5.33 (m, 6H), 6.03 (s, 1H), 6.95 (s, 1H), 7.10 (d, 1H), 7.17-7.30 (m, 2H), 7.40 (s, 1H) |
| 2-28 | 0.99 (t, 3H), 1.51-1.61 (m, 2H), 1.71-1.90 (m, 2H), 1.91-2.02 (m, 2H), 2.25 (dd, 2H), 2.89 (t, 1H), 3.27-3.40 (m, 4H), 3.53 (m, 1H), 3.84 (d, 1H), 4.60 (d, 1H), 4.96-5.31 (m, 6H), 6.03 (s, 1H), 6.95 (s, 1H), 7.11 (d, 1H), 7.20 (d, 1H), 7.22-7.28 (m, 1H), 7.40 (s, 1H) |
| 2-29 | 1.70-1.87 (m, 2H), 2.23 (m, 2H), 2.36 (s, 3H), 2.85 (t, 1H), 3.21 (s, 3H), 3.24-3.38 (m, 2H), 4.02 (d, 1H), 4.60 (d, 1H), 4.88-5.22 (m, 6H), 6.03 (s, 1H), 6.33 (s, 1H), 6.93 (d, 1H), 7.40 (s, 1H), 7.77 (d, 1H) |
| 2-30 | 1.73-1.85 (m, 2H), 2.22 (m, 2H), 2.32 (s, 3H), 2.86 (t, 1H), 3.23 (s, 6H), 3.27-3.36 (m, 2H), 4.03 (d, 1H), 4.59 (d, 1H), 4.97-5.01 (m, 4H), 5.22 (d, 2H), 6.02 (s, 1H), 6.33 (s, 1H), 7.27 (s, 2H), 7.39 (s, 1H) |
| 2-31 | 1.69-1.82 (m, 2H), 2.15-2.27 (m, 8H), 2.81 (t, 1H), 3.20 (s, 3H), 3.21-3.37 (m, 2H), 4.05 (d, 1H), 4.62 (d, 1H), 4.86-5.09 (m, 5H), 5.25 (d, 1H), 5.85 (s, 1H), 6.03 (s, 1H), 7.12 (d, 1H), 7.21-7.29 (m, 2H), 7.38 (s, 1H) |

TABLE 8

| | CDCl₃/TMS δ (ppm) |
|---|---|
| 2-32 | 1.75-1.94 (m, 2H), 2.25 (dd, 2H), 2.87 (t, 1H), 3.17 (s, 3H), 3.28-3.40 (m, 3H), 3.83 (s, 3H), 3.89 (d, 1H), 4.60 (d, 1H), 4.89-5.23 (m, 6H), 6.03 (s, 1H), 6.55 (s, 1H), 6.78 (d, 1H), 7.16 (d, 1H), 7.40 (s, 1H) |
| 2-33 | 1.74-1.91 (m, 2H), 2.24 (dd, 2H), 2.87 (t, 1H), 3.17 (s, 3H), 3.21-3.38 (m, 2H), 3.80-3.34 (m, 4H), 4.61 (d, 1H), 4.89-4.97 (m, 4H), 5.15-5.23 (m, 2H), 6.02 (s, 1H), 6.28 (s, 1H), 6.78 (d, 1H), 7.16 (d, 1H), 7.39 (s, 1H) |
| 2-34 | 1.68-1.83 (m, 2H), 2.15-2.24 (m, 8H), 2.79 (t, 1H), 3.16 (s, 3H), 3.20-3.37 (m, 2H), 3.82 (s, 3H), 4.06 (d, 1H), 4.61 (d, 1H), 4.86-4.97 (m, 4H), 5.14-5.22 (m, 2H), 5.85 (s, 1H), 6.02 (s, 1H), 6.78 (d, 1H), 7.16 (d, 1H), 7.38 (s, 1H) |
| 2-35 | 1.75-1.91 (m, 2H), 2.25 (dd, 2H), 2.89 (t, 1H), 3.21 (s, 3H), 3.24-3.39 (m, 2H), 3.91 (d, 1H), 4.59 (d, 1H), 4.96-5.03 (m, 2H), 5.11-5.27 (m, 4H), 6.03 (s, 1H), 6.53-7.02 (m, 3H), 7.16 (d, 1H), 7.30 (d, 1H), 7.40 (s, 1H) |
| 2-36 | 1.75-1.92 (m, 2H), 2.26 (dd, 2H), 2.91 (t, 1H), 3.17 (s, 3H), 3.29-3.39 (m, 2H), 3.82-3.87 (m, 4H), 4.58 (d, 1H), 4.89-4.97 (m, 2H), 5.14-5.23 (m, 4H), 6.03 (s, 1H), 6.78 (d, 1H), 6.95 (s, 1H), 7.17 (d, 1H), 7.40 (s, 1H) |
| 2-37 | 1.77-1.92 (m, 2H), 2.26 (dd, 2H), 2.91 (t, 1H), 3.21 (s, 3H), 3.30-3.38 (m, 2H), 3.85 (d, 1H), 4.59 (d, 1H), 4.96-5.03 (m, 2H), 5.14-5.30 (m, 4H), 6.04 (s, 1H), 6.96 (s, 1H), 7.16 (d, 1H), 7.31 (d, 1H), 7.42 (s, 1H) |
| 2-38 | 1.70-1.87 (m, 2H), 2.22 (m, 2H), 2.87 (t, 1H), 3.20 (s, 3H), 3.22-3.38 (m, 2H), 3.99 (d, 1H), 4.59 (d, 1H), 4.98-5.28 (m, 6H), 6.02 (s, 1H), 6.72 (s, 1H), 6.89 (s, 1H), 6.95 (s, 1H), 7.12 (d, 1H), 7.21-7.26 (m, 2H), 7.32-7.40 (m, 2H) |
| 2-39 | 1.69-1.80 (m, 2H), 2.14-2.26 (m, 8H), 2.81 (t, 1H), 3.20 (s, 3H), 3.22-3.38 (m, 2H), 4.07 (d, 1H), 4.63 (d, 1H), 4.83-4.99 (m, 4H), 5.17-5.21 (m, 2H), 5.85 (s, 1H), 6.03 (s, 1H), 7.00 (dd, 1H), 7.17-7.21 (m, 1H), 7.39 (s, 1H) |
| 2-40 | 1.75-1.90 (m, 2H), 2.11-2.37 (m, 8H), 2.89 (t, 1H), 3.17 (s, 3H), 3.27-3.39 (m, 2H), 3.91 (d, 1H), 4.59 (d, 1H), 4.91-4.97 (m, 2H), 5.11-5.21 (m, 4H), 6.03 (s, 1H), 6.53-6.88 (m, 3H), 7.02 (s, 1H), 7.39 (s, 1H) |
| 2-41 | 1.76-1.91 (m, 2H), 2.16-2.35 (m, 8H), 2.90 (t, 1H), 3.18 (s, 3H), 3.32-3.39 (m, 2H), 3.85 (d, 1H), 4.59 (d, 1H), 4.92-4.97 (m, 2H), 5.15-5.24 (m, 4H), 6.03 (s, 1H), 6.95 (s, 1H), 7.02 (s, 1H), 7.40 (s, 1H) |
| 2-42 | 1.75-1.91 (m, 2H), 2.26 (dd, 2H), 2.88 (t, 1H), 3.22 (s, 3H), 3.28-3.40 (m, 2H), 3.86 (d, 1H), 4.59 (d, 1H), 4.99 (d, 2H), 5.19-5.24 (m, 4H), 6.04 (s, 1H), 6.96 (s, 1H), 7.10 (d, 1H), 7.42 (s, 1H), 7.50 (d, 1H) |
| 2-43 | 1.70-1.93 (m, 2H), 2.25 (dd, 2H), 2.89 (t, 1H), 3.27-3.40 (m, 5H), 3.91 (d, 1H), 4.59 (d, 1H), 5.00-5.32 (m, 6H), 6.04 (s, 1H), 6.52-6.87 (m, 3H), 7.37-7.43 (m, 2H), 7.92 (m, 1H) |

TABLE 8-continued

| | CDCl₃/TMS δ (ppm) |
|---|---|
| 2-44 | 1.72-1.90 (m, 2H), 2.25 (dd, 2H), 2.89 (t, 1H), 3.21 (s, 3H), 3.25-3.38 (m, 2H), 3.91 (d, 1H), 4.59 (d, 1H), 4.98 (d, 2H), 5.11-5.23 (m, 4H), 6.03 (s, 1H), 6.53-7.02 (m, 3H), 7.09 (d, 1H), 7.41 (s, 1H), 7.48 (d, 1H) |
| 2-45 | 1.74-1.94 (m, 2H), 2.26 (dd, 2H), 2.92 (t, 1H), 3.30-3.41 (m, 5H), 3.86 (d, 1H), 4.59 (d, 1H), 5.01-5.32 (m, 6H), 6.05 (s, 1H), 6.96 (s, 1H), 7.40 (s, 1H), 7.43 (d, 1H), 7.93 (d, 1H) |
| 2-46 | 1.76-1.93 (m, 2H), 2.26 (dd, 2H), 2.91 (t, 1H), 3.21 (s, 3H), 3.30-3.40 (m, 2H), 3.86 (d, 1H), 4.59 (d, 1H), 4.90-5.27 (m, 6H), 6.04 (s, 1H), 6.93-6.96 (m, 2H), 7.42 (s, 1H), 7.78 (d, 1H) |
| 2-47 | 1.74-1.92 (m, 2H), 2.25 (dd, 2H), 2.89 (t, 1H), 3.21 (s, 3H), 3.22-3.39 (m, 2H), 3.91 (d, 1H), 4.59 (d, 1H), 4.89-5.00 (m, 2H), 5.09-5.22 (m, 2H), 6.03 (s, 1H), 6.53-7.02 (m, 4H), 7.41 (s, 1H), 7.78 (d, 1H) |

TABLE 9

| No. | CDCl₃/TMS δ (ppm) |
|---|---|
| 2-48 | 1.73-1.92 (m, 2H), 2.26 (dd, 2H), 2.90 (t, 1H), 3.25-3.40 (m, 5H), 3.85 (d, 1H), 4.58 (d, 1H), 4.91-5.31 (m, 6H), 6.02 (s, 1H), 6.95 (s, 1H), 7.07 (m, 2H), 7.40 (s, 1H) |
| 2-49 | 1.75-1.91 (m, 2H), 2.24 (dd, 2H), 2.89 (t, 1H), 3.25-3.38 (m, 5H), 3.91 (d, 1H), 4.58 (d, 1H), 4.91-5.30 (m, 6H), 6.02 (s, 1H), 6.53-7.01 (m, 3H), 7.07 (m, 2H), 7.39 (s, 1H) |
| 2-50 | 1.72-1.90 (m, 2H), 2.24 (dd, 2H), 2.87 (t, 1H), 3.14-3.36 (m, 2H), 3.91 (d, 1H), 4.60 (d, 1H), 4.94-5.14 (m, 6H), 6.03 (s, 1H), 6.67-7.02 (m, 3H), 7.11-7.23 (m, 3H), 7.39 (s, 1H) |
| 2-51 | 1.72-1.89 (m, 2H), 2.25 (dd, 2H), 2.88 (t, 1H), 3.32-3.40 (m, 2H), 3.85 (d, 1H), 4.59 (d, 1H), 4.95-5.06 (m, 4H), 5.18 (s, 2H), 6.04 (s, 1H), 6.95 (s, 1H), 7.12-7.23 (m, 3H), 7.40 (s, 1H) |
| 2-52 | 1.75-1.85 (m, 2H), 2.23 (m, 2H), 2.32 (s, 3H), 2.86 (t, 1H), 3.22 (s, 3H), 3.24-3.39 (m, 2H), 4.04 (d, 1H), 4.60 (d, 1H), 4.94-5.04 (m, 4H), 5.20 (d, 2H), 6.02 (s, 1H), 6.32-6.68 (m, 2H), 7.07 (d, 1H), 7.22 (d, 1H), 7.39 (s, 1H) |
| 2-53 | 1.75-1.90 (m, 2H), 2.25 (dd, 2H), 2.90 (t, 1H), 3.24 (s, 6H), 3.27-3.38 (m, 2H), 3.92 (d, 1H), 4.59 (d, 1H), 5.00 (d, 2H), 5.14-5.21 (m, 4H), 6.02 (s, 1H), 6.53-6.72 (m, 4H), 7.27 (m, 1H), 7.40 (s, 1H) |
| 2-54 | 1.75-1.92 (m, 2H), 2.25 (dd, 2H), 2.91 (t, 1H), 3.24 (s, 6H), 3.29-3.38 (m, 2H), 3.84 (d, 1H), 4.56 (d, 1H), 5.00 (d, 2H), 5.19-5.25 (m, 4H), 6.02 (s, 1H), 7.27 (m, 2H), 7.41 (s, 1H) |
| 2-55 | 1.74-1.83 (m, 2H), 2.22 (m, 2H), 2.30 (s, 3H), 2.86 (t, 1H), 3.20 (s, 3H), 3.22-3.37 (m, 2H), 4.03 (d, 1H), 4.61 (d, 1H), 4.90-5.07 (m, 4H), 5.19 (d, 2H), 6.03 (s, 1H), 6.29 (s, 1H), 6.62 (t, 1H), 6.99 (dd, 1H), 7.17-7.27 (m, 1H), 7.39 (s, 1H) |

TABLE 10

| No. | CDCl₃/TMS δ (ppm) |
|---|---|
| 3-1 | 1.60 (m, 1H), 1.74 (m, 1H), 2.10 (m, 1H), 2.19 (m, 1H), 2.24 (s, 3H), 2.34 (s, 3H), 2.79 (t, 1H), 3.14 (m, 1H), 3.19 (s, 3H), 3.28 (m, 1H), 3.67 (s, 2H), 3.87 (d, 1H), 4.77 (d, 1H), 4.94-5.08 (m, 3H), 5.25 (d, 1H), 6.02 (s, 1H), 6.96 (m, 2H), 7.06 (d, 1H), 7.09 (d, 1H), 7.21 (m, 2H), 7.37 (s, 1H) |
| 3-2 | 1.66-1.81 (m, 2H), 2.20 (d, 2H), 2.83 (t, 1H), 3.20 (s, 3H), 3.16-3.24 (m, 2H), 3.81 (s, 2H), 3.96 (d, 1H), 4.72 (d, 1H), 4.95-5.28 (m, 3H), 5.26 (d, 1H), 6.03 (s, 1H), 7.12 (d, 1H), 7.14-7.32 (m, 2H), 7.38 (s, 1H) |
| 3-3 | 1.54-1.82 (m, 2H), 2.14 (dd, 2H), 2.24 (s, 3H), 2.29 (s, 3H), 2.80 (t, 1H), 3.15 (t, 1H), 3.20 (s, 3H), 3.24-3.32 (m, 1H), 3.67 (s, 2H), 3.87 (d, 1H), 4.77 (d, 1H), 4.93 (dd, 2H), 5.18 (dd, 2H), 6.02 (s, 1H), 6.96-6.99 (m, 3H), 7.06 (d, 1H), 7.15-7.19 (m, 1H), 7.38 (s, 1H) |
| 3-4 | 0.99 (t, 1H), 1.50-1.82 (m, 4H), 1.95-2.04 (m, 2H), 2.14 (dd, 2H), 2.24 (s, 3H), 2.29 (s, 3H), 2.79 (t, 1H), 3.14 (t, 1H), 3.23-3.34 (m, 3H), 3.67 (s, 2H), 3.87 (d, 1H), 4.78 (d, 1H), 4.93-5.07 (m, 3H), 5.06 (d, 1H), 6.02 (s, 1H), 6.96-6.98 (m, 2H), 7.05-7.11 (m, 2H), 7.19-7.26 (m, 2H), 7.37 (s, 1H) |
| 3-5 | 1.68-1.83 (m, 2H), 2.19 (d, 2H), 2.83 (t, 1H), 3.20-3.37 (m, 5H), 3.81 (s, 2H), 3.96 (d, 1H), 4.72 (d, 1H), 4.95 (dd, 1H), 5.19 (d, 1H), 6.03 (s, 1H), 7.00 (dd, 1H), 7.17-7.19 (m, 1H), 7.30-7.33 (m, 2H), 7.39 (s, 1H) |
| 3-6 | 1.65-1.81 (m, 2H), 2.20 (d, 2H), 2.83 (t, 1H), 3.19 (s, 3H), 3.20-3.35 (m, 2H), 3.82 (s, 2 + 3H), 3.96 (d, 1H), 4.72 (d, 1H), 4.93 (dd, 2H), 5.18 (dd, 2H), 6.02 (s, 1H), 6.68 (d, 1H), 7.15-7.21 (m, 2H), 7.30-7.32 (m, 2H), 7.38 (s, 1H) |
| 3-7 | 1.56-1.81 (m, 2H), 2.14 (d, 2H), 2.24 (s, 3H), 2.29 (s, 3H), 2.80 (t, 1H), 3.19 (s, 3H), 3.12-3.37 (m, 2H), 3.67 (s, 2H), 3.81-3.88 (m, 4H), 4.77 (d, 1H), 4.92 (dd, 2H), 5.17 (dd, 2H), 6.01 (s, 1H), 6.77 (d, 1H), 6.96 (m, 2H), 7.06 (d, 1H), 7.16 (d, 1H), 7.37 (s, 1H) |
| 3-8 | 1.70-1.81 (m, 2H), 2.20 (m, 2H), 2.84 (t, 1H), 3.20-3.37 (m, 5H), 3.90-4.01 (m, 3H), 4.70 (d, 1H), 4.95-5.28 (m, 3H), 5.26 (d, 1H), 6.03 (s, 1H), 7.12 (d, 1H), 7.21-7.28 (m, 2H), 7.39 (s, 1H), 7.65 (m, 2H), 7.80 (d, 1H) |
| 3-9 | 1.55-1.80 (m, 2H), 2.09-2.37 (m, 14H), 2.80 (t, 1H), 3.10-3.32 (m, 5H), 3.67 (s, 2H), 3.88 (d, 1H), 4.78 (d, 1H), 4.91 (dd, 2H), 5.16 (d, 2H), 6.01 (s, 1H), 6.97 (d, 2H), 7.02 (s, 1H), 7.06 (d, 1H), 7.36 (s, 1H) |

TABLE 10-continued

| No. | CDCl$_3$/TMS δ (ppm) |
| --- | --- |
| 3-10 | 1.63-1.84 (m, 2H), 2.09-2.24 (m, 5H), 2.29 (s, 3H), 2.83 (t, 1H), 3.15-3.37 (m, 5H), 3.80 (s, 2H), 3.96 (d, 1H), 4.71 (d, 1H), 4.94 (dd, 2H), 5.17 (d, 2H), 6.02 (s, 1H), 7.02 (s, 1H), 7.19 (d, 1H), 7.30-7.32 (d, 2H), 7.37 (s, 1H) |
| 3-11 | 1.53-1.80 (m, 2H), 2.14 (dd, 2H), 2.24 (s, 3H), 2.29 (s, 3H), 2.80 (t, 1H), 3.14-3.32 (m, 5H), 3.89 (s, 2H), 3.87 (d, 1H), 4.78 (d, 1H), 4.98 (d, 2H), 5.19 (dd, 2H), 6.02 (s, 1H), 6.97 (d, 2H), 7.08 (m, 2H), 7.38 (s, 1H), 7.49 (d, 1H) |
| 3-12 | 1.65-1.83 (m, 2H), 2.21 (d, 2H), 2.84 (t, 1H), 3.20-3.37 (m, 5H), 3.81 (s, 2H), 3.97 (d, 1H), 4.72 (d, 1H), 5.10 (dd, 2H), 5.25 (dd, 2H), 6.05 (s, 1H), 7.19 (d, 1H), 7.31 (m, 2H), 7.40 (s, 2H), 7.93 (d, 1H) |
| 3-13 | 1.67-1.84 (m, 2H), 2.20 (d, 2H), 2.83 (t, 1H), 3.21-3.38 (m, 5H), 3.80 (s, 2H), 3.97 (d, 1H), 4.71 (d, 1H), 4.98 (d, 2H), 5.19 (dd, 2H), 6.03 (s, 1H), 7.09 (d, 1H), 7.18 (d, 1H), 7.31 (m, 2H), 7.40 (s, 1H), 7.49 (d, 1H) |
| 3-14 | 1.58-1.81 (m, 2H), 2.16 (dd, 2H), 2.24 (s, 3H), 2.29 (s, 3H), 2.81 (t, 1H), 3.15 (t, 1H), 3.67 (s, 2H), 3.88 (d, 1H), 4.77 (d, 1H), 5.10 (dd, 2H), 5.25 (dd, 2H), 6.04 (s, 1H), 6.97 (d, 2H), 7.07 (d, 1H), 7.39 (m, 2H), 7.93 (d, 1H) |
| 3-15 | 1.55-1.80 (m, 2H), 2.15 (dd, 2H), 2.24 (s, 3H), 2.29 (s, 3H), 2.80 (t, 1H), 3.11-3.31 (m, 5H), 3.67 (s, 2H), 3.68 (d, 1H), 4.97 (d, 1H), 4.99 (dd, 2H), 5.20 (dd, 2H), 6.02 (s, 1H), 6.97 (d, 2H), 7.07 (d, 1H), 7.15-7.18 (m, 2H), 7.30 (d, 1H), 7.38 (s, 1H) |

TABLE 11

| No. | CDCl$_3$/TMS δ (ppm) |
| --- | --- |
| 3-16 | 1.53-1.80 (m, 2H), 2.14 (dd, 2H), 2.24 (s, 3H), 2.29 (s, 3H), 2.80 (t, 1H), 3.14-3.34 (m, 5H), 3.67 (s, 2H), 3.87 (d, 1H), 4.78 (d, 1H), 4.97 (dd, 2H), 5.14 (dd, 2H), 6.02 (s, 1H), 6.93-7.00 (m, 3H), 7.06 (d, 1H), 7.38 (s, 1H), 7.78 (d, 1H) |
| 3-17 | 1.64-1.82 (m, 2H), 2.21 (dd, 2H), 2.83 (t, 1H), 3.17-3.36 (m, 5H), 3.81 (s, 2H), 3.96 (d, 1H), 4.72 (d, 1H), 5.00 (dd, 2H), 5.21 (dd, 2H), 6.03 (s, 1H), 7.16-7.21 (m, 2H), 7.30-7.33 (m, 3H), 7.39 (s, 1H) |
| 3-18 | 1.54-1.80 (m, 2H), 2.14 (dd, 2H), 2.24 (s, 3H), 2.29 (s, 3H), 2.80 (t, 1H), 3.13 (t, 1H), 3.24-3.33 (m, 4H), 3.67 (s, 2H), 3.86 (d, 1H), 4.77 (d, 1H), 4.91 (d, 1H), 5.02 (d, 2H), 5.27 (d, 1H), 6.01 (s, 1H), 6.97 (d, 2H), 7.07 (m, 3H), 7.37 (s, 1H) |
| 3-19 | 1.67-1.83 (m, 2H), 2.20 (d, 2H), 2.83 (t, 1H), 3.19-3.35 (m, 5H), 3.80 (s, 2H), 3.96 (d, 1H), 4.71 (d, 1H), 4.92 (d, 1H), 5.02 (d, 2H), 5.27 (d, 1H), 6.02 (s, 1H), 7.07 (d, 2H), 7.18 (d, 1H), 7.30-7.33 (m, 2H), 7.38 (s, 1H) |
| 3-20 | 1.65-1.83 (m, 2H), 2.20 (d, 2H), 2.83 (t, 1H), 3.20-3.38 (m, 5H), 3.81 (s, 2H), 3.97 (d, 1H), 4.72 (d, 1H), 4.94 (dd, 2H), 5.15 (dd, 2H), 6.03 (s, 1H), 6.94 (d, 1H), 7.20 (d, 1H), 7.30-7.33 (m, 2H), 7.40 (s, 1H), 7.78 (d, 1H) |
| 3-21 | 1.67-1.80 (m, 2H), 2.19 (d, 2H), 2.82 (t, 1H), 3.14 (s, 3H), 3.19-3.34 (m, 2H), 3.80 (s, 2H), 3.95 (d, 1H), 4.72 (d, 1H), 4.99 (dd, 4H), 6.03 (s, 1H), 7.11-7.18 (m, 2H), 7.20 (d, 2H), 7.32 (d, 2H), 7.38 (s, 1H) |
| 3-22 | 1.55-1.80 (m, 2H), 2.14 (d, 2H), 2.24 (s, 3H), 2.29 (s, 3H), 2.80 (t, 1H), 3.14 (t, 1H), 3.21-3.32 (m, 7H), 3.67 (s, 2H), 3.87 (d, 1H), 4.76 (d, 1H), 4.98 (d, 2H), 5.21 (d, 2H), 6.01 (s, 1H), 6.97 (d, 2H), 7.06 (s, 1H), 7.27 (m, 2H), 7.38 (s, 1H) |

Next, the working examples of using the compounds of the present invention are shown below.

(1) Implementation procedure for formulation

<Formulation Example 1> Wettable powder

The compound of the present invention (10 parts), sodium lauryl sulfate (2 parts), sodium lignin sulfonate (4 parts), white carbon (20 parts) and clay (64 parts) were mixed and ground to obtain 10% wettable powder.

<Formulation Example 2> Floable agent

The compound of the present invention (10 parts), polyoxyethylene allyl phenyl ether sulfate (4 parts), polyoxyethylene alkyl ether (5 parts), propylene glycol (5 parts), silicon antifoam agent (0.2 part), sodium montmorillonite (0.8 part), and water (50 parts) were added and mixed, and then subjected to wet grinding using a Dyno-Mill to obtain a ground suspension.

To 75 parts of the ground suspension were added a xanthan gum solution (10 parts) and water (15 parts), the xanthan gum solution containing xanthan gum (0.2 part) and 2-benzisothiazolin-3-one (0.1 part), and the mixture was mixed to obtain a 10% aqueous suspension-type pesticide composition.

<Formulation Example 3> Emulsifiable Concentrate

The compound of the present invention (10 parts), calcium dodecylbenzene sulfonate (2 parts), and castor oil ethoxylates (15 parts) were dissolved by mixing with an aromatic hydrocarbon mixture (73 parts) to obtain a homogenous 10% emulsifiable oil liquid.

<Formulation Example 4> Granular Wettable Powder

The compound of the present invention (10 parts), sodium lignin sulfonate (20 parts), sodium salt of naphthalene-sulfonate condensate (10 parts), sodium alkylbenzene sulfonate (3 parts), silicon antifoam agent (0.5 part), diatomite (5 parts), ammonium sulfate (10 parts), talc (10 parts), and the clay section (31.5 parts) were added and subjected to full stirring/mixing and grinding to obtain a ground product. A suitable amount of water was added as necessary to the ground product, and the product was granulated by a granulator and dried, then sifted, to obtain a 10% hydration particle.

<Formulation Example 5> Emulsion

The compound of the present invention (10 parts), an aromatic hydrocarbon mixture (15 parts), calcium dodecylbenzene sulfonate (2 parts), and polyoxyethylene castor oil (20 parts) and propylene glycol (4 parts) were added and dissolved to obtain a mixture. The mixture was added to water (49 parts) to obtain a homogenous 10% emulsifed liquid using a homogenizer.

<Formulation Example 6> Granule

After the compound of the present invention (10 parts), polycarboxylic acid anion surfactant (3 parts), sodium dioctyl sulfosuccinate (0.2 part), dextrin (2 parts), sodium bentonite (15 parts), and calcium carbonate (69.8 parts) were added and mixed homogenously, a suitable amount of water was added and the mixture was kneaded to be subjected to extrusion granulation by a basket type granulator. The mixture was dried and sifter to obtain a 10% particle.

<Formulation Example 7> Microemulsion

The compound of the present invention (10 parts), fatty acid dimethylamide (12 parts), cyclohexanone (10 parts), and aryl phenol ethoxylate (15 parts) were mixed together, to which alcohol ethoxylate (10 parts) and water (43 parts) were added, and the mixture was stirred for a few minutes under heat to obtain a stable 10% aqueous liquid.

(2) Implementation Procedure to Prepare Test Suspension

A 10% wettable powder prepared according to Formulation Example 1 was diluted by a Teen20 solution adjusted to a concentration of 1/5000, and the compound represented by Formula [1] was adjusted to a concentration of 4 ppm. Further, the compound represented by Formula [1] was adjusted to a concentration of 1000 ppm in Test 4.

(3) Assessment Test Procedure of Control Effect Against Plant Disease

<Test 1 Test of Control Effect Against Tomato Blight>

A test suspension was sprayed onto tomato at leaf stage 5 (Variety: Regina) in an amount of 20 ml per seedling. One day after spraying, a zoospore suspension of *Phytophthora infestans* adjusted to $1.0 \times 10^5$ units/ml was applied by spraying and incubated for 16 h. in a moist chamber adjusted to 22° C. Then, the plants were made to contract the disease in the chamber, and the rate of lesion area on the leaf 4 days after application was investigated and the control value was calculated using the following formula.

Calculation formula of control value: Control Value={1−Disease area rate of the leaf on which the test agent was applied/Untreated disease area rate}×100

<Test 2 Test of Control Effect Against of Downy Mildew of Cucumber>

A test suspension was sprayed onto cucumber at leaf stage 2 (Variety: Sagami Hanjiro) in an amount of 20 ml per seedling. One day after spraying, a zoospore suspension of *Pseudoperonospora cubensis* adjusted to $1.0 \times 10^4$ units/ml was applied by spraying and incubated for 16 h. in a moist chamber adjusted to 22° C. Then, the plants were made to contract the disease in the chamber, and the rate of lesion area on the leaf 5 days after application was investigated and the control value was calculated using the following formula.

Calculation formula of control value: Control Value={1−Disease area rate of the leaf on which the test agent was applied/Untreated disease area rate}×100

<Test 3 Test of Control Effect Against Downy Mildew of Grape>

A test suspension was sprayed onto grape (Variety: Neomuscat) seedling in an amount of 20 ml per seedling. One day after spraying, a zoospore suspension of *Plasmopara viticola* adjusted to $1.0 \times 10^4$ units/ml was applied by spraying and incubated for 16 h. in a moist chamber adjusted to 22° C. Then, the plants were made to contract the disease in the chamber, and the rate of lesion area on the leaf 5 days after application was investigated and the control value was calculated using the following formula.

Calculation formula of control value: Control Value={1−Disease area rate of the leaf on which the test agent was applied/Untreated disease area rate}×100

<Test 4 Test of Control Effect Against Damping-Off Disease of Rice by *Pythium* Bacteria (Soil Irrigation)>

Distilled water was added to a bacterial flora of *Pythium graminicola* cultured in a bentgrass seed medium, and the mixture was stirred in a mixer to prepare contaminated soil by mixing the bacteria in the soil so that 5 g of bacteria exists for 1 kg of soil.

Contaminated soil was loaded into cell trays holding cells at the size of $31 \times 31$ mm² each, at 20 ml per tray, and rice chaffs that were forced to sprout (Variety: Koshihikari) was seeded at a rate of 3 seeds per cell, then a soil cover of 5 ml was added, and 2.5 ml of test suspension was irrigated, and was incubated for 72 h. in a moist chamber adjusted to 28° C. for budding treatment. Then, the plants were made to contract the disease for 2 days in the low temperature chamber of 5° C. and the disease was nurtured in a hothouse adjusted to 25° C. for 14 days.

The soil was washed off, and the dead strain, growth regulated strain, and a healthy strain were measured, and the degree of disease development was calculated.

Degree of disease development=[Σ(Number of diseased strain by level×Disease development index)/(Investigated strain×3)]×100

[Disease Development Index]
0: Healthy strain
1: Growth regulated strain
3: Dead strain The control value was calculated using the following formula based on the degree of disease development.

Calculation formula of control value: Control Value={1−Degree of disease development of the leaf on which the test agent was applied/ Degree of disease development of untreated section}×100

(4) Analysis Test Result of Control Effect Against Plant Disease<Test 1> to <Test 4>

As a result of performing Test 1, the following compounds showed a control value of 80 or higher:
No. 2-1 to 2-55, 3-1 to 3-7, 3-10, 3-12 to 3-15, 3-17 to 3-22.

As a result of performing Test 2, the following compounds showed a control value of 80 or higher:
No. 2-1 to 2-55, 3-1 to 3-20, 3-22.

As a result of performing Test 3, the following compounds showed a control value of 80 or higher:
No. 2-1 to 2-53, 2-55, 3-1 to 3-22.

As a result of performing Test 4 for a few compounds, the following compounds showed a control value of 90 or higher. The Compound No. are shown below:
No. 2-1, 2-7, 2-8, 2-14, 2-18, 2-19, 2-23, 2-33, 2-34, 2-38, 2-42, 2-46, 2-48, 2-49, 2-54, 3-1, 3-2, 3-4, 3-8, 3-9, 3-19, 3-20.

The invention claimed is:

1. A process for preparing a compound represented by Formula [1]:

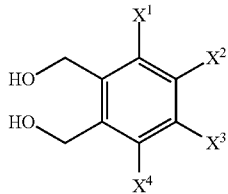

[1]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —OS(O)$_2$R$^1$;
at least one of $X^1$, $X^2$, $X^3$ and $X^4$ is —OS(O)$_2$R$^1$; and
$R^1$ is $C_1$-$C_8$ alkyl, C1-$C_8$ haloalkyl or $C_3$-$C_6$ cycloalkyl;
the process comprising:
a step of hydrolyzing a compound represented by Formula [2] under an acidic or basic condition:

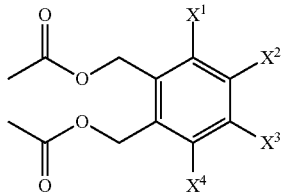

[2]

wherein, $X^1$, $X^2$, $X^3$ and $X^4$ are as defined for Formula [1].

2. The process according to claim 1, wherein the basic condition is provided by a metal carbonate salt.

3. The process according to claim 1, further comprising a step of reacting a compound represented by Formula [3] with a metal acetate salt:

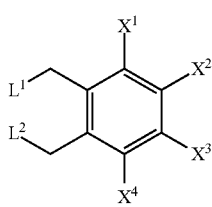

[3]

wherein, $X^1$, $X^2$, $X^3$ and $X^4$ are as defined in claim 1, and $L^1$ and $L^2$ are each independently a halogen atom, to prepare the compound represented by Formula [2].

4. A process for preparing a compound represented by Formula [2]:

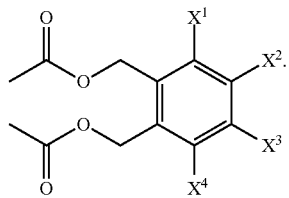

[2]

the process comprising:
a step of reacting a compound represented by Formula [3] with a metal acetate salt:

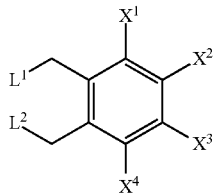

[3]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —OS(O)$_2$R$^1$;
at least one of $X^1$, $X^2$, $X^3$ and $X^4$ is —OS(O)$_2$R$^1$,
and $R^1$ is $C_1$-$C_8$ alkyl, $C_1$-$C_8$ haloalkyl or $C_3$-$C_6$ cycloalkyl; and $L^1$ and $L^2$ are each independently a halogen atom.

5. The process according to claim 3, further comprising a step of halogenating a compound represented by Formula [4]:

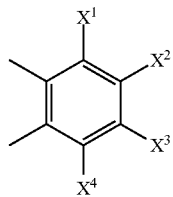

[4]

wherein, $X^1$, $X^2$, $X^3$ and $X^4$ are each independently a hydrogen atom $C_1$-$C_4$ alkyl, $C_1$-$C_4$ alkoxy, $C_1$-$C_4$ haloalkoxy, nitro, a halogen atom or —OS(O)$_2$R$^1$;
at least one of $X^1$, $X^2$, $X^3$ and $X^4$ is —OS(O)$_2$R$^1$; and
$R^1$ is $C_1$-$C_8$ alkyl, $C_1$-$C_8$ haloalkyl or $C_3$-$C_6$ cycloalkyl;
to prepare the compound represented by Formula [3].

6. A process for preparing a compound represented by Formula [3]:

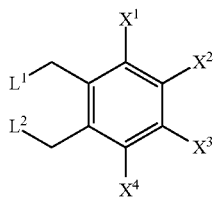

[3]

wherein $L^1$ and $L^2$ are each independently a halogen atom,
the process comprising:
a step of halogenating a compound represented by Formula [4]:

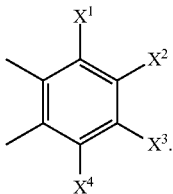

[4]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —$OS(O)_2R^1$,
at least one of $X^1$, $X^2$, $X^3$ and $X^4$ is —$OS(O)_2R^1$, and
$R^1$ is $C_1$-$C_8$ alkyl, $C_1$-$C_8$ haloalkyl or $C_3$-$C_6$ cycloalkyl.

7. The process according to claim 5, wherein a halogenation reagent for the halogenation reaction is a chlorination reagent such as chlorine, sulfuryl chloride, N-chlorosuccinimide, or a bromination reagent such as bromine, N-bromosuccinimide.

8. The process according to claim 1, which is a process for preparing the compound represented by Formula [1] comprising a step of reacting the compound represented by Formula [3] with a metal acetate salt to obtain the compound represented by Formula [2], and hydrolyzing the compound represented by Formula [2] without isolating the compound represented by Formula [2] under a basic condition to obtain the compound represented by Formula [1].

9. A process for preparing a compound represented by Formula [1]:

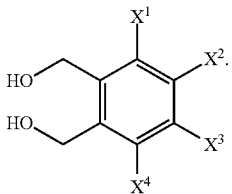

[1]

the process comprising:
a step of reacting a compound represented by Formula [3] under a presence or absence of a base, an ionic liquid and a metal sulfate salt, in water or a mixed solvent of water and an organic solvent:

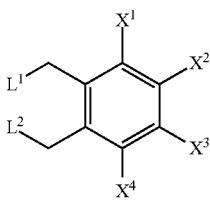

[3]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —$OS(O)_2R^1$, at least one of $X^1$, $X^2$, $X^3$ and $X^4$ is —$OS(O)_2R^1$, and
$R^1$ is $C_1$-$C_8$ alkyl, $C_1$-$C_8$ haloalkyl or $C_3$-$C_6$ cycloalkyl are as defined in claim 1, and $L^1$ and $L^2$ are each independently a halogen atom.

10. The process according to claim 1, wherein $X^1$ is —$OS(O)_2R^1$; $X^2$, $X^3$ and $X^4$ are each independently a hydrogen atom, nitro, a halogen atom, difluoromethoxy or —$OS(O)_2$Me.

11. The process according to claim 10, wherein $X^1$ is —$OS(O)_2$Me, —$OS(O)_2$Et, —$OS(O)_2$n-Pr, —$OS(O)_2$i-Pr, —$OS(O)_2$c-Pr, —$OS(O)_2$n-Bu, —$OS(O)_2$n-$C_8H_{17}$, —$OS(O)_2CH_2CH_2CF_3$; $X^2$ and $X^3$ are hydrogen atoms; and $X^4$ is a hydrogen atom, nitro, a halogen atom, difluoromethoxy or —$OS(O)_2$Me.

12. The process according to claim 3, wherein $X^1$ is —$OS(O)_2R^1$; $X^2$, $X^3$ and $X^4$ are each independently a hydrogen atom, nitro, a halogen atom, difluoromethoxy or —$OS(O)_2$Me; and $L^1$ and $L^2$ are each independently a chlorine atom or a bromine atom.

13. The process according to claim 12, wherein $X^1$ is —$OS(O)_2$Me, —$OS(O)_2$Et, —$OS(O)_2$n-Pr, —$OS(O)_2$i-Pr, —$OS(O)_2$c-Pr, —$OS(O)_2$n-Bu, —$OS(O)_2$n-$C_8H_{17}$, —$OS(O)_2CH_2CH_2CF_3$; $X^2$ and $X^3$ are hydrogen atoms; $X^4$ is a hydrogen atom, nitro, a halogen atom, difluoromethoxy or —$OS(O)_2$Me; and $L^1$ and $L^2$ are bromine atoms.

14. The process according to claim 1, wherein $X^1$, $X^3$ and $X^4$ are hydrogen atoms; $X^2$ is —$OS(O)_2R^1$; and $R^1$ is $C_1$-$C_4$ alkyl.

15. The process according to claim 3, wherein $X^1$, $X^3$ and $X^4$ are hydrogen atoms; $X^2$ is —$OS(O)_2R^1$; $R^1$ is $C_1$-$C_4$ alkyl; and $L^1$ and $L^2$ are each independently a chlorine atom or a bromine atom.

16. A compound represented by Formula [2] or a salt thereof:

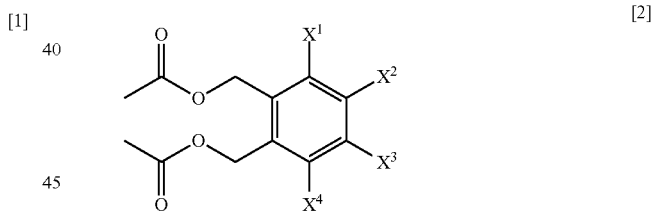

[2]

wherein, $X^1$ is —$OS(O)R^1$,
$X^2$, $X^3$ and $X^4$ are each independently a hydrogen atom, $C_1$-$C_4$ alkyl, C1-$C_4$ alkoxy, $C_1$-$C_4$ haloalkoxy, nitro, a halogen atom or —$OS(O)_2R^1$;
and
$R^1$ is a $C_1$-$C_8$ alkyl, a $C_1$-$C_8$ haloalkyl or a $C_3$-$C_6$ cycloalkyl.

17. The compound or a salt thereof according to claim 16, wherein $X^1$ is —$OS(O)_2$Me, —$OS(O)_2$Et, —$OS(O)_2$n-Pr, —$OS(O)_2$i-Pr, —$OS(O)_2$c-Pr, —$OS(O)_2$n-Bu, —$OS(O)_2$n-$C_8H_{17}$, —$OS(O)_2CH_2CH_2CF_3$;
$X^2$ and $X^3$ are hydrogen atoms; and
$X^4$ is a hydrogen atom, nitro, a halogen atom, a difluoromethoxy or —$OS(O)_2$Me.

18. The compound of claim 16, wherein $X^2$, $X^3$ and $X^4$ are each independently a hydrogen atom, nitro, a halogen atom, —$OS(O)_2CH_3$, or difluoromethoxy.

19. A compound represented by Formula [3] or a salt thereof:

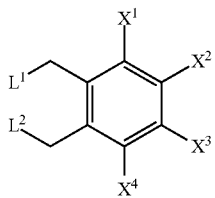

[3]

wherein, $X^1$, $X^2$, $X^3$ and $X^4$ are each independently a hydrogen atom, a $C_1$-$C_4$ alkyl, a $C_1$-$C_4$ alkoxy, a $C_1$-$C_4$ haloalkoxy, nitro, a halogen atom or —OS(O)$_2$R$^1$;

at least one of $X^1$, $X^2$, $X^3$ and $X^4$ is —OS(O)$_2$R$^1$;

$R^1$ is $C_1$-$C_8$ alkyl, $C_1$-$C_8$ haloalkyl or $C_3$-$C_6$ cycloalkyl; and $L^1$ and $L^2$ are each independently a halogen atom.

20. The compound or a salt thereof according to claim 19, wherein $X^1$ is —OS(O)$_2$Me, —OS(O)$_2$Et, —OS(O)$_2$n-Pr, —OS(O)$_2$i-Pr, —OS(O)$_2$c-Pr, —OS(O)$_2$n-Bu, —OS(O)$_2$n-C$_8$H$_{17}$, —OS(O)$_2$CH$_2$CH$_2$CF$_3$;

$X^2$ and $X^3$ are hydrogen atoms;

$X^4$ is a hydrogen atom, nitro, a halogen atom, difluoromethoxy or —OS(O)$_2$Me; and $L^1$ and $L^2$ are bromine atoms.

21. The process of making a compound of Formula [3] according to claim 19, comprising a step of halogenating a compound represented by Formula [4]:

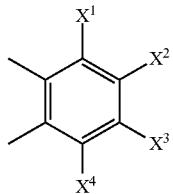

[4]

wherein, $X^1$, $X^2$, $X^3$ and $X^4$ are each independently a hydrogen atom, $C_1$-$C_4$ alkyl, $C_1$-$C_4$ alkoxy, $C_1$-$C_4$ haloalkoxy, nitro, a halogen atom or —OS(O)$_2$R$^1$;

at least one of $X^1$, $X^2$, $X^3$ and $X^4$ is —OS(O)$_2$R$^1$; and $R^1$ is $C_1$-$C_8$ alkyl, $C_1$-$C_8$ haloalkyl or $C_3$-$C_6$ cycloalkyl;

to prepare the compound represented by Formula [3].

* * * * *